US011180791B2

(12) United States Patent
Moqrich

(10) Patent No.: US 11,180,791 B2
(45) Date of Patent: Nov. 23, 2021

(54) MYO1A FOR PREDICTING CONVERSION OF ACUTE PAIN INTO CHRONIC PAIN AND USE OF MYO1A FOR THERAPY OF PAIN

(71) Applicants: UNIVERSITE D'AIX-MARSEILLE, Marseilles (FR); CENTRE NATIONAL DE LA RECHERCHE SCIENTIFIQUE, Paris (FR)

(72) Inventor: Abdelaziz Moqrich, Marseilles (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 16/080,315

(22) PCT Filed: Mar. 7, 2017

(86) PCT No.: PCT/EP2017/055354
§ 371 (c)(1),
(2) Date: Aug. 28, 2018

(87) PCT Pub. No.: WO2017/153424
PCT Pub. Date: Sep. 14, 2017

(65) Prior Publication Data
US 2019/0017089 A1  Jan. 17, 2019

(30) Foreign Application Priority Data
Mar. 8, 2016  (EP) .................................... 16305257

(51) Int. Cl.
| | | |
|---|---|---|
| C12Q 1/02 | (2006.01) | |
| A01K 67/027 | (2006.01) | |
| A61K 31/713 | (2006.01) | |
| C12Q 1/6883 | (2018.01) | |
| A61K 31/7105 | (2006.01) | |
| A61K 31/711 | (2006.01) | |
| A61K 31/7088 | (2006.01) | |
| G01N 33/50 | (2006.01) | |

(52) U.S. Cl.
CPC .......... *C12Q 1/025* (2013.01); *A01K 67/0276* (2013.01); *A61K 31/7088* (2013.01); *A61K 31/711* (2013.01); *A61K 31/713* (2013.01); *A61K 31/7105* (2013.01); *C12Q 1/6883* (2013.01); *G01N 33/5088* (2013.01); *A01K 2217/075* (2013.01); *A01K 2227/105* (2013.01); *A01K 2267/0356* (2013.01); *C12Q 2600/112* (2013.01); *C12Q 2600/118* (2013.01); *C12Q 2600/136* (2013.01); *C12Q 2600/156* (2013.01); *C12Q 2600/158* (2013.01); *G01N 2800/2842* (2013.01)

(58) Field of Classification Search
CPC ................ C12Q 1/025; A01K 67/0276; A01K 2217/075; A61K 31/7088
See application file for complete search history.

(56) References Cited

U.S. PATENT DOCUMENTS

| | | |
|---|---|---|
| 2012/0192298 A1 | 7/2012 | Weinstein et al. |
| 2013/0237454 A1 | 9/2013 | Schutzer |

FOREIGN PATENT DOCUMENTS

| | | |
|---|---|---|
| WO | WO 03/016475 | 2/2003 |
| WO | WO 2004/044178 | 5/2004 |

OTHER PUBLICATIONS

Genbank NG-012104.1, obtained from https://www.ncbi.nlm.nih.gov/nuccore/237858727?sat=13&satkey=4082357 on Dec. 16, 2019 (Year: 2009).*
Donaudy et al., Multiple Mutations of MYO1A, a Cochlear-Expressed Gene, in Sensorineural Hearing Loss, Am. J. Hum. Genet. 72:1571-1577, 2003 (Year: 2003).*
Reynders et. al. Transcriptional Profiling of Cutaneous MRGPRD Free Nerve Endings and C-LTMRs. 2015. Cell Reports 10, 1007-1019 (Year: 2015).*
Siyi Huang. A Convergence of Extrinsic and Intrinsic Signals for Postmitotic Differentiation of Nociceptors. 2013. A dissertation submitted to Johns Hopkins University in conformity with the requirements for the degree of Doctor of Philosophy, p. 1-128 (Year: 2013).*
Donaudy, F. et al. "Multiple Mutations of MYO1A, a Cochlear-Expressed Gene, in Sensorineural Hearing Loss" *American Journal of Human Genetics*, 2003, pp. 1571-1577, vol. 72.
Kim, J. H. et al. "Molecular and prognostic heterogeneity of microsatellite-unstable colorectal cancer" *World Journal of Gastroenterology*, Apr. 21, 2014, pp. 4230-4243, vol. 20, No. 15.
Written Opinion in International Application No. PCT/EP2017/055354, dated Jun. 1, 2017, pp. 1-6.
Tyska, M. J. et al. "Myosin-1a Is Critical for Normal Brush Border Structure and Composition" *Molecular Biology of the Cell*, May 2005, pp. 2443-2457, vol. 16.
Database GenBank [Online] Accession No. NG_012104.1, "*Homo sapiens* myosin IA (MYO1A), RefSeqGene on chromosome 12" May 25, 2014, pp. 1-10.

\* cited by examiner

*Primary Examiner* — Neil P Hammell
*Assistant Examiner* — Tiffany Nicole Grooms
(74) *Attorney, Agent, or Firm* — Saliwanchik, Lloyd & Eisenschenk

(57) ABSTRACT

Products and methods for assessing the predisposition of a subject to develop an injury-induced chronic mechanical pain and/or an inflammatory-induced chronic thermal pain are provided. More specifically, methods for the assessment of the predisposition of a subject to develop an injury-induced chronic mechanical pain and/or an inflammatory-induced chronic thermal pain using the MYO1A gene as a biomarker and methods of treating selected subjects are provided.

Figure 1:
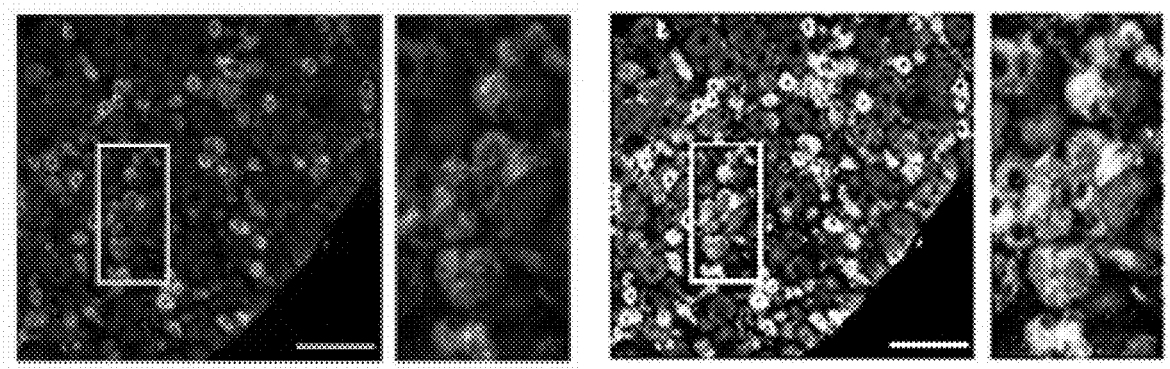
Figure 1:
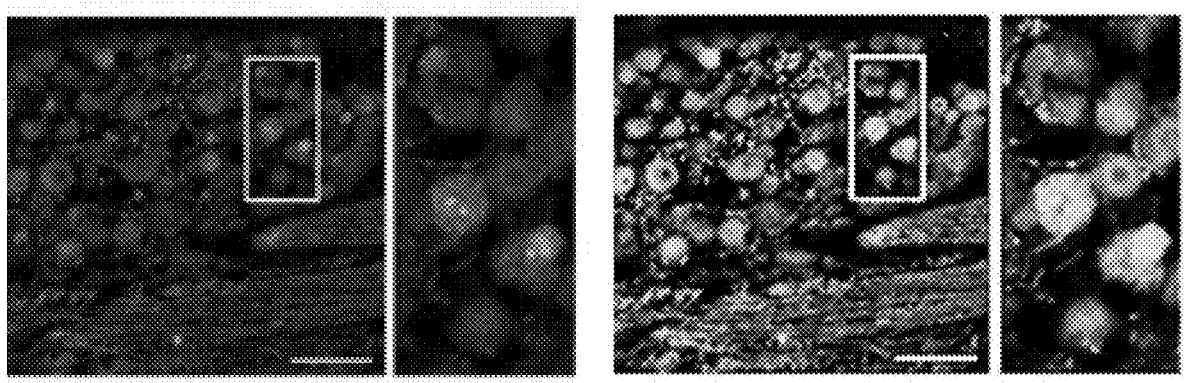
Figure 1:
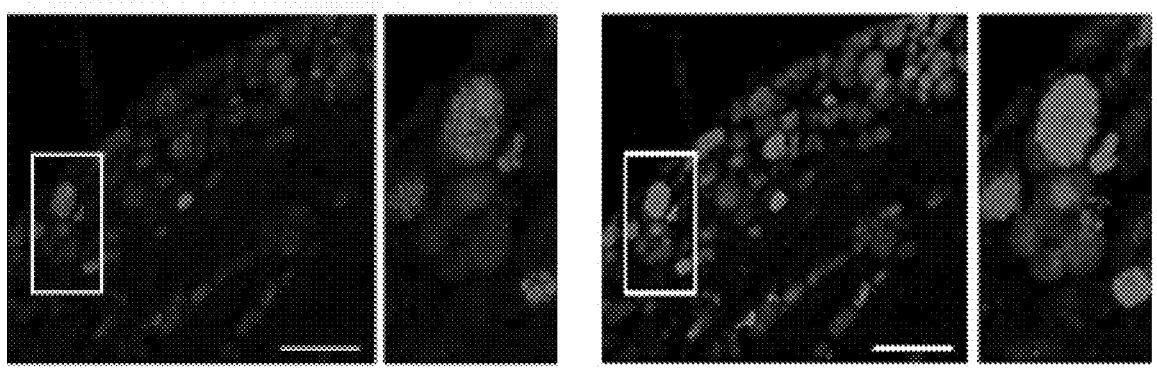
Figure 1:
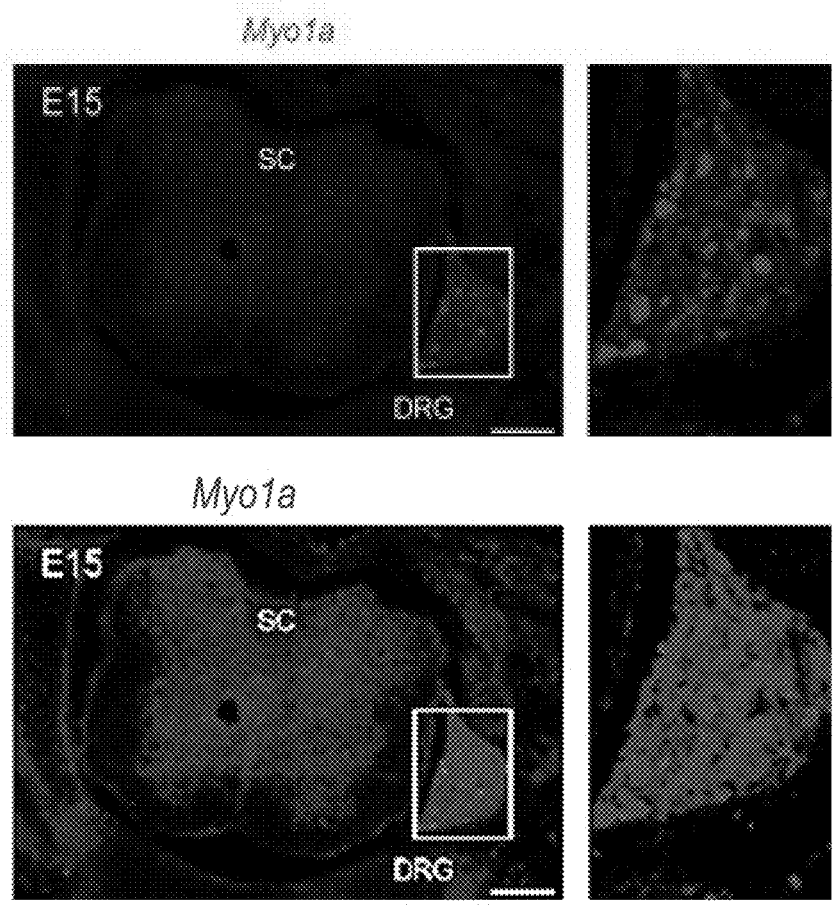
Figure 1:
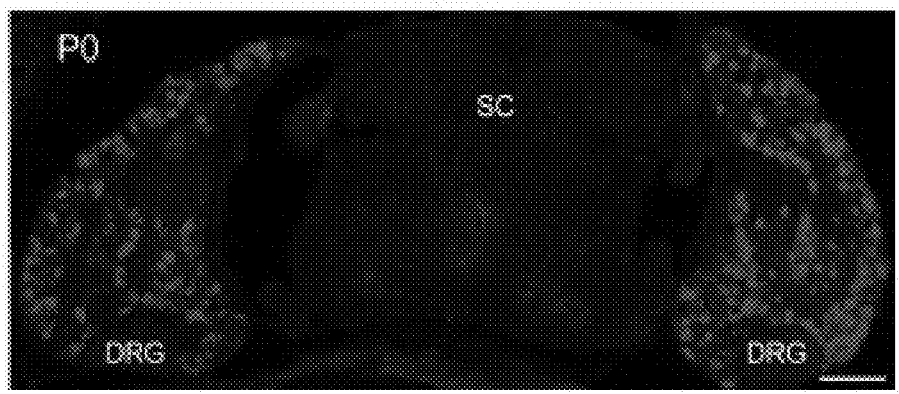
Figure 1:
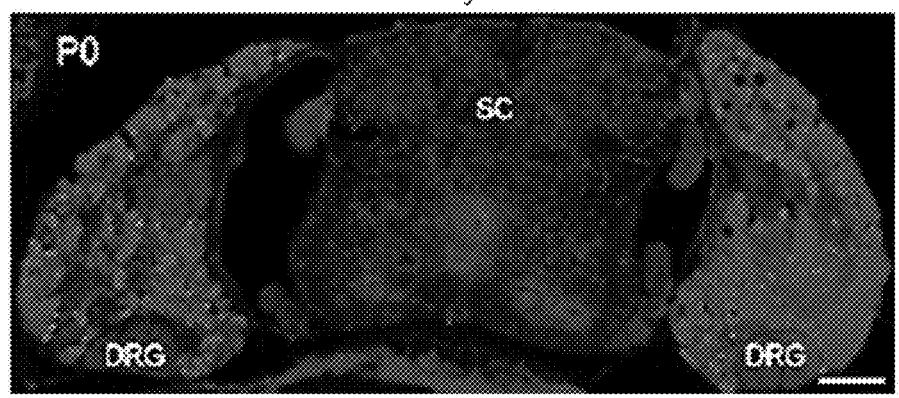
Figure 1:
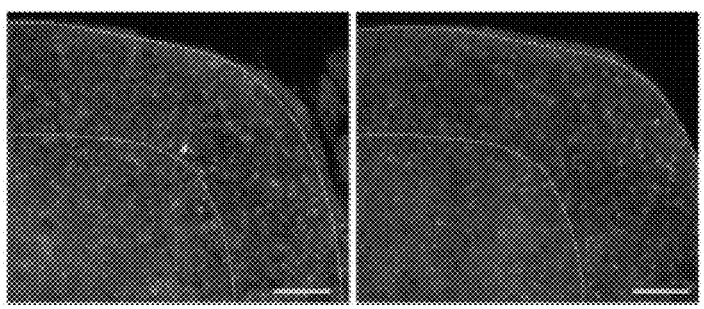
Figure 1:
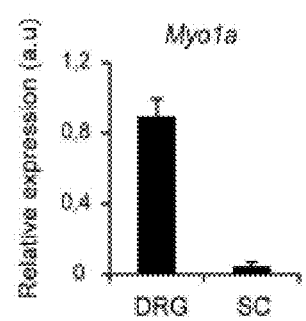
Figure 1:
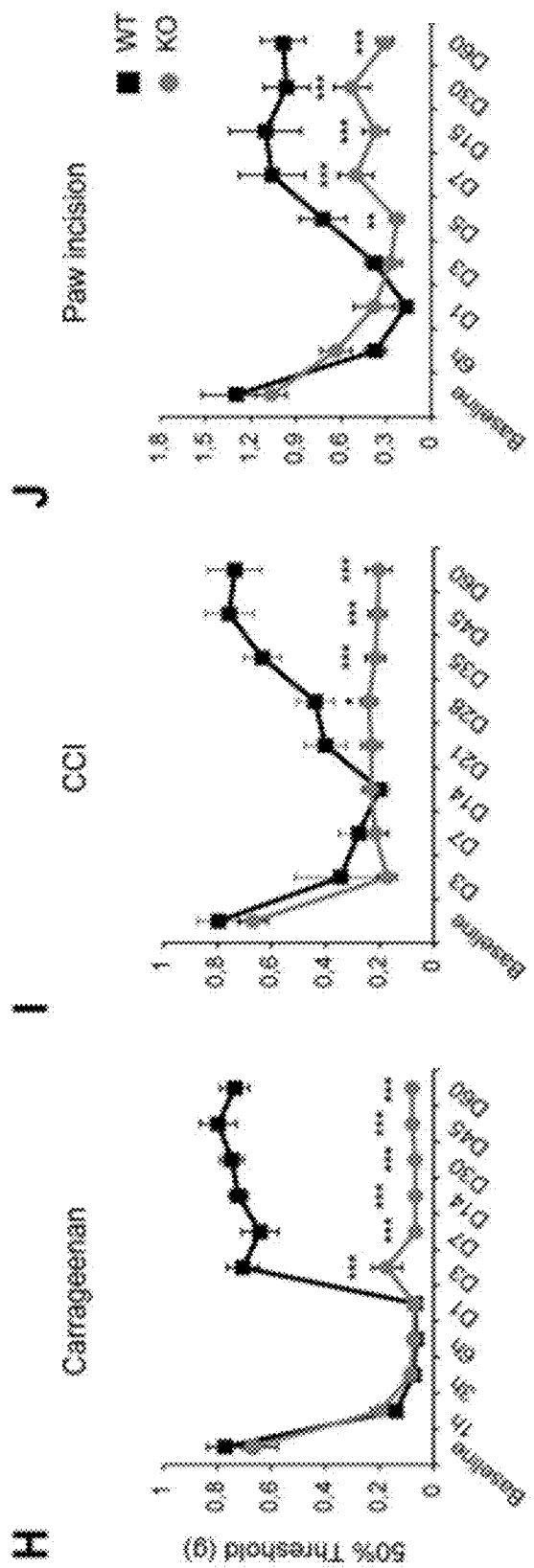

10 Claims, 20 Drawing Sheets
(17 of 20 Drawing Sheet(s) Filed in Color)
Specification includes a Sequence Listing.

E

F  G

SEQUENCE LISTING

<160> NUMBER OF SEQ ID NOS: 25

<210> SEQ ID NO 1
<211> LENGTH: 22249
<212> TYPE: DNA
<213> ORGANISM: Homo sapiens

<400> SEQUENCE: 1

```
aatgcaaggg ggagttcaat gaaactggga catctataca catgtgaggt attattacta      60
atcactttaa tctttgggtc tctatgatag ggtctgattc atggggaag ggaagtggag      120 aagaatttgg ggatttgtc tgcttagctc tccaagtaat ctcattaaca tccctgact      180 cccgataaga taggaagagt aggtatgagg gaggtactgt tttttgcta ggaagacact      240 ctttgtaaag acgtgtctcg ccatgttgcc taggctggtc tcgaactcct gggctcaagt      300
gatcctcccg ccttggcctc ccaaagtgct gggagtatag gcatgagcaa ccgcacttgg      360
ccctacctgt ccttgacaaa attcctgact tctctttggg aaatattttc cttggctata      420
aattccattc ttccagcttt catttccaaa tttgggagac aatggagcaa gaaccctcct      480
ttagttaagc ctctcagcta acgccagcca gatacccttt cctacctaga gggagcttga      540
gtgtctccct ctgggcttc aggcctgtga agggttaagt gagccacacc ctcagcagga      600
acagtctgga ctttgtgctg atcagccatc tccggcctct cctggtttga ctggcacagg      660
```

```
gagcctgggc tggaagaggc agcaaaaggg aaaatcagaa gagtggacac tggcaagagg    720
agggcagcct ttttcccagc ttccttgcac catggacagc tcccattaag ccacctctcc    780
atcctggggc caggactctt atgccccatt cctgtcaaat tgagatttca tccaccattc    840
tccaaggaca gtgaagttat accctagttc cagtgttggg tgagtcctgc cttgacctgt    900
cactgcttct ctttaacacc ttggggcgcc ccatctgggg cctcttgcct tttcccttc     960 cccaccctca accagtcaca ttcccactcc cttcaaatcc aaatccaaag aagatgactg   1020
ctcccaaccc accttctgct tctcacccct ccctgccaag ttagttaaaa gacttagctt   1080
tttgtaaaat ctagaaaata caaaatagt atctacttca tggggatatt gtaagcacta    1140
aatgaattag tgtatgtaca gtgcttagag ccctgcccag ttcgtggtaa acgctgcatg   1200
attcctagag actgctatta ttgatattct tattgcttcc tcagttgtgt ccttctggta   1260
agtgacaagt gctctctttt cctagagctt ggggaaagcc aagtgaaggg agaaggaagc   1320 ctgtgccct tcttgcccca cttccgttcc tccttcctcc gctcctccac ccgggttcag    1380
agatgcaata gcataggagg atgtgtctct ttcattcctg ttcaggagtg gccttgacca   1440
ttgtactaat aatcctgtcc tgtgcctggc cactctgcct actcagtctc acaggaaaga   1500
ctgaggaggg ccaggtttcc tccttaggga cacctgcca tgtgcctact gcatgggggc    1560
caagccccac caccctccct gtagttccaa ctgtgctcct ccttgcccac tcccgcaaga   1620
agctaggtgt gtccctctgg ggcaaagtcc atgccagaag tttacaggag tgggtgtaaa   1680
agctagagat ggaaaaatag agacagacat gtagcacatc cagaggtcct gacaactgcc   1740
tgtttgttgg ggaagcaaac cccactttca ttttctttgg gaaattccaa tctcttatgg   1800
aggaatcctg cctctatcct ctataattct gccttgtcaa gttcccattt taaaaatgaa   1860
gctcactgta gcaatgacag ggaaggagag acctttggaa gaacttctga aatggttatg   1920
ggtaggttgg gtgtctttaa tagggctgt gagaggtaag gtgttgagaa gaagcactgg    1980
gggtagatgg ggagtctgga ccctggccag ggcccattgt aggagagaga gggctttctg   2040
tacctggcgg cagcacaagt ctttgcttac acttttcctcc tcagccctct ctccttcagt   2100
cacaactctg ctcccccagt gtagcccac tgggtgcctg ccttccctg gtggtcagag     2160 gaaggtgttc ctgttccacc cctgcccac ccaccaac tgtaacccag gcagcagagg      2220
atctccccca cctcctgctg agagtttcag cctcccatt agcttgggct ggtccagagg    2280
cctctcctag gttgggggct ctctttaggg ccagggtagg aagagaggaa ggctcttttg   2340
gtccttctgc catcctcccc tcaaacagtt actggcccct aaagctgagt ggacatcagc   2400
aaactgtgcc tcttattccc aggatcagtg gccctctgg acatgcctct cctggaaggt   2460
tctgtggggg tggaggatct tgtcctcctg gaacccttgg tggaggagtc actgctcaag  2520
aatcttcagc ttcgctatga aaacaaggag atttatgtga gtgtcatatg ggtgcctctg   2580
gctgtggata tgtggctgga gaggtcacag gctcccacct caccctcaag ctcattccct   2640
tcaccttctt cctggctcca gacctacatt gggaatgtgg tgatctcagt gaatccctat   2700
caacagcttc ccatctatgg gccagagttc attgccaaat atcaagacta tactttctat   2760
gagctgaagc cccatatgtg agtaggggga ccaaggaag gctgacaggg ccccagcttc    2820
ttgacactga gtcatcctaa tttcctttgt cccttcccct gaaggggctt ctccagctgc   2880 ccettccttc cctggccttc tggaggcccc ttccaaggcc tgtcacatct gcccagtct    2940 gctccaagta gagagagtgg atgaacctgc gtgctggaga ttgagtgaaa gatggtgtct   3000
```

-continued

```
tgaactggtt tcacaatagt cattgcccac ttcctcccca caagctacgc attggcaaat    3060
gtggcgtacc agtcactgag ggacagggac cgagaccagt gtatcctcat cacaggcgag    3120
agtggatcag ggaagactgg tgaggcccct ggctggggga acacatggag tcacctctgg    3180
aactgcttcc ttgtctcttt gcaagccaga cctagacctg accctccacc ccacagaact    3240 tccttttccac tttttctgac tccaagggggt ggtgaggcac tggggtgaag caagttaagg   3300
aggtgggggg atgggctagt cctggtgggg gacccatgag agcgttttgc ctgcacagag    3360
gccagcaagc tggtgatgtc ttatgtggct gccgtctgtg ggaaaggaga gcaggtgaac    3420
tctgtgaagg agcagctgct acagtctaac ccagtgctgg agggtgagaa ttctgctctc    3480
tgccctctcc accctccatc taaccccccag aatcactgag ccctagaccc tcttccccag   3540
tgctgcaaaa tcacctctct tgttcgaccc agaaaaatct gagattgtca tgaggactgg    3600
aagcccttcc tcctttccct tctctagagt ttcacttctc ccctcctcat ctctgtagct    3660
tttggcaatg ccaagaccat tcgcaacaac aattcctccc gatttgtgag taaatgtctc    3720
cccacctggg aagagaggat gtgggggctt aagagggagg aatgtggcac agaccccttc    3780
caggcagggt ggtgagaaga ggaagaagct aagtctctct ctctggtctc tctctgaagg    3840
gaaaatacat ggatattgaa tttgacttca agggatcccc cctcggtggt gtcatcacaa    3900
actgtacgtg tctccccaat tccactcacc tgtcttccac ctgcctccca tggcccttttc   3960 tgctaatctg ttcctgtaga aaggcagaat gttagacgtc aaggagactt cccaaccact    4020
aggaatgccg gcgatggggg cattctccag tagggctgga gaagctacgg catctcccag    4080
gccctcagga tattatttttt ctaattctct gccagatctg cttgagaaat cccgattagt   4140
gaagcagctc aaaggagaaa ggaacttcca catcttctat cagctgctgg ctggagcaga    4200
tgaacagctg ctgagtatgt gcctgcatgg ggaaagtgtc ctcatgagtg acacatggca    4260
aagtccccaa cctccattca gtcccagaac ccctgttccc tctgggcccc tacagccctc    4320
ttcccttgag cctcccagat tttccttgct gcatttccca ttctcagcct cacccactca    4380 tgttgggaa caaattcctt taccctgtg ttctcttcct tttctggggt tttattgcca     4440
gggatatgcc ttcttgcctc ttcactgttc tcgttcctct ttcctgcctg ggttctgctt    4500
tccctgagct ggcttcaaat ataaaacact tatatccatc tactttcctt cctaccttca    4560
acttaagggg atttaattaa agcagggaag caggcagaat gttgtaagtg ttcaggaact    4620
ttcagtgaac tctagttgaa gctgtcctgg gtctacatct gccttaccta ggaccctgtt    4680
cctgattttc ttttcattca ttcattcact cattcattta ttcattcatt caacatctct    4740
tgaacaccta tgatcaaata ttatgctagc ctctagggat acagagttga gtaagacatg    4800
accctgtcct cgaagaactt atagtcttct agggataaga ggtgtgtgag cagatccatt    4860
gtaatattgt gtgatcgggg ccatcaggcc tgtgcagctg gctataagag cagaagacct    4920 agagccccctt ggcttggcct ggggaagggt ccatcacagc ctggatgctg gactggcctg   4980
aagtggctct gggtgggcat cactggagtg tctggtggac tttaagccct actggagttt    5040
gcctcccaat ctcctctctg gctgtgagca ccgtgggtgt ctggcccccta gaatgtctc    5100 tttggtttct ggtgattcta tgatagacct gtgctatctc cttttccact cttggagatc    5160
tctgtgatct tcaggaaccc ctgcagatct catgctcttt cctggcttaa tagttttggt    5220
tatgttcaac ttgtctgcat catgggcatt agtgtcttgt tctggttggt ctgtcatcta    5280
ttggtttaaa tcaactctag atgaggtctc ccaggtatca tcatccccag acattctgac    5340
tcattctccc tccagatacc ctccttagca ggccccttgtt tcaaactttg tgtgctgggg   5400
```

```
gagctgccat tagactatag tttgagggat actccctgat tctcagatca tttgcatacc    5460
agataattga catccctcaa actccatgat taaccgaatc cctcccatcc tagggaaaca    5520
gctttgatca ttcacttgat tcatttatta aaaagagaaa atttcctgca tgccagaaag    5580
gcacacagaa tatggagatg agaaacacag tcccaaccca caagttgctc atttatggga    5640
gagacagaaa aaacaaaac ctagcccata tgatatgggc tgggatatag attcaccagt    5700
ggggaatgca agacagccat ttggctcagg ccctcagcat cagagaaaac ttttcagaag    5760
aggtgtcagg gtcagggaac atgctacctg ccactttatt ggtgtttggt gttcaaacaa    5820
tgaatgagca acccacgcca agagttgagg ctggggcag gcaggagata tgcgcttacc    5880
cttctcccct taccttcacc gtccagaggc acctgcgtag gatggaaggg ttgcttgttt    5940 attttattg tttagaaccc tgagggtagg gagaagagta aaatgagggt tttgtttcat    6000
aaaagttggg ggaaaaccca atcaatatga gcatcaaaac cctaaacact acttaaaagt    6060
atacttaaaa atttagtctg ttaggccgag tgactcatgc ctgtaatccc agcactttga    6120
gaggccgagg cgggtggatt gcttgagtgc aggagtcaag accagcctgg ccaacataga    6180 gaaacccat ctctactaaa aataccaaaa ttagccaggc gtggtggcat gcacccatag    6240
tcccagctac acaggaggct gaggcatgag aatcacttga acctgggagg tggtgcttgc    6300
agtgagctga gatcgcacca ctgccctcca gcctgtgtga cagagtgaga ccctgtctca    6360
acaacaacaa aaattagtct atcatcacag gaattaatga tcccaaaaca aaggaggcag    6420
gggaagaacc caaacaaaa atgactcctt tggataagtg aatgaatcca ttagggcaag    6480
ggctgtgagg tgtcaaggct ggagggctcc agagagcctg ggtactaacc atcttcccca    6540
acactggccc tcccagaggc cctgaagctt gagcgggata caactggcta tgcctatctg    6600
aatcatgaag tatccagagt ggatggcatg gacgacgcct ccagcttcag ggctgtacag    6660
gtgggtgccc agggtgaggc aggcttgggc ccttaggtca tcctctattc gcattggact    6720
ggcaccaaca gttcagcttt tgatttctgc tttctgccta agagtgcaat ggcagtgatt    6780
gggttctcgg aggaggagat tcgacaagtc ctagaggtga catccatggt gctaaagctg    6840
gggaacgtgt tggtggctga tgagttccag gccagtggga taccagcaag tggcatccgt    6900
gatgggagag gtctgcatcc cagcctgctg gagctcctac ccagaccctg aatttcctac    6960
tacaagtcgt gtccttctac catctctagc ataattgatc tcaccctgat gcagtcccac    7020
tcagcccact cctgagttct cccctaaaca gactcactga gaactcccga tgaagcatat    7080
tggaatgagc ttttgaaatt tgatatatct aggtctggaa attctctgag tctgagttga    7140
ttcttctgca gaatggggat aatcacacct aattcaggag attctcatat taaagtagat    7200
gatacatgca aaatgcccag atccccttc ttctgtcccc caactccctg agattcctcc    7260
agggccatgt tctgggttgg ctgcaatgac ttctccagtg agaccccagg acaccagtgt    7320
ctcaggcagt ttcacttatc agattgcact ccctcccctg agagaaagct gcctctaagg    7380
acatgctgta ctttctcatt atcccaggtg ttcgggagat tggggagatg gtgggcttga    7440
attcagaaga agtagagaga gctttgtgct cgaggaccat ggaaacagcc aaggaaaagg    7500
tggtcactgc actgaatgtt atgcaggtaa ggagctcact ggagtggagg gggctgtttc    7560
gaccctgttc tgtgatgcca ccctaatcag ctgtgcctca cccacaggct cagtatgctc    7620
gggacgccct ggctaagaac atctacagcc gcctctttga ctggatagtg aatcgaatca    7680
atgagagcat caaggcaagt ggccgctctg ctttctccat gctctcctgt ctgcctcacc    7740
```

```
ttcctgccct gtcaccagcc ctatatcttg gtttctgaga tgagcagagt agggaggatg      7800
atggggaggg tacagttcct tctaacagtg tgttgtcatg gaaacatcac tggcttttga      7860
gttagacaat ctggatatat catctactta cttaattcaa agtcatgtgg actttcaatt      7920
aagtaaaaag tcatgtggac tttcaatttc acaaaggttc tgggcctcag tgtcctgatt      7980
tggaaatgcc cactaagaaa cactaatatg ctgggtgtgg tggtccatgc ctgtaatccc      8040
aggactttgg gaggctgagg tgggaggatc acttgagctc agtagttcaa gaccagtctg      8100
ggcaatatag tgagacccca actctatatt ttatgaaaaa aaataagtta aataaaaaac      8160
tatttaagaa acactaatgc attcctacct gcttcacagg gtttaataag gatcagataa      8220
attatgtaaa tagttaccat atgataccac aattcccact cctaggtata tacccaagag      8280
aactgaaatt agatgtcctc actaaaattt gtgcacaaat gttcacagaa gccttatttg      8340
taatagccaa aaagtagaaa cagcccaaat gtccatcaac tgatgaagag ataaacaaaa      8400
tgtggtatat ctgtacaaaa gaatgttatt tgtccataaa aagaatgaag tactgataca      8460
tgcttcaaga ttgatgagcc tggaaaacat tatgctgagt gaaagaaggt agtcacaaaa      8520
gaccacattt tgtttgattc cattcatatg aaatgtccac aataggcaaa ttcatagaga      8580
tgggaagtag atcaatgaat gccaagggct ggggggagag gggtatgggg agtgactaat      8640
aatgggtata ggatttcttt tgtggggtgg tgaaaatgtt ctgaaattag atagtggtga      8700
tggttgtaca accttttgaa tatactaaaa agccactgaa ttgtacatgg tatgtgaatt      8760
atattcagta aagctgttat taacaaatta tccacatgga agtgccatct atttagaagc      8820
tattactgaa aggtagtaga ataagaagga atttgagtct aggcttggta agtacctatc      8880
cttctgaaat ttgactttgt tatctgtaaa atgggaacaa taatacctta taaggttatg      8940
ataaataaag acatggaatc ttttgtaaaa tgctctacaa atataagaga tggttattgt      9000
cctgagaggt tttattgtct ttctacctgg taccatcgga gcaccatcct ggaatctatc      9060
tgtatcttcc ttttcctcct ttcctccctc tttgcttgtt ctctagtgtg tggaggaggg      9120
agagtaaaat cacaacaatt cctttccagt ttggcaaagc tcttgctagt tctgtttgcc      9180
ccctactcca accccatccg ctccagaagg acctggcctg gtgtgcagag ggggcctgtc      9240
ctcagattta tctttctctc ctcttcaggt gggcatcggg gaaagaagaa aggtaatggg      9300
agtccttgat atctacggtt ttgagatatt agaggtgaga gtgcctcacc tcagcaccct      9360
gctcccctag gattagaggt ggacaggctc acaggggga tgtgagggag gggaggtagg       9420
actgagacgg agaaacagtc ttggagtgag ctctctaacc tgtgctccct ctctcaggat      9480
aatagctttg agcaatttgt gatcaactac tgcaatgaga agctgcagca ggtgttcata      9540
gagatgaccc tgaaagaaga gcaagaggaa tataagagag aagtaaacca agtctttctct     9600
acttccccct cttaaacaac ttctaggcat atgccagagc ttccttctc cttgatcaca       9660
atttcctcta catcgtcccc agatgtgaac acagaggaca aaatgtttcc cttgcatagt      9720
agatcattcc agcattacca agtagcccta atcctctgct ctccattctt catttccctg     9780
gcctcccagg gtacatgtgt ggaaagtcct gacaagaggg aagtgacagc tgtgcttggc     9840
ctatggcaga ctgtgagcca aatataaaaa ggacatttct tctgggtttg gcccaaccac     9900
atctctttct atgcccttct ctaacatctc agagtccttg gtctcccccg ggccctagct     9960
agagttgctg tccttttcttg taacaccatg atcccagact tcctcaccag aagtacccca   10020
tggctccaat ttctatggct aagtgttaga aaagctctct gattgagctc attaccttca    10080
aagtgtgaat ggctgagagt ctcactcatc aaaaccctcc cagggatgtt cccttgtgag    10140
```

```
ctctcaggaa taggttataa cagaatttca ggcaatgtgg tcacaatgtg tgaaaaagtt  10200
tttttagttg ttttgtatgt tttaatttta acgatttaaa tgatcagata cataatacat  10260
tcccatgctt caaaattcaa aaagcttaga aagtatataa ggaaagtttc cctcctactt  10320
ctgcccctag cctcctagtt ctcctcccca cccagaggca accaacatgg gcttccttcc  10380
agaagtcctt acgcatatgc aagcaaattt gtaaatatat ttccccacaa aatctataca  10440
aatggcagta aatacactct gttctgtacc ttattgtcat cacgtaacga gatctttcca  10500
tgtcagtatg taaggatgct tttttacagc aacacagtat tttaagaata tcataattcc  10560
tttaactggt tggggaaggt atttggggga tgaagtggga ggcaacttaa tttaattttg  10620
ttttctttaa agacctgtga tagagggagg aaagaaagac ctatgcttcc cagccatacc  10680
tgagaatgtc ccagcctgga gcgtctgacc cttgggtggg atcaggagct atcctgtctg  10740
taggcctgat gcccagcaag tccccaaagt agagaacgat tatctttggg tcttctgctt  10800
ttgtaccatt cttgcttttc aaaacattat atagtctcaa agtctcatgt agataaagtg  10860
gttcctaaag ggtagtcctg gaccagcagt atcaaaatca cctggaaaca tgttggaaat  10920
gcagattcca ggcccacatc ccagacctgt tgaatcagaa acttggggag tgggacccag  10980
aaatctgtat tttaacagcc ctccaggtgg ttgtgctgca cactcaaatt tgagaatcac  11040
tgatgtagat ctttgaagat gtatcaaatt agccttgttg tttgatgata aactctcacg  11100
tgctgtggtt ttatagagca cagagtagtg tggccgctgt tgcacatacg catggatcct  11160
tccccactcc cacacaggaa atctctatcc taatcttcac tcaacatgtt acacttccct  11220
ctccacccta caccacctac agggatctct gcattgtctc accctctctc acagctgctc  11280
caattccttc cgtgtgtctg tctacccacc ccacaaattc tccaccaacc ttggagggat  11340
ggggacataa atagaaatca taccaaggac ccctgtgaac tatggggctt tctgatgtcc  11400
tttgttgggt gggtgaaagg ctagatctgg tgaggtctct ggaggcttgt cttggacgtg  11460
ttccctgtaa tttgttgtct cccctgacca gggcataccg tggacaaagg tggactactt  11520
tgataatggc atcatttgta agctcattga gcatgtgagt tgtcattctc ttatctgtgg  11580
gacttcccct tccagactgc ctgaacatcc ttccctgtc tctctccctg attccccact  11640
tggtagggac agtaaagagg gcagaagata agagtggaga aagggggcag caatgagaac  11700
gtggacatct cggaggacca gatttaggtt gggcttcttt tgttccccg gcccagaatc  11760 agcgaggtat cctggccatg ttggatgagg agtgcctgcg gcctggggtg gtcagtgact  11820
ccactttcct agcaaagctg aaccagctct tctccaagca tggccactac gagagcaaag  11880
tcacccagaa tgcccagcgt cagtatgacc acaccatggg cctcagctgc ttccgcatct  11940
gccactatgc gggcaaggtg aaatggcagg gctggagggc agagattagg gctcaggccc  12000
agactgaagt caatggggga ggaacccggg gaaggtgaga gtctggaata cttcacaatg  12060
agactggagg ggcaagtgc tgggacaagg ttgtggggtc tccaaaccaa tagctgctcc  12120
tttacaggtg acatacaacg tgaccagctt tattgacaag aataatgacc tactcttccg  12180
agacctgttg caggccatgt ggaaggccca gcaccctc cttcggtcct tgtttcctga  12240
gggcaatcct aagcaggcat ctctcaaacg ccccccgact gctggggccc agttcaagag  12300
ttctgtggcc atcctcatga agaatctgta ttccaagagc cccaactaca tcaggtgaca  12360
tgctggcatg caggggaaca tgctacatat gtgatgcac gtgcagggtc catgcgctgt  12420
agaacacgtc catgtggggg tgcttctgga ataaggatgt cagaggtcct ttcctcacag  12480
```

-continued

```
aaaacagtca gataaggagc tgagagtccc acaggggggag agcatcagat tcgatagggga    12540 atacatagaa gtgagtgaaa ctggggaggc cagtgtgtct actttctttg aaacttttca    12600
gtgaagtgca ccgtgtgcag catagggggaa tatgatgggt tacactggca atgatgtcag    12660
ctcctgaagg ctgtgcctta ccccaccctcc caccaggtgc ataaagccca atgagcatca    12720
gcagcgaggt cagttctctt cagacctggt ggcaacccag gctcggtacc tgggactgct    12780
ggagaacgta cgggtgcgac gggcaggcta tgcccaccgc cagggttatg gcccttcct    12840 ggaaaggtac cgattgctga gccggagcac ctggcctcac tggaatgggg gagaccggta    12900 agacccatg gggagactgg gcatcaggaa agggcagtgc aggaaacatc tctgggggaa    12960
gagacctgga ggtgcagtgc acatctgctg aagctgggtg aatggatact ttgagaaatg    13020
aattgaatga tcacttcttg gaggctgaaa ggattagggg aaaggtggaa gaggactttc    13080
tcctgagata cccctctgca gctttctgtc atttgcttcc atagggaagg tgttgagaag    13140 gtcctgggg agctgagcat gtcctcgggg gagctggcct ttggcaagac aaagatcttc    13200
attagaagcc ccaagactgt gagttagaga gtgcattagc atttggtgag ggtagaaggt    13260
ggaagagccc acctgagaaa ggctggaggg ggagggagcg tgtataacct ggaatggatc    13320
actgtccagt ggatgggaag cttcctgtct gcaggaaccg tatccctggg aattgaactc    13380
ttgggttcct acactgccct gagcctgggg agcttggtgc tgcatggctc taagtgcctt    13440
tgcctgaggc agagcccttg agggttgggg tgatcaactt ctagcttact gcctgctaca    13500
aagttagagt taagtagata cttgtttact gaatgaataa atgagcaaac taagaagaca    13560
aaggaatgat caaataaggc ctggctggga agcctcagta ctgtgggta taggagagga    13620 cagcactgtt ccctgagcc agtctctctg tcacccccctt ccacctctcc acagcttttc    13680
tacctcgaag aacagaggcg cctgagactc cagcagctgg ccacactcat acagaagatt    13740
taccgaggct ggcgctgccg cacccactac caactgatgc gaaagagtca gatcctcatc    13800
tcctcttggt ttcggggaaa catggtacgg tcatccccaa agtcccactc tgttcactct    13860
aatagggaag atggaaggtg gctcaggagg tgccattttt ctaacaactc ctatgttttc    13920
tacagcaaaa gaaatgctat gggaagataa aggcatccgt gttattgatc caggcttttg    13980
tgagagggtg gaaggtaatg gagagtggaa gagaggtttc ctcacattgt ttctcctgga    14040
ttgtgtcacc tgctggctag agcagcagag agctagtcct gcctgcaccc aggccgcacc    14100
tctgtgtatc agccggtcca tgtgtgggtg ggtgtctggg agtgagaggc ctgtagggga    14160
gacctgtaga ggtgtctggg tgggtagatg cctaacttgg cagcagaact ttgccttctg    14220
ctctaagtgt cctcactgcc aacttgtctg atttttacttc caacttccag ctacagtctc    14280 agctcttttat cttactcagg tctttgcgt gttgaaaaat agtacaacct cttctagaat    14340
ctgcctatct tcactttggc tcctttcttg tacttttctg ccaggcccga aagaattatc    14400
gcaaatattt ccggtcagag gctgccctca ccttggcaga tttcatctac aagagcatgg    14460
taagtggtag gggttagggt ggatgttagg gatggagcag ggaggcacag gtttgggaga    14520
ggggtttgag aagaggcaac ccaaagcttt cccccaagag tttcctcagt ctgcatgtac    14580
ttaagtccta ggagaagagg gcagctacct gcagggacca ggcccagtg ccttggactc    14640 gggggcagaa tcagatagca ttttggcatg agtggacaat ccaggcaacc ttgtggcagg    14700 aagggggtctc agcacaccca ccatctggtc tatggtcaaa tagccttgtg aagatcctgg    14760
ggctggatgt ttaacaactg ttgaagaggc taagcctcat tgaagagtag agtgatccac    14820
acattaacta gctcaaccctc ccaagatcca tttttagggtt ggggtgagag taggcgaatt    14880
```

-continued

```
gtatcttcct tctacttcct ctgaaactat tgtcagcaag tcagaaagta aatctcagga    14940
aggacctatc ctaattctgg aggacgtggg tcaggctgga tgggaagacc cacctggaag    15000
gcctacatat tcaaacttac agacagctcc caggggaga aaaacaggga cagagaagag     15060
taacttctgg agacttcagt cagatagcaa tagtgcttct gagaagtgtc agggaggaaa    15120
ccagggaggg agaagcactt ccaatgaaac cttgggaaag ccagagaga aggaggaaga     15180 gcatgggatc ttggacagag gctggagcaa attggtaatt gacctccgct gattgggttt    15240
ttgaccatag ttaggaccct gactgtgctc attcagacat aagacatgtt tgcttgcagc    15300
ccctctttgt tgtttgagag tctggatccc tcagctcaag agaggaatgg gggctctgaa    15360
gctctggacc tcttttttgc cttcctgagc cttcatttgc tcgtcctctt ccccttccca    15420
gggaagttcc atcttccagg tctcttcagt tgcctgatca cctcttgtgc tggtgccaga    15480
gtgtctgcct tcccaccata catgcttctt gctacacacc tgagacctgt aatctgattt    15540
tgctgttatc tcctgactgc ccttcttctt ccttttcttt catctgtgta ttgtcaggca    15600
gctactaatt gtcaacccag aagctgctgg gtttagacca gggtctcaat aaatcacacc    15660
cccacagaag cctgcgggca ctgggcactg attcccccag tgtttctgag tattccagtt    15720
tgccactgcc ttgactgtaa ctaatgctag tatccattct cattttttta attttatttt    15780
atttatttat ttattttttg agacagagtt tcactcttgt cacccaggct ggagtacaat    15840
ggcgcgatct cagctcactg caacctccgc ctcccaggtt caagtgatta tcctgcctca    15900
gcctcctgag ctgggattac aggcatgcgc caccatgccc agctaatttt tgtatttta    15960 gtagagacag agtttcacca tgttggccag gctggtcttg aactcctgac ctcaagtgac    16020
ccgcccatct cggcctccca aagtgctagg attacaggtg tgagccactg cgcccagcct    16080
atttcttttt tgagatggaa tcttgctctc tcgcccaggc tggaatgcag caagcatgat    16140
ctcggctcac tgcaacctcc atctcccggg ctcaagccat ccttcagcct cggccttccc    16200
agtagctgag accacaggca catgccacca cgcctggcta attttttata tttttggtaa    16260
agatgtggtt tcaccatgtt gcccaggctg gtctcaaact cctgagctca agtgattcac    16320
tcgccttggc ctcccaaagt gctaggatta caggtgtgag ccactgcacc cggccttacc    16380
cattatcttt tgaacatcta ctatgcatta agctctttac atgcattaac tctaatactt    16440
tcaataaccc tgtgaggtag gctctttct ttctcccatt ttgtagttaa aaagccaagg     16500
ctcagagagg ttaaataact tgccgggggt tccacagctg taagtggtaa agctgggtta    16560
caaactattt gactctagag cttttaacca ctgcctaaga ctgcccctca tcaatagagg    16620
cttgggcaac ccatggccct aggcagacct gggggcagga gggctgcata ggaaagggca    16680
gaactttcta gttctagaac aaacaataaa agaagaaag ccttcagagg ctccacatta     16740
attggaacaa aggggattat gacagatgct taggcatgtt tgttgaatta ttaataaata    16800
aaatcagact agggactggg gactccagtc ttggaggcct tcacaggccc agatcccaaa    16860
cccaccaaac ccactagacc tgcagtggaa gctacaatga gcttggatag ttcctgcagt    16920
taacagcaat atactatgta ttctgcctct ttctatttaa attttttaac ctgatatctt    16980
agtaaaactt tttcataaaa attccagaca tttggaagtg ccaaaaatca agtcattttt    17040
tatatcttca gtaattctgt gccataaaca aacaggttgc taggtgctct atgggatgta    17100
aaaccttggc caggcaaggt gactcactcc tgtaatccta gcactttggg aggctgaggc    17160
gggaatattg cttgagccca ggaatttgtg accagtctgg gcaacatagt gagacctaga    17220
```

```
ctctacaaaa aaaatttaaa aattaggtgg gtgtggtggc tcatacctgt agtcccagct    17280
acttggaagg ctgaggtggg aggatcgctt gagcccagga ggcgggcaag gctgcagtga    17340
gctgtgatgg tggcactgca ctccagcctg ggcgacagag caaaaccctg tctcaaaaaa    17400
agaggcaaaa acaaaaactt aagaatcctt gttctagatt ggggcagact aaagagtcag    17460
ttgccatgga tgaagcttga ttggatcctg gaaaaggaaa aataaagctt caaaggacat    17520
gtttagaagt ttataaagga catgtagaga aatctgagag tggatcgctg ttggattagt    17580
gatgttgatt ttcttaggtg tggtgatgga gttatgattg tgtaagagaa tgttccagtt    17640
cttgggagag gcatgctgac atttttaggg t aaaatgtcat gatatctata acctacttta    17700
ggatggtagg gtagcaagga tttgtgtaaa tgtgtatatg catgtattta tatgcacaca    17760
tatgtgtgtg tgtcagagca cacagatagt gcaaggtgtt aacattatca gttggtgcat    17820
ttagatgagg aacatacagt atacagatgt taattgtatc ttttttcaac ttttctgtaa    17880
gttaaaaaaa ctttcaaaat aataagctat attgaatttt taaaacatca tattatgcta    17940
ttcttctgta taaattctcc aatggtgttc catttcactc cttaccacag cctacaaggc    18000
ccatcatgat ctgccccgac ctactctctg atcctctctc ttcctgctca agtgattctg    18060
gccacccttt ttttttcttc tttttttagac agtcttgctc tgtcacccaa gctggagtgc    18120
agtggtgcga tcttggctca ctgcaacctc cacctcccgg gttcaagcga ttctcctgtc    18180
tcaacctcta gagtagctgg gattacaggc atgcgccacc atgcccagct aattttttgct    18240 caccctggct ttttaatgtc tctggaatat gctgccactc attcctgcct cagggtctac    18300
ttctttgcat cacagcagat gccattatct gacatcacac tatatattta tttgcttgtg    18360
tagttggtcc ccttctccac cctacagtag aatgtaagtc cagtgaaaat gaagactttg    18420
ttcactgtta tgtcccagta cctagaacag ttccaggcac taagtagaca ctcaataaat    18480
gttgactagt gaaaaaaaat gtgagacctg ggatcctgcc ttataaggac tcagtgtcta    18540
gaaaagggag ctgttttcca tgcaaataac tgtagtacaa agacgagtgt aggcaaattg    18600
ctatggggct tcaaagaaag gagaggcaat ccggggcttg gggaatcagg gagggctttg    18660
agctgatctc ccaggttggc agagttgagt caagagagca tcgagagcta aggcacacag    18720
tgatcatgca tgggctgggt aggggcatgg gaaagagtcc tgtccgggtg gtgtgcccag    18780
ggaatgcagg ggtcctgcga catgaggctg ggctcttaag tgtcagggag gaaacccagg    18840
agagaaaagc acttccagtg aaaccctggg aaaggccaga gagaaggagg aagagcatgg    18900
gatcttggac agaggctgga gcaaattgta actgacctcc gctgattgga ttttttgaccg    18960 tggttaggac cctgactatt gctcattcag acatgagaca catttgctta cagcctctct    19020
ttgttgttcg agggtctgga tccctcagct taagagagga atggggggctc tgaagctctg    19080 ggcctcttca ttgtctccct gaattcattt gctctttctc ctttgctcct ttatttgctc    19140
cttcttcctt tgaatggagg ctgacatgtt tggacttgac tgatttgaga ggaggggaaa    19200
tttggtacct agccaacagc tgacacagac agtggctgcc acctgtaggc aattgtgaac    19260
agaaggaata gaaagctaca ggagcaaaac tttgagacca gctttcatat tggttcctct    19320
tacctcactg ccctgggtag caggtctttg gttggaacta atcgttctct ccctccagtc    19380
tcctattcat gctcttacct cccggcctca agcctgcacc tcttgctgaa aaagatccaa    19440
gaggtgactc ccttccatct cttcagctcc accccttgct tctcactgtg gttaacttc     19500 ctcctttgaa gtgcaggat ctgggtgcca gtttgcctgt caggaagtgt ttcttatcac     19560
tccactccca atcccctgg tcccaaacta ggtacagaaa ttcctactgg ggctgaagaa      19620
```

-continued

```
caatttgcca tccacaaacg tcttagacaa gacatggcca gccgcccct acaagtgcct    19680 cagcacagca aatcaggagc tgcagcagct cttctaccag tggaaggcaa gtggagccca    19740
ggcacccctc ctctcatttc gtcttttttt tccctccccc tgattttcct cttttgcctc    19800
cctcttctat ttttttccca ttaaaaaaat tgtggtaaaa tatacataac atacaatcta    19860
ccattttaac ggtgtttaag tgtatagttc agtggcatga gcgacattca tgttgttctg    19920
cagccatcac tgccatccat ctccatatgc gtttttcatc accccaaact gaaactctgt    19980
acccattaag caataacccc ctattctccc attccctag ccctgatat cttataatct    20040 actttctgtt tctatgaatt tcactttcc aagtgcctca tataagtggg aatcatattt    20100
gtccttttgt gtctggctta tttcacttag cataaagtaa tttgttcttt tattcaggaa    20160
atgcttattg agcacctgtc tgggactaag ccttgccctg agagctgagc atagagccct    20220
cctggtgctt ttatttgatg gtgtccattc cctcccctag cctccctcag ttctcgcact    20280
cctcctcaat ggtcctccag ccccggcctc tccctgaggt gtctagtgcc tgtccttttt    20340
cctcagtctc tctcctctcc tagtgtcttc tagtcaatat ttctcacctc cctccccagc    20400
cctgccctcc cactctatga ttttagctcc tgtccctcct tcctcacagt gcaagaggtt    20460
ccgggatcag ctgtccccga agcaggtaga gatcctgagg gaaaagctct gtgccagtga    20520
actgttcaag ggcaagaagg cttcatatcc ccagaggtga gggcctccca gaccctgcac    20580
agccagttcc atcacgcagc agttctcaaa cttgagcgtg ccttagaatc acctggcagg    20640
attgtcaccc ccaggtgctg tgtccctcct cagagtctct gatccagcag gtcttggggt    20700
gaggaccaaa atttgccttt ctaacaactc cccaggtggt gctgatgtct tggtcctgga    20760
ctgtgctctg tggacactga cagaggatac gtggatgtgg gggaagggcc cgggaggact    20820
aggatgggaa ctctgggggt ggggaagagg cctctgggcc ttgtcgcgct gcacacctcc    20880
catgtgttct cagtgtcccc attccattct gtggtgacta cattgggctg caagggaacc    20940
ccaagctgca gaagctgaaa ggcggggagg aggggcctgt tctgatggca gaggccgtga    21000
agaaggtcaa tcgtggcaat ggcaaggtaa gggcctgcag gctgaactcc tcccgcagct    21060
agtgcagagc tgtgggctgg catctggaga gcagatggca ggctgtgttt gcgccctgcc    21120
aggtggagtg ggggcaatta atcctgcctt tcctcaccct tgcctgttcc gtccctagac    21180
ttcttctcgg attctcctcc tgaccaaggg ccatgtgatt ctcacagaca ccaagaagtc    21240
ccaggccaaa attgtcattg ggctagacaa tgtggctggg gtgtcagtca ccagcctcaa    21300
ggatgggctc tttagcttgc atctgagtga ggtatcagag ctgggtgggg caagccttgg    21360
actggagaag gtggtatgca tcccagggct ggggcaggct ggaggtgatg gggaccagac    21420
ctttcgctct gggcctttga tgtccctcag gtgctcctga agagaaaaaa tgaatccctt    21480
tcctgctatt tttccctctt cctaagatgt catcggtggg ctccaagggg gacttcctgc    21540
tggtcagcga gcatgtgatt gaactgctga ccaaaatgta ccgggctgtg ctggatgcca    21600
cgcagaggca gcttacagtc accgtgactg agaagtgagg ccatgaactg ggggtgaggg    21660
gcggcttacg gtagatggcc aggctgatgg tcatcgtgac caggatcaga aagcgaagca    21720
tgtagggcag tgcaggccgg ggcttggagg tgtttctcag gccccaccc aggttctctg    21780 gggcctcaag tcctctgact cgcatgatgg gggggccatc atggaaatgc gggagtcggg    21840
gtgaggggat gggcactaga cttggttttc tgttccctct ccaggttctc agtgaggttc    21900
aaggagaaca gtgtggctgt caaggtcgtc cagggccctg caggtggtga caacagcaag    21960
```

-continued

```
ctacgctaca aaaaaaaggg gagtcattgc ttggaggtga ctgtgcagtg aggaggggc   22020 accatgcaga gatggcagtt gcttcctcct gaaccagcac taatccccct ctgccctcct   22080
gtgtgggagg atctctaacc cctctgatcg tggcgcatgg cttggggatt aaactaccct   22140
tgaagaggac ccttgtccca aaccttcttt gttctctcct ccaaaagtag cttcctccaa   22200
cccgcagcct ctctgcacac taataaaaca tgtggcttgg aaaggttca              22249
```

<210> SEQ ID NO 2
<211> LENGTH: 1043
<212> TYPE: PRT
<213> ORGANISM: Homo sapiens

<400> SEQUENCE: 2

```
Met Pro Leu Leu Glu Gly Ser Val Gly Val Glu Asp Leu Val Leu Leu
1               5                   10                  15

Glu Pro Leu Val Glu Ser Leu Leu Lys Asn Leu Gln Leu Arg Tyr
            20                  25                  30

Glu Asn Lys Glu Ile Tyr Thr Tyr Ile Gly Asn Val Val Ile Ser Val
        35                  40                  45

Asn Pro Tyr Gln Gln Leu Pro Ile Tyr Gly Pro Glu Phe Ile Ala Lys
    50                  55                  60

Tyr Gln Asp Tyr Thr Phe Tyr Glu Leu Lys Pro His Ile Tyr Ala Leu
65                  70                  75                  80

Ala Asn Val Ala Tyr Gln Ser Leu Arg Asp Arg Asp Arg Asp Gln Cys
                85                  90                  95

Ile Leu Ile Thr Gly Glu Ser Gly Ser Gly Lys Thr Glu Ala Ser Lys
            100                 105                 110

Leu Val Met Ser Tyr Val Ala Ala Val Cys Gly Lys Gly Glu Gln Val
        115                 120                 125

Asn Ser Val Lys Glu Gln Leu Leu Gln Ser Asn Pro Val Leu Glu Ala
    130                 135                 140

Phe Gly Asn Ala Lys Thr Ile Arg Asn Asn Asn Ser Ser Arg Phe Gly
145                 150                 155                 160

Lys Tyr Met Asp Ile Glu Phe Asp Phe Lys Gly Ser Pro Leu Gly Gly
                165                 170                 175

Val Ile Thr Asn Tyr Leu Leu Glu Lys Ser Arg Leu Val Lys Gln Leu
            180                 185                 190

Lys Gly Glu Arg Asn Phe His Ile Phe Tyr Gln Leu Leu Ala Gly Ala
        195                 200                 205

Asp Glu Gln Leu Leu Lys Ala Leu Lys Leu Glu Arg Asp Thr Thr Gly
    210                 215                 220

Tyr Ala Tyr Leu Asn His Glu Val Ser Arg Val Asp Gly Met Asp Asp
225                 230                 235                 240

Ala Ser Ser Phe Arg Ala Val Gln Ser Ala Met Ala Val Ile Gly Phe
                245                 250                 255

Ser Glu Glu Glu Ile Arg Gln Val Leu Glu Val Thr Ser Met Val Leu
            260                 265                 270

Lys Leu Gly Asn Val Leu Val Ala Asp Glu Phe Gln Ala Ser Gly Ile
        275                 280                 285

Pro Ala Ser Gly Ile Arg Asp Gly Arg Gly Val Arg Glu Ile Gly Glu
    290                 295                 300

Met Val Gly Leu Asn Ser Glu Glu Val Glu Arg Ala Leu Cys Ser Arg
305                 310                 315                 320

Thr Met Glu Thr Ala Lys Glu Lys Val Val Thr Ala Leu Asn Val Met
```

```
                    325                 330                 335
Gln Ala Gln Tyr Ala Arg Asp Ala Leu Ala Lys Asn Ile Tyr Ser Arg
                340                 345                 350
Leu Phe Asp Trp Ile Val Asn Arg Ile Asn Glu Ser Ile Lys Val Gly
                355                 360                 365
Ile Gly Glu Lys Lys Val Met Gly Val Leu Asp Ile Tyr Gly Phe
            370                 375                 380
Glu Ile Leu Glu Asp Asn Ser Phe Glu Gln Phe Val Ile Asn Tyr Cys
385                 390                 395                 400
Asn Glu Lys Leu Gln Gln Val Phe Ile Glu Met Thr Leu Lys Glu Glu
                405                 410                 415
Gln Glu Glu Tyr Lys Arg Glu Gly Ile Pro Trp Thr Lys Val Asp Tyr
                420                 425                 430
Phe Asp Asn Gly Ile Ile Cys Lys Leu Ile Glu His Asn Gln Arg Gly
                435                 440                 445
Ile Leu Ala Met Leu Asp Glu Glu Cys Leu Arg Pro Gly Val Val Ser
            450                 455                 460
Asp Ser Thr Phe Leu Ala Lys Leu Asn Gln Leu Phe Ser Lys His Gly
465                 470                 475                 480
His Tyr Glu Ser Lys Val Thr Gln Asn Ala Gln Arg Gln Tyr Asp His
                485                 490                 495
Thr Met Gly Leu Ser Cys Phe Arg Ile Cys His Tyr Ala Gly Lys Val
            500                 505                 510
Thr Tyr Asn Val Thr Ser Phe Ile Asp Lys Asn Asn Asp Leu Leu Phe
            515                 520                 525
Arg Asp Leu Leu Gln Ala Met Trp Lys Ala Gln His Pro Leu Leu Arg
            530                 535                 540
Ser Leu Phe Pro Glu Gly Asn Pro Lys Gln Ala Ser Leu Lys Arg Pro
545                 550                 555                 560
Pro Thr Ala Gly Ala Gln Phe Lys Ser Ser Val Ala Ile Leu Met Lys
                565                 570                 575
Asn Leu Tyr Ser Lys Ser Pro Asn Tyr Ile Arg Cys Ile Lys Pro Asn
            580                 585                 590
Glu His Gln Gln Arg Gly Gln Phe Ser Ser Asp Leu Val Ala Thr Gln
        595                 600                 605
Ala Arg Tyr Leu Gly Leu Leu Glu Asn Val Arg Val Arg Arg Ala Gly
            610                 615                 620
Tyr Ala His Arg Gln Gly Tyr Gly Pro Phe Leu Glu Arg Tyr Arg Leu
625                 630                 635                 640
Leu Ser Arg Ser Thr Trp Pro His Trp Asn Gly Gly Asp Arg Glu Gly
                645                 650                 655
Val Glu Lys Val Leu Gly Glu Leu Ser Met Ser Ser Gly Glu Leu Ala
            660                 665                 670
Phe Gly Lys Thr Lys Ile Phe Ile Arg Ser Pro Lys Thr Leu Phe Tyr
            675                 680                 685
Leu Glu Glu Gln Arg Arg Leu Arg Leu Gln Gln Leu Ala Thr Leu Ile
        690                 695                 700
Gln Lys Ile Tyr Arg Gly Trp Arg Cys Arg Thr His Tyr Gln Leu Met
705                 710                 715                 720
Arg Lys Ser Gln Ile Leu Ile Ser Ser Trp Phe Arg Gly Asn Met Gln
                725                 730                 735
Lys Lys Cys Tyr Gly Lys Ile Lys Ala Ser Val Leu Leu Ile Gln Ala
            740                 745                 750
```

Phe Val Arg Gly Trp Lys Ala Arg Lys Asn Tyr Arg Lys Tyr Phe Arg
        755                 760                 765

Ser Glu Ala Ala Leu Thr Leu Ala Asp Phe Ile Tyr Lys Ser Met Val
    770                 775                 780

Gln Lys Phe Leu Leu Gly Leu Lys Asn Asn Leu Pro Ser Thr Asn Val
785                 790                 795                 800

Leu Asp Lys Thr Trp Pro Ala Ala Pro Tyr Lys Cys Leu Ser Thr Ala
                805                 810                 815

Asn Gln Glu Leu Gln Gln Leu Phe Tyr Gln Trp Lys Cys Lys Arg Phe
            820                 825                 830

Arg Asp Gln Leu Ser Pro Lys Gln Val Glu Ile Leu Arg Glu Lys Leu
                835                 840                 845

Cys Ala Ser Glu Leu Phe Lys Gly Lys Ala Ser Tyr Pro Gln Ser
    850                 855                 860

Val Pro Ile Pro Phe Cys Gly Asp Tyr Ile Gly Leu Gln Gly Asn Pro
865                 870                 875                 880

Lys Leu Gln Lys Leu Lys Gly Glu Glu Gly Pro Val Leu Met Ala
                885                 890                 895

Glu Ala Val Lys Lys Val Asn Arg Gly Asn Gly Lys Thr Ser Ser Arg
                900                 905                 910

Ile Leu Leu Leu Thr Lys Gly His Val Ile Leu Thr Asp Thr Lys Lys
                915                 920                 925

Ser Gln Ala Lys Ile Val Ile Gly Leu Asp Asn Val Ala Gly Val Ser
    930                 935                 940

Val Thr Ser Leu Lys Asp Gly Leu Phe Ser Leu His Leu Ser Glu Met
945                 950                 955                 960

Ser Ser Val Gly Ser Lys Gly Asp Phe Leu Leu Val Ser Glu His Val
                965                 970                 975

Ile Glu Leu Leu Thr Lys Met Tyr Arg Ala Val Leu Asp Ala Thr Gln
                980                 985                 990

Arg Gln Leu Thr Val Thr Val Thr Glu Lys Phe Ser Val Arg Phe Lys
            995                 1000                1005

Glu Asn Ser Val Ala Val Lys Val Val Gln Gly Pro Ala Gly Gly
    1010                1015                1020

Asp Asn Ser Lys Leu Arg Tyr Lys Lys Lys Gly Ser His Cys Leu
    1025                1030                1035

Glu Val Thr Val Gln
    1040

<210> SEQ ID NO 3
<211> LENGTH: 23212
<212> TYPE: DNA
<213> ORGANISM: Canis lupus

<400> SEQUENCE: 3
gcggattccg ggcctggaga acaggagacc tgggttctgg ttccagctcc gccaggttgg    60
cagtggtgtg atcctgggaa aggggcttct caccctaggt ctgttttctc cctgtgaaac   120
agaggatctg tagtcctttt tgcctctgac acagaggctg cttccactta cacctgggat   180
tatgtgctga tggcacttcc actggcttcc tcctcacttt ctctttccct tgccttttt    240 ctcccttcag atatatatag gagatcaata aatcatgtaa gggcaggttg ataatggaac   300
tgctgatggg ccagtcatct gcagagtgct tctatgagag cagtaaagtt tggaccttga   360
accaagcagc tgtggctggg agttggagga tccagtctct ttgcagctaa gtgtgtgtaa   420

```
tgacccattt gctctttgtg catgcctggg agagagtacg gtaggcagag ggagcctgtt    480
taggaatttt cctgggtgga tgagggggta ccctggtgaa taggattgta taagctcctt    540
atctattgga ggcagctatt tccagctggg ttagtacccg ggaagcagca tatcagggtc    600
tcattcaggt tcctcataca gaaggattaa aattaggaat accaagattt gggctcaaag    660
ctgtggccaa ctgagggtca ggaagctgca ttctgttcct gccacatact gtctgtggaa    720
cctctctgag cctcagtctc tgccgctaat tttcattttc aatggagtga gtagctgcac    780
tgcctagctc acagggtggt gtgattcagt gagatgatac aggtgggaat cggtgagctg    840
acatcgatac aaatgctggg tggtattact aactatagtg tttgggtctg tttgtggggg    900
ctgactcgtg gggggggagg ggaatttggg gatttttatct gcttggttcc cccaagtaat    960
ggtaatgtca ttaataccct ctgacttggg atccctgggt ggcgcagcgg tttggcacct   1020
gcctttggcc cagggcgcga tcctggagac ccgggatcga atcccacatc gggctcctgg   1080
tgcatggagc ctgcttctcc ctctgcctgt gtctctgcct ctctctctct ctctctgtga   1140
ctatcataaa aacaaacaaa caaacaaaaa aaccctctga ctcccaatga gataggaagg   1200
tttgaggcaa gtactgtttc tttgctagga agacacccca gcctaccttc ctctgacaac   1260
atttctgact ttttggaaaa gctttccctt ggctataaat cccactcttg ctcttatttc   1320
caaatttggg gggcagtgga gcaagatgtc tacctgagcc cagccaaata ccctttccta   1380
cctagaaggg gttttctcat gtcaccgagc atctccctct ggggcttcag gcctgggaag   1440
ggttaatcga gccacaccct cagcaggaac agcctcggac tttgtgctga gcagccatct   1500
ctggcctctc ctggcttgat tggcacaggg agccttggtt ggaggaggca gcacagtgga   1560
aggtcagaag cgtggacact ggcgagagga gggaaacccc tttcctggcc tcttggacac   1620
catggacagc tcccattaac gaggatacct ctccattctc cgggccttga gactcctatg   1680
cccccttcct gtcaaattgg gatttcattc accattctcc aagggacacc ctagctccgg   1740
tgttgggtga gtcttaccct aacctgtcac tgctctgcac atcttggggt gccctattct   1800
ggggactgct tctttttccc cttccctccc tccaaccaat cacattccca ctcccctcaa   1860
atccaaatcc aaatccaagg aagatggctt cttccagccc tgcttctact gctcaccatt   1920
gcctgccccg ttacttaaga acttaacttt tatttttaa tctgaaaaat gtgggatgat   1980
aataataact acttcaaggg aatattgttt gtaagcatca aatgaattca tatatgtagt   2040
gtttagagcc ttgcctggcc catggtacct gattgtcaga gattgctatt gtcactattc   2100
tttttttttt tttttaaag atttttattta ttcatgagag acacacacac agagaggcag   2160
agacgcaggc agagggagaa gcaggccccg tgcagggagc ctgatgcggg actcgatccg   2220
gggactccag gaccatgccc tgaaccagaa gcagacgcct aaccactgag ccacccgggc   2280
gtccctattg tcactattct tattgctctt agttttgtcc ttccaagaag tgacaagtgc   2340
tctcattttc tggaacttgg ggaaagcaga gtgaaggctg aaagtagcca gtgttcccct   2400
cttgccccac cttccatttc ttcttccctc ccctcccccg ccaggtttag cattgctgga   2460
gactggaagg atgtggcttt tttatttctc ttagggagta gccctgacca ttgtactaat   2520
gattctgttc tgcaccaggc caccccacct actcagtccc acaggaaaga ctgagggggg   2580
ctgggcttcc tctagaggtt acaactgcca tgtgcccact gcatggggac tgagcctcac   2640
aatgactctg ctcctcctag cccactccca ccagctacta aaaagctagg tgtgtccctg   2700
tggggcaaag tccatgccgg aaggttacag caatgggtgt aaaagctgga gatggaaaaa   2760
```

-continued

```
cagggacaga catataggca tatacagaga tcgtgacagc tacttgatgt tggagaaacc      2820
aacctaatgt ttgtttagga tattctaatc tttttttaaaa aatatatttt attatttatt    2880
tgagagagaa tgtacgtgag cagggaggag gggcagaggg agagggacaa gtaaactcct      2940
tgctaagcag ggggctggac atggggctcg tcccaggacc ctgggactca tagacctgag      3000
ctgcaggcag atgctccatt taattatttt ttaagattta cttatttatt catgagagac      3060
agagagaggc agagacacag gcagagggag aagtaggctc cctgcaggag cctgatgtga      3120
cacttgatcc caggaccccg ggatcatgag ctgagccaaa ggcagacgct caaccaccga      3180
gccacccagg cacccaagg agcaggagat tctcctcact ggaggagagt ttccacaact       3240
tcccacagct agcttgggct agtccagagt ccaccttggg ttgaggactc tctagggcta      3300
agagttggag aggaaggctc ttaggtcctt ctgcccactt cccccacac agctactggc       3360 ccctaaagct gaggagactt cagcaaactg attcctctat tctcaggatc ctctggccat      3420
gaatctcctg gaaggctctg tggggtgga ggaccttgtg ctcctggaac ccctagaaca       3480
ggagcctctg ctcaagaacc tccagctgcg ctatgaaagc aaggagattt atgtgagtgc      3540
atctgggtgc ccctggctgg gggtgtgtgg ccagagagtt catgggctcc tatcccttcc      3600 tcccccctcca aacacccccct accccccac ccctgctcat tctctttacc tttttttggc     3660
tctagaccta cattgggaat gtgttgatct cagtgaatcc ctaccaacaa ctgcccatct      3720
atggcccgga gttcattgcc aaataccagg actataccct ctatgagctg aagcccata       3780 tgtatgtaaa gtggccaagg gaaggctgac cgggccccag cttcctgaca gcgacacacc      3840
ctagtttcct tcatcctttc tcctgagggg gggctctcca gcctccccct tcccccctgg      3900
ccccaggaag ccccttttcct agacctacca ctgcctcagt ctagtccaag tgaggaggga    3960
ggatgactct gggggctgga gatggagtga agctggtgt cttagattaa ccccaccttg       4020
gtcatcacct gcttcctcca cccaagctac gctttggcaa atgtggcata ccagtcgctg      4080
agggaccgag accgagacca gtgcatcctc atcacaggcg aaagcggagc tggcaagacc      4140
ggtgaggcgc ctggctaggg gaggctgtgc aatccctgct agaactactc cctcttctct      4200 ttctcttttcc aagccaggcc tggtcctgcc ccaccccaga aattccttct cggcttgtct     4260
gatcctgagg gctgtgaggt gcgggactta aggggcatta aggagggtgg tggggatcca     4320
tgtgaaggtt tctcttttcac agaggctagt aagctggtga tgtcttacgt ggcggctgtc   4380
tgtgggaaag gggagcaggt gaactccgtg aaggaacagc tgcttcagtc aaacccggtg     4440
ctggagggtg aggattccag tctctcttgt gcacccagc cctaccctac tggccccaga      4500
gacactcagc cctgttctca ttctgcctgg aaaatctgag actggcatga tggctagaag     4560
accttcctcc ttcccttct ccagagcccc cctctcccct ccgatctcct cacctcccct       4620
ctctccatct ctgcagcttt tggcaatgcc aagaccattc gcaacaacaa ctcctctcga     4680
tttgtgagtg atcatctccc tggcctgaga ggagagggtg tgggggcttg agaaggaggg     4740
atgtggcaca daccctgccg gacagggtgg tgagcagagg aagaagcaag gtctctctct     4800 cttctctct ctctctctct ctcacctctg aagggaaaat acatggatgt tgagtttgac      4860
ttcaagggat cccccctcgg tggtgtcatc acaaactgta tgtgtctccc catgctgcca     4920
accacctctc tcgcctccct ggcccacagt tccctctttg cccatttgct atcgtgggaa    4980
ggaacagtag gctggcagga gactgcccag gcacggggga tgccagcgcc gagggcagac     5040
ttggagggaa gcgtggcgt ccccccgttc ctcaggatgc tatttttctaa cccccttctgc    5100 cagatctgct tgagaaatcc cgagtggtga agcagctcaa aggagaaagg aacttccaca     5160
```

| | |
|---|---|
| tcttctatca gctactggcc ggagcggatg cacacctgct gagtatgtgc ctgtcccaga | 5220 |
| cacacaacag aagagcccca acctccgttc agtccctaga gccttgggcc cctctgggtc | 5280 |
| cctgcagccc tcattcctct tcctgcgctc ctcactcagc atctcatctg ctcattgttg | 5340 |
| ggaacaatcc cctgacctct gtgttctctt ctttttcggg gattgtattg ctaggaagaa | 5400 |
| gccttcttgc ctcttgacct cctcttactc ctctctcctg cttgggttcc tctttcccca | 5460 |
| ggctggcttt aaaagcagaa cacttatttc cattttcat tctttcctac cttcaattta | 5520 |
| agggactttt ttgatagctc agcagaaaat catgcaggat attataagtg gtcaggaact | 5580 |
| tttgatgagc tggagttgaa gttgttctgg gtctacctcc acctcatcca ggccctggcc | 5640 |
| ctggtttact cttcttagat ggttttatgg gggttccatt tattcattca tcaaacatct | 5700 |
| cttgaacact tactgtgatg gaacattgtg ctagtctcta gcgattcaga agtgaatatg | 5760 |
| acatggaccg tgtcctcgag aacttgtggt cttccaggga tggcagatgt gtgagcagaa | 5820 |
| acactgcaaa atacagtgtg atcgagtgcc aacaggtctg tgcaggtggc tatgggaggg | 5880 |
| gaagtcacgg aacactctgc ttgtcccagg gagccctgga tcctcgatgg gcccaaggtg | 5940 |
| gctctgggtg ggcatcactg cagagtctgg tgggacttca ggccttgcca gagtttgcct | 6000 |
| cccaatcctg cctctagctg tgagcactgt gggtatctgg ccccaaggac ctgtcgattt | 6060 |
| ggcttctggt tgttttctgc tggacttgta tctatctcct ttcccttcct ggggatttcc | 6120 |
| gtggtttgag agcccctgca ggtctcatta ttccttcctg gctcagtggt cttggttgtg | 6180 |
| ttcagtgtgt ctgaatcata ggcactagta ccttgttctg gttgattctg ttacccattg | 6240 |
| atgtaagcta agtctggctg ggacctccct tgtgtcatca tcccttctg actcattctt | 6300 |
| tgtccagata cctctcttta gtaggttcct gtttcaaaat ttgtgtttct ggggaagctg | 6360 |
| ccattaaact gtagtttgag ggatattccc tgattctcag atcatttgaa taacagataa | 6420 |
| ttgatatcct tcaagctcca tgcttaacct attccttccc atctcaggtg aacagctttg | 6480 |
| actgttccct tgattaaaaa gaaagaagtt tgtacatgcc aggcaggcac acagagtatg | 6540 |
| aagattaaaa tgtcccaatg ctcaagttgt tcatttgtgg gagagacgga aaaaacaaa | 6600 |
| aacctagccc atgtgttatg ggttgggata gagatccacc atggggatca caagagaacg | 6660 |
| gctcagcccc acaacgtcag agaaaatctt ccagaagagg ggtcaggatt ggggaacata | 6720 |
| gcatctgcct tttgttggcg cttagtgaac aaataatgaa tgagctaact ctggccaacg | 6780 |
| gtaagatgtt gaggctggat aggagatatg cgcccgccct tctttcctca cctttgtcct | 6840 |
| ctcagagcct ctgagaactg agcagggtgg agagtttgct tatttatttt tattgtttag | 6900 |
| aaactgaagg tgggaagaag agtggaatga gtcttttctt tcataaaagt cggaagaaaa | 6960 |
| ccccaacaat taagaacatg caaaccctaa atactgctta aaaatttagt ctattattgt | 7020 |
| ggaaactaat gatccccaca caaggaggc tggggcagag cctaaaacga aaatggttcc | 7080 |
| tttgaatgag caagtaaacc aagccagggc aggggctgtg agcgtcaagg ccagaggact | 7140 |
| cctgagagct ccgagtacta accttctcct cacactggcc ctcccagcgg ctctaaagct | 7200 |
| cgagcgagac acaagtggct atgcctacct aaaccagaaa gtgtccagag ttgacggcat | 7260 |
| ggacgacgct gccaacttca aggctgtaca ggtgggtgcc tggggtgggc ccttaggctg | 7320 |
| tccccggagc ccaggatttg gctttgagaa gggaggcgtt gagctggcac cgcacagttc | 7380 |
| agcttctgat ttctgctctg tcctcaagag tgcgatgatg gtgattgggt tctcggagga | 7440 |
| ggagattcag cgggtgctag aggtgacggc cctggtgctg aagctcggga atgtggagct | 7500 |

```
ggcagacgag ttccaggcca atggcgtgtc agccagtagc atccgggatg ggaaaggtct      7560
gtaccgccct gctggtacct gtctcctgca acaccaggtg gctccttgaa gctcctacta      7620
caatttctat tttttcacca tctcctgtgt aactgacttc actcccattc ggtgtcactc      7680
agcctgttcc tgagttcttc cccaaacaca ctcatggaga atcccagggg aggcatttgg      7740
gaatgaggtt atgaagtttg atagacctac attctgggac ctctctgagt ctccctggag      7800
tctttgcaaa gaacctcagg agattctcct cgtaaagcag ataatgcact cagtgtccag      7860
agctccctct ctcttctcct cctcagagat ttctcctggg ccatgctctg gatgggctgt      7920
aaggacattc tcagcaagac ccaggggcac ttgtctccca gcagtgtcat gtctcagccc      7980
ccctccctct ctgggaggga atcccttttc caggccatgc tgtatttcct ccccacccca      8040
ggtattcagg agattgggga aatggtgggt ttgaattcag aggaactaga gaaagctttg      8100
tgctcaagga ccatgaaaac agccaaagag aaggtagtca ctgccctgaa tgtcatccag      8160
gtaaggtccc tatgggagga gggtgatttg gggaccccttc tgtggctgcc atcctaatga      8220
gctggctctg ccctgcaggc tcagtacgct cgcgatgctc tggctaagaa catctacagc      8280
cgccttttca attggatagt gaatcgaatt aatgagagta tcaaggtaag agattactct      8340
cctccctcct gtctgcctca cctttcttgc cctggtcacc actcccatac tttgggttct      8400
gagatgaaca gagtaagaag gatgaatggt aggatacagt tcctcccaat agtgcattgt      8460
tgtgaaaaca tctctggttt tttgagtttg actctctgga tcccctactt accagctgtg      8520
tggcctttca gtttcacaga gattctgagc ctcagttttcc tgatttggaa aattggacac      8580
taatgcctac ctgtttcaca gggcttagtg aggatcagat gaggatcaga tatcagaaat      8640
tccacaccca gatatatatt taagatatat atctaagaga tttgaaaaca ggtgtccact      8700
taaaaaccgt acccatgggg atccctgggt ggctcagcgg tttagcacct gcctttggcc      8760
cagggcacga tcctggagtc ccaggattga gtcccacgtc gggttcctgg catggagcct      8820
gcttctccct cctcctgtgt ctctgcctct ctctctctct ctctcatcaa tcaatcaatc      8880
aatcttaaaa aaaaaaaaaa aaacagggat ccctgggtgg cgcagcggtt tggcacctgc      8940
ctttggccca gggcgcgatc ctggagaccc gggatcgaat cccacatcgg gctcctggtg      9000
catggagcct gcttctccct ctgcctatgt ctctgcctct ctctctctct ctctctctct      9060
gtgtgactat cataaataaa aaaaaaaaaa aacagtaccc aaaagttcat agaggcatta      9120
ttcatactag ccaaaaagtg gaaatgactc aaatgtccat ccgttgatga tagataaaca      9180
aaatgtggta tattcatata atgggatatt atctggccat aaaaaggaaa gaagtactaa      9240
ttcatcctca acatggataa accttgaaaa catacaagga ggagaagcca gacacagggc      9300
acatattgga tgattccatt tatataaaat gtccgaatag acaaatccat ggagattagg      9360
aatagattta tggttagcag ggacttaggg gatgggaagt tggagtgact actaatgggt      9420
atgggtataa gatttctttt tcttttttttg gggggggtat aagatttttt gggggatga      9480 tgaaaatgct ctggaattag gtagtggtga tggtcataca ccttttgaat ataccagaaa      9540
aactcactga agtatatacc tttaaaagta aattttatgg aatgtgaatt ggatcaaaat      9600
agagctattg ttcaaaaatt ctgtacatga aaatgccatc aattcagaag ctattactga      9660
aaggcagcag gagaaaatag gatttgaatc taggtttggg taaacgctta gccctcttga      9720
aatttgattt gttcatctgt aaaatgggaa taatcacacc ttacgggtta tcgtgaggtt      9780
taatgaagta agagcataga attttttgta aaatgctcta caaatctaag agatgattat      9840
tttcctgaga ggatcttaat gtcttcctga ctcccaccct tgggagcacc agcctggaat      9900
```

```
ctgttcatat ctcccttctc ccttcctttg cttgtcctct agcaggaagg aagaataaaa    9960
tcacaacatt tctttcccag catggtcaat ctctctctct ctctctttaa agattttatt   10020
tatatattca ttagagatac acacagagag agaggcagag acataggcag agagaaacag   10080
gctccctcca gggagcctga tgtagaactt gatcccgggg tccctgagcc aaaggcagac   10140
gctcaaccac tgagccaccc aggtgtcccc cagcatggtc aatctcactc gagtttgcct   10200
tctgctccaa tcacctccct ccagatggcc ctggcctggt gtacagagga ggcccatcct   10260
tagagttatc ttttccttcc cttcaggtgg gcgttgggga gaagaagaag gtaatggggg   10320
tcctggatat ctatggcttc gaaattttag aggtgagaga gcttcaccca attgcaacac   10380
cctgctcccc tgggcttgga atgtgtagac tcaaaggggg tggtttgaga gaggggaggt   10440
gtaaggccga gagggaaggg tcttgggctg agctgctccc tctctgcact gggtcccttc   10500
cctcaggata atagctttga gcagtttgtg atcaactact gcaatgagaa gctgcagcag   10560
gtgttcatcg agatgacgct gaaagaggag caagaggaat atgagagaga ggtacgctga   10620
gccttccccc acttaccttc ttggaaatta cttctgggca tgtgccagat ctgtcctttc   10680
ctccatcaca atttcctctc acttgtcccc agatgggaac acaaaggaca aaagtttcc    10740 cttgcacagg tgaacaacag tctagcatta cccagaagcc ctggttgttt ttatttttt    10800 aaagatttta tttatttatt catgagagac agaaatagag gcagagacac aggcagaggg   10860
agaggcaggc tccctatggg gagcccgatg cgggacccaa tcccggatcc ccgggatcac   10920
agcttgagcc aaaggctcaa ccatcaagcc cccaggcgt cctgaagtcc tggttttat    10980 tctccatccc ccagtccccc tgctcctctc ctccacccc tgtaggccac gcaaagaagg    11040
gtcacactga tggaagggtg tgtgtgggga gacctcacaa gggtaaggtg acagctgtgc   11100
gtggcctgcg gcacgctgtg agccagattt agcagggaca tttctcttgg ccttgtcacc   11160
ctaccacatc cctctcggtg cttttctcta atgttacaga attctttgtc tcctcgagcc   11220
ctggctgatg tcagcgtccc ctcttgtagc accctgatcc cagacttcct cctcagacgt   11280
gccccgtggc tcaacatttc cacactcctt ccctggttcg cgaggacctt tgttttctat   11340
ggctaggtgt tagaaaagct atctaattga gctaatccac cccaaagtgt gaacagctga   11400
agtctctcat caaaaccctc ctagggatgg ctgcctgtga gccttcagaa atttcctgtg   11460
cagaatttca gacagcgtgg tcacgatgcg ggggaaaggg ttttctttag ttgtgttgta   11520
tcttttaatt ttaaaaattt aaacgatcag atacagaata cattcctata cttccaaatt   11580
caaaaagctg gggcaactgg gtggctcagg ggttgagcat ctggcttcat tcagctcagg   11640
gtgtgaccct ggggtcctgg aatcgagtcc tgcatcaggc ttcctgcatg gcacctgctt   11700
ctccctctgc ctgtgtctct gcctcttttt tcctttcttt ttaagatttc atttatttat   11760
tcataagagg cacagagaga gagagagaga gagagagaga gagagagata ggggcagaga   11820
cacaggcaga gggagaagga ggctccatgc agggagccca atgcaggacc taattccggg   11880
tctccgggat cctgccctga gccgaaggca gcgctatgcc gctgagccac ccaggctgcc   11940
ctgtgtctct gcctcttgat gtctctcatg aataaataaa taaatctaa aaaaaaaaa    12000 aaaaaaaaaa aaaaaaagg agacgaagca ccttaacgaa ctgagccacc caggtgcccc   12060
cattcttttt tttttttttt ttaatacatc tgaggttagg ctgctaggat ttttttaaa    12120 ttttattat ttattcatag agacacacac agagagagag gcagagacac aggtagaggg    12180
agaagcgggc tcaagcaggg agcccaatgt gggactcgat cccgggtctc caggatcatg   12240
```

```
tcccgggctg caggcggcac taaaccactg caccactggg gctgcccagg tgcccctatt   12300
cttgctgttt cttttttttt ttcttaaact atacaatccc aaagtatcag gtggattagt   12360
ggctcttaaa ctgtgtcctg tgccagtagc atcagcaacc cctcttagga aggcagattc   12420
ctgggctctg tcccagacat gctaaatcag aaaccctgca ggtggggccc agcagtctgt   12480
tttcccaagc tccccagata agtgtgatgc aagtgggagt agcactgatg taggtctttg   12540
aagatgtatc aagttaggtg tgttgtttga tgaagttggc tcatgtgctt tggttttata   12600
ggtcattgca agagcagtgc agtcatttga tcttgcacat actcagggac ccttccctcc   12660
tcccacactg gggtaatccc tatcctagcc ttcactcaac gtgttacact tccctctcca   12720
caccacagca cctacagggc tctctgcagc atctcccact ccctcacagc tgctttgggt   12780
cctcccatga gtctatccac tcacctcacc aattctccac caacgtagaa gggatgggaa   12840
cctaaacaga aaccacacca agcacccctc ttaactatag gatttttctg agcccttttgt  12900 ggggtgggtg aaaggaagcc tgagtcccat gaggtcttcg aagacttgtc ttggacctgc   12960
tcctgtaacc tgtcatgtct cttccttgcca gggcatacca tggacaaagg tggactactt   13020
tgataatggc attatctgca acctcattga gcatgtgagt tacccttctc tcatctctga   13080
gacctacttc ctcttccaga aactgcctga atatccttgc cctgtctctc ccatcctctt   13140
ccactgctcc acttggtaag gatggtaagg aggacaaagg atgaggtgca gtggggcggc   13200
agtgaagatg tggacatatt ggagaacctg gcctacgttg ggctgatctt gtttccctga   13260
ccagaatcag cgaggcatcc tggccatgtt ggatgaggag tgcctacggc ctggggtggt   13320
cagtgactcc accttcttag caaagctgaa ccagcttttc tccaagcatg atcactatga   13380
gagcaaagtc acccagaatg cccagcgcca gtatgaccac accatgggcc tcagctgctt   13440
ccgcatctgc cactatgcgg gcaaggtgac acagcagggc tggagggtag agactagggc   13500
tggacatgag tggaaggcaa tgggggaaga aactgctggg agatgatatt tgggaattct   13560
tcatgatgag actgggagca ccaagtgctg gacaaggtc atgggcctcc agaccaatag    13620
ctgttcctct acaggtgact tacaatgtga acagcttcat tgataagaac aatgacctac   13680
tcttccggga cttgtcccag gccatgtgga aggcccagca cccccctcctt cggtccttgt   13740 tccctgaggg agatcccaag caggcatctc tcaagcgccc cccaactgct ggggcccagt   13800
tcaagagttc tgtggctata ctcatgaaga acctgtattc caaaaacccc aactacatca   13860
ggtgacatgc tgggcatata gggacatgac atgcagcata cacgatggca catgcagtat   13920
ccgtgcgcta tagaatttgt ccattgcagc aggggtggga tggtctctgg aaaagcctca   13980
tcagaggccc tttcctcata aaatataaag ccagataagt tgctgagagt cctatagcag   14040
ggagagcatc agactttggt agggaccatg catgctatag tgagcgaagc tcagaaggcc   14100
agtgtgttca cttcctctga aaattttttct actaagggga atatgtgcag aatagggttc   14160
cagagaccag gatgggtcat gcttgcaaag gtgaagctcc tgaggcctgt gccttgcacc   14220
cttctacccc aaggtgtata aagcccaatg aacatcagca gcgaggtcag ttctcctggg   14280
atctggtggc catccagact cagtacctgg gactgctaga aaatgtgcgg gtgcgacggg   14340
cgggctacgc ctaccgccag aggtacgagc ccttcctgga acgtaccga ctgctgagcc     14400 ggagcacatg gcctcgctgg aatgggggag accggtaagg cccctgggga agactgggga   14460
gcagggaagg gcagggcggg aaccatctgg gggctgggga gagagcagag agtgccatgg   14520
aaatcaccaa agctctgtga atagatacct ggggaaatgg atgatcactt ttcagaagtt   14580
ctgaagtcta ttcaagccct gaactcttct ccctgggtat atggagttga cgaaaggtga   14640
```

```
aagaagaccc ttccctggga tgcccctgag cagctttccc tatctgttcc tgtagggagg   14700
gggtcgagaa ggtcctggga gacctgaact tgtcctcaga ggtggccttc gggaagacaa   14760
agatcttcat cagaagcccc aggacagtga gttggagagg ccccttgtgt ttggcggggg   14820
tgggaggcag agggttggag agcccacgag tgagatgctg gggtaacggg cagcatctgt   14880
aactggagat agatggtggg tgaggaagtc tgttctcggc aggggctttg tccctgggac   14940
ctgaatcctc gggctaccac cctgccctga gccctggcag ttaggtgctt gcacggttca   15000
ccctgagtgc ctctagctga actaggactc ttgaggctcc gggggatgtg ccactcctgt   15060
ctgagtgtct gaacctagca caggcctggg acagagttta gtaggtgcct gttgagtgag   15120
tgaacagctg aatgaaggtg ctaaggaagc actggctggg aaggccctgg cacccacggc   15180
accggagagt agcacagttt ccccaggcca gcctttctgc ccctctttcc ccatttctgc   15240
agctgttctt cctggaagag cagcggcgcc tgcgcctgca gcagctggcc acgctcatac   15300
agaaggtcta cagaggctgg cgctgccgga ctcactacca gctgatgcgc aagagtcaga   15360
tcctcatctc ctcctggttt cggggcacca tggtattggt cacccccag tctgatcccc    15420
atcactccga taagaggctg gaagcaggag agagatggtt cgggacatgg agtttcttct   15480
aacagtccta ttcttttctg cagcaaaagc aacgatacga aagatgaag gcatcagcag    15540
tgttgatcca ggcttttgtg agagggtgga aggtaatggg gaattgcaga ggggtttcct   15600
cccctacgtg ggcccttccc ccatgtggct tctcctggat tgtgccagct gctggggaga   15660
aatatagtag cagaaagcaa gtcctgccca cacccaggac gtcctgtgat gtgatggcat   15720
gtctgagtct gggtgtgttt ccgggtgcac tgatgtgtgt ctgggagtgc gggtgcgcat   15780
tggggagaga gtatgtatgc ctggatgcat ctcccacctg gcggcagagc tctgcctgct   15840
gctttaagcg ccctcctctt ggccaacgtg tctgcctgta cactctccct ccagcaccag   15900
ctcggctctt gatctttctg tgtcctttgt gtgggtgaga gacagtagaa cctccgctag   15960
aacctcctct aggtctaact gtctatcttt attttggctc ctttcttgaa tgtccttgcc   16020
aggcccgcaa gaattatcga aaatacttcc gatcaggggc tgccctcacc ttggcaaatt   16080
tcatctacat gagcatggta agtggtaggg gtcaaaagtg gaaggtgggg ggttgaggag   16140
ggagggacag gtttgaaaa ggaagatgag ggatttgaga agatgtgact caaagttttc     16200
ctccaaaaag cttctccact ctgcttgtac ttaattttt ttttaagat tttatttat       16260
cattcatgag agagagatag gcagagggag aagcagggtc cacacaggga gcccgacgtg   16320
ggactcgatc ccaggtctcc aggattgggc cctgggctga aggcagtgct aaaccactga   16380
gccacccggg ctgccctgta cttaattatt aagtcctagg atacaacgta acggggcagc   16440
aacccacagg gagcaggctc cagtgtcccc tcgtgcattc tggcatgagc ggacactgca   16500
ggcaaccttg tggcgggaag gggccccagc acaccctcac tggtccatag tgaatagttt   16560
tgagaagaga tgggctgggt ggttaacaac agtggaagag tctgagcctc gtggaagagt   16620
gctgtgaaga tgcacacagg gtgaattaac ccagccttcc aagatccatt ttagggttgg   16680
ggtgaaggtg gaggaatcat atctcttttc cacctcctct gaaactagag caagtgagtc   16740
caaaaattaa atctcaggaa agatcttaat tctggaaagc ttgactccag gtggcaagac   16800
gaagccagga catcaaacta tgggcagttt ccagtgagag gaaagcagac agaggaggct   16860
ggtttctgga gatgtccacc caatagcgac ggtgctcctg aagagtggtg agggacagca   16920
gacaggtagc taggagcatt tccagcaaaa ccttgagaaa ggccagagag agggagggag   16980
```

```
agcaagacat cttggacaga gggctgcggt aaaagagaac tggcttctgc tgattctgtt   17040
tttgacagtt gttagggctc ttactaatta tgcttgagag acacactgga gctcccttt    17100 gtggttggag aggcgggatt cctaggtcga attgtggaat gaggtctctg gtctccttat   17160
cacctcccta agtgttcact gtgcccctct ctcgccccag ggaggttcca tcttcccagc   17220
cctcttccat tgcctgtgtc tccagctggc tgtagggcgg ctgccttcct agaggacatg   17280
ctgtcttgct gcatacctga ggcctgcaat ctgatttgac acttatctcc agactgatcc   17340
ctcctctacc ttttctttca cctgtacatt atcaggcatc tgctgaatgt caccccagga   17400
gctgttgggt ttagactaat atctcattga atcacaaccc ctgcagaagc atgcatacag   17460
gggccactcg gcatcgattc ctccagtgtt tctaactagt ctgtattctg ctgttgcctt   17520
gcctataacc aatgctgata cttattatct tttgaacact tactatgcgc taagcccttc   17580
acatgcatta actctaatgc tgtcaaaaat cctgtgaggt agattcttgt ctttcccaca   17640
ttttgtaggt aaaaaactga ggcctagaga ggctgagtaa ctcactaggg gtcccacttg   17700
tggtaagtgc aagagagctg ggatacaaac tctttgactc cagagtttta acgcctgcct   17760
gagattgtct ccccacactg tcccccccacc accacccata gaggcctact cggggcagaa   17820
gggctataaa gggaaaggca ggactttcta gatctagaaa aaacaaacac ttaaaaaaag   17880
aaaaccctca gaggttccac atcaattaga acatggggga ttgcatgaaa tgcttaggaa   17940
tatttattga attaaatcaa actagaccag accaaggact ggggatttaa acgaaggtct   18000
aaggtgatta gaccaagcct gctagatctt tgtagtggaa gaatcaaaga gcttggatag   18060
ttcttagagg ggtacagcaa tatactgagt gtattgcctt tttctcttac aattttctca   18120
aactaatgtc ttagtagaac atttttata aaaataccca aaacgtggaa gtgctcaaaa    18180
atcaagtcat ttttttaaata atttattttt tttagagaa agagagcatg agtgagtaag    18240
gcagagagag gtgggggagg ggcagaggga gcgagagaat cctgaagcag actctgagca   18300
gagcgtggag cctgacgtgg ggctcgagct cacaaccctg agatcatgac cttagctaaa   18360
atcaagagtt ggccacttaa cctactgagc ctgggcgccc caagagcaag ccatttctt    18420 tatcttcaag tctacctcac aaatagagtg ctgggtgctc cctgggctat aaagacttag   18480
gggtccttgt tcaaattggg ggagactaaa cagatgccat gggtgaaact tgattggatc   18540
ctagaacagg aaaaataaac acaaaacttt ttttaaaagg acattttag aagtttataa    18600 aggacattag gaaaaatttg cacatgcatc gctgttggat gagtgtatct aattaacgtt   18660
agtcttctta cattggaggt ggaattatga tttgtatagg ataatgtcct agttcttgga   18720
agatacatgc ttaagtttta gggaaaaaaa tgtcatgatt tctataacct actttaggat   18780
gatatggtgg caaagattta tctatatgtg catatgtgtg tatttatata tttatactca   18840
ttggttatat atgtgtgcat gtgttagaga gcctgcaagt agggcaaggt gttaatatca   18900
gttggtgaat ttagggagga gtatatggta tacaattgtt tgctgtaatg ttttttaaa    18960 cttttatgta agtttaaaaa ctttcagagg cacctgggtg gctccatttg gtaaagccat   19020
ctgcattcag ctcaggttgt aatcccaggg ccttgggatg agaccctgg tgtcaggctc    19080 cctgctcagc ggggagtctg cttctccttc tccctctgcc cctcccctt gctcatgctc     19140 tctctctctc tctctctctc tcaaataaat aaaatctttt ttaaaagct tcaaaataa     19200 gacaataagt tgtataaatt ttttaaaaat taagtcagat tatatcactc tttcccttaa   19260
aatcctttat ggtgttctgt ttcactccga ataaagcca gtgttcttat ctcagcctac    19320
aaggcccttc atgacctgta cttgaccagc caactctctg atctcctctt gctcgattta   19380
```

```
atccagtcac tcttttttgtt tctggaatat gctgtcactc attttctgtc tcagggccag   19440
cttttttttg cagcatagca tataaattta tctgacattc catgatatgt tcacttgctg   19500
tgggttgtct cctttcccac ccccagtaga gtgtaagtaa gctcaatggg aatagagacc   19560
ctgctctgtt cattgctgtg tctccatacc tagaacagtg tcaagcatag agcagacact   19620
caataaatgt ggaatggtga gggaaaaaaa actcagctgg ggatccagac ccccaaggac   19680
tcgctgtcta aagaggaaa aagttttcca tgcaaataac agtagtccaa acacagaagt   19740
atagaccaag tgccatgggg cttcagagaa aggagaggca gccttggttt ggggaatcca   19800
ggaggacttt gaactacatc tcaaaggaca ggtaggatct gagtgggcag agctgagctg   19860
agcgtagaat gggctaaggc acagagtgat gatgcatggg ctggtcggag gccacgatga   19920
ggagtcctgt ctcagaggtg tgccgagatg gtgcagggga tcctgcagca cgaggctggg   19980
ctctaagtag aagacttcta atgccagatt gaggtgttgg gcttgactga tgagtgagga   20040
ggggagatgg ccactgcaga cagtggcggc cagctgtagg catgtgcgaa gtgagacagc   20100
cataggggca aaatatggag gccagttttc atcttggttc ctctcacctc atgaccctgg   20160
gcagcaggtc tctacttgga actaatcctt ccctcccttc ggtctcccat gcatgctctt   20220
actagccagc ctccatgctt ctccctctgg gtggcctccc tcttttttag tagcaggatc   20280
tggatgagaa tttgtctgtt gggaggtctt tcttctcatc agtccactcc caatctcccc   20340
ccgcccccgc ccccaccgtc tgcattccca atctagacac agaagttcct gctggggcta   20400
aagaacaatt tgccatctac caacatcctg gacagaacgt ggccagctgc cccatacagg   20460
tacttccaca cggctaacca ggagctgcag aaactcttct accactggaa ggtgagtggg   20520
gccggggagc ctctcctctc atttgtcttt ttccctcct ccctctgatt ttcctcttct   20580
gcctccctct tccacttttt tttttctt aaagcataca tgacaaacct ggccatttta   20640
accatttta agtagacagt tccgtggcat taagcacatt catattgttg tgccaccatc   20700
actactaccc atctccatac tattttcat cctcccaaac tgaaactctg aacacattag   20760
acagtaaccc ccagtactgt accagtaccc ggtaccagta accccccact cctccagccc   20820
ctggcatgta gactctactt tctctgagtc cgactgttct aggcacctca tataagtaga   20880
atcatacatt tgtccttta tgtctggttt attgcactca gcacagtgtt ctgccatcgg   20940
gaaatactta tcgagcacct tctagactag gccttgcgct gtgtgctggg catacagcct   21000
tccctcctag ggctggcatt tgatcatctc catccgtctc ccccagagtc cctcagcccc   21060
cagtcctccc ccagccctgc cctctctgaa gtgctagagc ctcttccatt ccctgtctct   21120
cctcttctcc agtccctgcc ctccctccac ctctgagtac cccccaacc ccccagcccc   21180
ttgcctccct gagcttagcc ccgaccctcc ccctcacagt gcaagagatt ccgggatcgg   21240
ctgtccctga agcaggtaga gatcctgaag gagaagctct gtgccagcga actgttcaag   21300
gacaagaagg cttcctaccc ccagaggtga gagcccctca ggccctgtgc atgtccattg   21360
agagcacaga gaggatcctc caggtgggat agggtggtgg ttcccaaact tgaatgtgca   21420
tcagcaccac ctggcaggct tgataacacc cagactgctc caccccttc tcaaagtttc   21480
tgaatcaaaa ggtctggggc tgtgggccca agaatttgcc tttctagtaa gtccccaggg   21540
ggcgcagctg ttggtcctgg accatgctct gagaaccact gagatagagg ataggtggga   21600
ggatgggaaa agaagcacaa gaggactagg atgggcctc actgtgagga ggtgctgggc   21660
cttgggggtc aggggcaagg actgaggctc cactgcatac ctcctgtgtg tcctcagtgt   21720
```

-continued

```
cccgatccca ttccacggtg actacattgg gctgcaaggg aaccccaagc tgcagaaact    21780
gaagggtggg gcggaagggc ccattctgat ggcggagact gtgaagaagg tcaatcgtgg    21840
caacggcaag gtgaaggctg gcgtcctgag cctgctccag agccttgggg ctgctagctg    21900
gaggggtggg ggttagccct cacccttcct cacacttccc tcttctgtcc ctagacttcc    21960
tctcgaactc ttctcttgac caaggggcat gtgattctca tagacaccaa gagttcccag    22020
gccagaactg tcattgcgct ggacaatgtg gctggggtgt cagtcaccag cttcaaggat    22080
gggcttttca gcttacatct gagtgaggta tcagagctcc aggggtgcag gccctcacac    22140
tggaggtggt aggcatccca gggtcggggt gggctggagg tgatgggggcc cagacccctc    22200 actctgggcc ttcaataccct cttagcctgc tcctatggaa gaaaaatgaa tcccttcctc    22260 attctttttcc cccttcctaa gatatcatca gtgggttcca aggggggattt cctgctggtc    22320 agcgaacatc tgattgaact actaaccaaa atgtaccagg ctgtgctgga tgccacacag    22380
aagcagcttc cagtcaccgt gactgagaag taaggccatg agctggtgct gagggccagc    22440
ttggggacag atgaccaagc tgttggtcat tgtgaccagg agaatttgtg tagtcagaaa    22500
ctgaagcaca ctccgtcagg gcaaggctcg gaggtgcttc ttagtctccc cacccaagtt    22560
ctctggggcc ctgagtcttc tgactcgagg ggaggagatg tactaccttc aggaagggga    22620
gggaaagcca tagtgcaaat atgggagtag gggtgagggg atgggggga tgggctttac    22680 ccctctctat tccccgtcca gattctcact gaagttcaag gagaacagag tggatgtcaa    22740
ggtcatccag ggccctgagg gtggtaaaaa tggcaagcta agctgcaaga agaaagggag    22800
ccgttgcctg gaagtgactg tatagcgtgg aggtggaggc ttaacacaga gactgcagct    22860
ttgtctcctg gatcagggcc aatcccaccc acccactcac ccaccgaccc acccacgttt    22920 gtgggggat ctcatgtcca acccctctga cccttgtatg gggctcagag actgaagaac    22980
ccttgaagag gacctttcct ctcccaagct cttccagtcc cctctccctt agaacttagc    23040
ttcctcccac cctcaacctc cttgctcact aataaaacaa gtgacttccc aaacatttga    23100
ttaatgtggg tgggtccctg ttccccccacc tttgcagggc ttgtattttg tctgccttca    23160
cccccttccc ctccttgggc tccttggagc tagcaaatac agataataag aa            23212
```

<210> SEQ ID NO 4
<211> LENGTH: 1041
<212> TYPE: PRT
<213> ORGANISM: Canis lupus

<400> SEQUENCE: 4

```
Met Asn Leu Leu Glu Gly Ser Val Gly Val Glu Asp Leu Val Leu Leu
1               5                   10                  15

Glu Pro Leu Glu Gln Glu Pro Leu Leu Lys Asn Leu Gln Leu Arg Tyr
            20                  25                  30

Glu Ser Lys Glu Ile Tyr Thr Tyr Ile Gly Asn Val Leu Ile Ser Val
        35                  40                  45

Asn Pro Tyr Gln Gln Leu Pro Ile Tyr Gly Pro Glu Phe Ile Ala Lys
    50                  55                  60

Tyr Gln Asp Tyr Thr Phe Tyr Glu Leu Lys Pro His Ile Tyr Ala Leu
65                  70                  75                  80

Ala Asn Val Ala Tyr Gln Ser Leu Arg Asp Arg Asp Arg Asp Gln Cys
                85                  90                  95

Ile Leu Ile Thr Gly Glu Ser Gly Ala Gly Lys Thr Glu Ala Ser Lys
            100                 105                 110
```

```
Leu Val Met Ser Tyr Val Ala Ala Val Cys Gly Lys Gly Glu Gln Val
            115                 120                 125
Asn Ser Val Lys Glu Gln Leu Leu Gln Ser Asn Pro Val Leu Glu Ala
130                 135                 140
Phe Gly Asn Ala Lys Thr Ile Arg Asn Asn Ser Ser Arg Phe Gly
145                 150                 155                 160
Lys Tyr Met Asp Val Glu Phe Asp Phe Lys Gly Ser Pro Leu Gly Gly
                    165                 170                 175
Val Ile Thr Asn Tyr Leu Leu Glu Lys Ser Arg Val Val Lys Gln Leu
                180                 185                 190
Lys Gly Glu Arg Asn Phe His Ile Phe Tyr Gln Leu Leu Ala Gly Ala
            195                 200                 205
Asp Ala His Leu Leu Thr Ala Leu Lys Leu Glu Arg Asp Thr Ser Gly
210                 215                 220
Tyr Ala Tyr Leu Asn Gln Lys Val Ser Arg Val Asp Gly Met Asp Asp
225                 230                 235                 240
Ala Ala Asn Phe Lys Ala Val Gln Ser Ala Met Met Val Ile Gly Phe
                245                 250                 255
Ser Glu Glu Glu Ile Gln Arg Val Leu Glu Val Thr Ala Leu Val Leu
            260                 265                 270
Lys Leu Gly Asn Val Glu Leu Ala Asp Glu Phe Gln Ala Asn Gly Val
275                 280                 285
Ser Ala Ser Ser Ile Arg Asp Gly Lys Gly Ile Gln Glu Ile Gly Glu
290                 295                 300
Met Val Gly Leu Asn Ser Glu Glu Leu Glu Lys Ala Leu Cys Ser Arg
305                 310                 315                 320
Thr Met Lys Thr Ala Lys Glu Lys Val Val Thr Ala Leu Asn Val Ile
                325                 330                 335
Gln Ala Gln Tyr Ala Arg Asp Ala Leu Ala Lys Asn Ile Tyr Ser Arg
            340                 345                 350
Leu Phe Asn Trp Ile Val Asn Arg Ile Asn Glu Ser Ile Lys Val Gly
        355                 360                 365
Val Gly Glu Lys Lys Lys Val Met Gly Val Leu Asp Ile Tyr Gly Phe
    370                 375                 380
Glu Ile Leu Glu Asp Asn Ser Phe Glu Gln Phe Val Ile Asn Tyr Cys
385                 390                 395                 400
Asn Glu Lys Leu Gln Gln Val Phe Ile Glu Met Thr Leu Lys Glu Glu
                405                 410                 415
Gln Glu Glu Tyr Glu Arg Glu Gly Ile Pro Trp Thr Lys Val Asp Tyr
            420                 425                 430
Phe Asp Asn Gly Ile Ile Cys Asn Leu Ile Glu His Asn Gln Arg Gly
        435                 440                 445
Ile Leu Ala Met Leu Asp Glu Glu Cys Leu Arg Pro Gly Val Val Ser
    450                 455                 460
Asp Ser Thr Phe Leu Ala Lys Leu Asn Gln Leu Phe Ser Lys His Asp
465                 470                 475                 480
His Tyr Glu Ser Lys Val Thr Gln Asn Ala Gln Arg Gln Tyr Asp His
                485                 490                 495
Thr Met Gly Leu Ser Cys Phe Arg Ile Cys His Tyr Ala Gly Lys Val
            500                 505                 510
Thr Tyr Asn Val Asn Ser Phe Ile Asp Lys Asn Asn Asp Leu Leu Phe
        515                 520                 525
Arg Asp Leu Ser Gln Ala Met Trp Lys Ala Gln His Pro Leu Leu Arg
```

```
              530                 535                 540
Ser Leu Phe Pro Glu Gly Asp Pro Lys Gln Ala Ser Leu Lys Arg Pro
545                 550                 555                 560

Pro Thr Ala Gly Ala Gln Phe Lys Ser Ser Val Ala Ile Leu Met Lys
                565                 570                 575

Asn Leu Tyr Ser Lys Asn Pro Asn Tyr Ile Arg Cys Ile Lys Pro Asn
                580                 585                 590

Glu His Gln Gln Arg Gly Gln Phe Ser Trp Asp Leu Val Ala Ile Gln
                595                 600                 605

Thr Gln Tyr Leu Gly Leu Leu Glu Asn Val Arg Val Arg Arg Ala Gly
                610                 615                 620

Tyr Ala Tyr Arg Gln Arg Tyr Glu Pro Phe Leu Glu Arg Tyr Arg Leu
625                 630                 635                 640

Leu Ser Arg Ser Thr Trp Pro Arg Trp Asn Gly Gly Asp Arg Glu Gly
                645                 650                 655

Val Glu Lys Val Leu Gly Asp Leu Asn Leu Ser Ser Glu Val Ala Phe
                660                 665                 670

Gly Lys Thr Lys Ile Phe Ile Arg Ser Pro Arg Thr Leu Phe Phe Leu
                675                 680                 685

Glu Glu Gln Arg Arg Leu Arg Leu Gln Gln Leu Ala Thr Leu Ile Gln
                690                 695                 700

Lys Val Tyr Arg Gly Trp Arg Cys Arg Thr His Tyr Gln Leu Met Arg
705                 710                 715                 720

Lys Ser Gln Ile Leu Ile Ser Ser Trp Phe Arg Gly Thr Met Gln Lys
                725                 730                 735

Gln Arg Tyr Glu Lys Met Lys Ala Ser Ala Val Leu Ile Gln Ala Phe
                740                 745                 750

Val Arg Gly Trp Lys Ala Arg Lys Asn Tyr Arg Lys Tyr Phe Arg Ser
                755                 760                 765

Gly Ala Ala Leu Thr Leu Ala Asn Phe Ile Tyr Met Ser Met Thr Gln
                770                 775                 780

Lys Phe Leu Leu Gly Leu Lys Asn Asn Leu Pro Ser Thr Asn Ile Leu
785                 790                 795                 800

Asp Arg Thr Trp Pro Ala Ala Pro Tyr Arg Tyr Phe His Thr Ala Asn
                805                 810                 815

Gln Glu Leu Gln Lys Leu Phe Tyr His Trp Lys Cys Lys Arg Phe Arg
                820                 825                 830

Asp Arg Leu Ser Leu Lys Gln Val Glu Ile Leu Lys Glu Lys Leu Cys
                835                 840                 845

Ala Ser Glu Leu Phe Lys Asp Lys Lys Ala Ser Tyr Pro Gln Ser Val
850                 855                 860

Pro Ile Pro Phe His Gly Asp Tyr Ile Gly Leu Gln Gly Asn Pro Lys
865                 870                 875                 880

Leu Gln Lys Leu Lys Gly Gly Ala Glu Gly Pro Ile Leu Met Ala Glu
                885                 890                 895

Thr Val Lys Lys Val Asn Arg Gly Asn Gly Lys Thr Ser Ser Arg Thr
                900                 905                 910

Leu Leu Leu Thr Lys Gly His Val Ile Leu Ile Asp Thr Lys Ser Ser
                915                 920                 925

Gln Ala Arg Thr Val Ile Ala Leu Asp Asn Val Ala Gly Val Ser Val
                930                 935                 940

Thr Ser Phe Lys Asp Gly Leu Phe Ser Leu His Leu Ser Glu Ile Ser
945                 950                 955                 960
```

```
Ser Val Gly Ser Lys Gly Asp Phe Leu Leu Val Ser Glu His Leu Ile
            965                 970                 975
Glu Leu Leu Thr Lys Met Tyr Gln Ala Val Leu Asp Ala Thr Gln Lys
        980                 985                 990
Gln Leu Pro Val Thr Val Thr Glu  Lys Phe Ser Leu Lys  Phe Lys Glu
        995                 1000                1005
Asn Arg  Val Asp Val Lys Val  Ile Gln Gly Pro Glu  Gly Gly Lys
    1010                1015                1020
Asn Gly  Lys Leu Ser Cys Lys  Lys Lys Gly Ser Arg  Cys Leu Glu
    1025                1030                1035
Val Thr  Val
    1040

<210> SEQ ID NO 5
<211> LENGTH: 20110
<212> TYPE: DNA
<213> ORGANISM: Felis catus

<400> SEQUENCE: 5
tgaagttaca ccctagtttg ttccagtgtt gggtgagtct tgccttgacc tgtccctgct      60
ctgcatcttt tggggtgccc tatctgggag ctgctttgtt tttccctttc ccacctccaa    120
ccaatcacat tcccactccc ctcaaatcca atccaaaga agatggcttc ttccagccct    180
atttctgttt ctcacccttg tctgccaagt tacttaaaag tttaacttct gttttttaat    240
ctggagcatg tggaatagta atagtttcta ctttgtgagg atactgtttg taagcatcaa    300
atgaattagt atatgtagtg tttagagctc tgcctggccc atggcacctg attgtttgcg    360
attgctactg tcagtattct tattgctttc tcagttgtgt ccttccagga agtgacaagt    420
gctctcattt tctggaactt gggggaggca tagtgaaggc tgaaggcagc ctgtgttccc    480
ctcttgcccc accttcagtt cctgcttccc tccctcccc cgcccaggtt cagcattgct    540
ggagactagg aggatgtggc tcttttattc ctgttaggga gtagccctga ccattgtact    600
aataattctg tcctgctcca gaccacccca cctactcagt cccacaggca agactgagga    660
gggctgggct tcctccttcg gttacacctg ccatgtgccc actgcgcagg ggatgagccc    720
cacaataact ctgttcctcc ttgcccactc ccaccagctg ctaaaaagct gggtgtgtcc    780
ctatgggca aagtccatgc cggaaggtta cagcaatggg tataaaaact ggagatagaa    840
aaatagatac atccagagat cctgacagct acttgatgtt ggagaaacca aacttttatt    900
ctcttcaggg tattctaatc ttttatggag gaacttctgc ctctgttcct ctaactcatc    960
aacttatccc atttaaaaga tgaatcttga tgtggcaatg taagggatct ttggaagagc   1020
ttttgcaatg gttctgggtg gactgggtga ctgaaataga agctgtgagg gatagagagt   1080
tgagaaggag aactggggc agagggtcag ggagtctgga ccctggccag ggcctcagcg   1140
caggacagag caagttttca gagttaacct ttcctcccca gccctctctc ctgcaagcac   1200
aactgtgctt cccaggtgc tacctgctgg gtgccttcct taccctggtc aaaggcagat   1260
ggtcctgtcc caccctgcc cctccctgct ggggagagtt tctgcagcct cccacagtta   1320
gctttgacta gtccagagga ccctaggtt gaggattgtc tctagggccc agagttggag   1380
aaggctcttt aagtccttct gccctcctca cacacccctt ccccccccct caccccccc   1440
cccacacaca gttactggcc cctaaagcag agcagacttc agcaaactga cctccttact   1500
cccaggatca gcagaacctc tggacatgac tctcatggaa gactctgtgg gggtggggga   1560
```

```
ccttgtgctc ctggaacccc tggaggagga gcctctgctc aagaacctcc agctgcgcta    1620
tgaaaacaag gagatttatg tgagtgcata tgcgtgcccc cggctctggg tatgtggtca    1680
gagagttcat gtgctcccac tcccttctcc cctctcagcc tccctaacc ccaccgctgc     1740
tcattctctt tacttttttt ggctccagac ctacattggg aatgtgttga tctccatgaa    1800
tccctaccag cagctgccca tctatggtcc agagttcatt gccaaatacc gggactatac    1860
cttctatgag ctgaagcccc atatgtaagt aaaggaactg agggaaggct gacagggccc    1920
taacttctga cagtgagaca ccctaatttc ctcgatcctt tctcctgaag gaagttctcc    1980
ggcttcccct tccccactgg ccccaggaag acccttccta ggcctatcac ttacctcagt    2040
ctagtccaag tgaggagggt ggatgactct ggaggctgga gattgagtgg aaggtagtgt    2100
cttggattag ctccacatca gtcttcacct gcttcctcct cccaagctat gctttggcaa    2160
atgtggcata ccagtcactg agggaccggg accgagacca gtgtatcctc ataacgggcg    2220
agagcggagc cggcaagact ggtgaggtgc ctggcttggg gaggctgtgc agtcactgct    2280
ggaaccaccc cctcatctct ttccgagcca gacctggtct tgccccaccc cagaaattcc    2340
ttcccacttt ttctgattct gaggggtatg gtgctggaat gacaggagtt aaggagagtg    2400
gtggggatcc atgtgaaggt ttctcttgca cagaggccag taagctggtg atgtcttatg    2460
tggcggctgt ctgtgggaaa ggggagcagg tgaactctgt gaaggagcaa ctgcttcagt    2520
caaacccggt gctggagggt gagtatccca gtctctgccc tctccaccct ccaccctgct    2580
ggcccagaga cactcagccc tacaccctct taccctgttc ttgttcagct tgaaaactct    2640
gagattggcc tgatgactag aagacgtcct tccttcccct tctctcgagc ccctcttctt    2700
ccctcagtta cctcaccttc tctctcatct ctgcagcttt tggcaatgcc aagaccattc    2760
gcaacaacaa ctcctctcgc tttgtgagtg accatctccc tggcctggga ggagagggtg    2820
tgggggcttt agaaggagga atgcagcaca gacccctcc tgagtggggt ggtgagaaga    2880
agaggaagca aaacctcttt ctctctctgg tctctgtagg gaaaatacat ggatattgag    2940
tttgacttca aaggatcgcc ccttggtgga gtcatcacaa actgtacgtg tctccccatt    3000
ctgcttacca gctctctctt ctccccatcc cacagtgtcc cttctggtg atttgaaacc     3060
gtaggaagga atagtaggct accaggaggc ttccctacta gtaggaacac cagcggagag    3120
ggcaggctta gagggaagcc gtggaatctc cctgagctct aggacattat tttctaattc    3180
cctgccagac ctgcttgaga aatcccgagt ggtgaagcag ctcgaaggag aaaggaactt    3240
ccacatcttc tatcagctac tggccggagc agatgcacac ctgctgggta cgtgcctgcc    3300
cagacacatg gaagaaggtc cccaacgtcc atttaatccc tagaaccttt gggcccctct    3360
gcaccctgc agccctcttt ccctgagccc tcagcctcct tcttcctgca ttcctcacac     3420
tgaatttcgt ccactcattg ttggaaacaa tcccctgacc tctgtgttct cctctttttt    3480
ctaggattgt attgctagga ataaaccttc ttgtctcttg acctgctctt attcctctgt    3540
cctgcttggg ttcctctttt ctcaggctgg cttcagaaat gggacactta tttccaccta    3600
ccgttcttcc ctatcttcaa tttaagggac ttaatcacta gctcagcaga aaatcagaca    3660
ggatatttaa gtgttaaaga aattttgata agcagtagtt gaagttgttc tgggtctaca    3720
tctgcctcac ccagcccctg tccttgattt cttcttctta gatggcttga tggaggtttc    3780
atgtattcat tcatcaaata tctccttgaac acctactatt atcgaacatt gtgctagcct    3840
ctagcaatgc agagttgaat aagataacat ggctcttgtc ctcgaagaac ttaaggtctt    3900
ctagggatga cagatatgtt caataggcct gtgtgggtgg ctgtaggagc agaaggcatg    3960
```

```
gagacctctg ccttgtcctg gagagccctg ggtgctggat gggcctgagg tggttctggg    4020
tgggcatcac tgcagagtct ggtgggactt cgggccctgc cagagtttgc ctcccaatgc    4080
cccctctagc tgtgagcagt gtgggtgtat ggcccccaag gacctgtcct tttggttcct    4140
ggttattctc tgctggactt gtgcctatct cttttcccct cctagggatc tccatggttc    4200
aagagccccc acaggtctca ttattccttc ctagctcagt agtcttggtt gtgctcaatt    4260
tgttcgaatc ataggcacca gtatcttatt ctgtctgact gttacctatt ggcttaagct    4320
aagtctggac agggcctccc tggtgtcatt atcccagggc ctttctgact cattctttat    4380
ccagacacct ttctttagca ggttcctctt tcaaaatctg tgtctcaggg gaagctgtca    4440
ttaaactcta gtttgaggga cttccctga ttctcagatc atttgaataa cagatcattg      4500
atatccctca agctccatgc ttaacctact tcttcccatc tcaggtgaac agcttggatc    4560
ataaccttga ctcatttatt aaaagaaaa aagtttatgt atgccaagca ggcacacaga      4620
aaacaaagat gaaaacaca gtcccaatgt gtcgttcatt tgtgggagag acagaaaaaa      4680
caaaacctag cccatgtgtt atggactggg atagagatcc accatggggg aacacaagag    4740
agccttttgg ctcagcccca caatgtccaa ggagagtttc caggagaggg gtcaggatta    4800
gggaacatag tacctgcaac tttgttggtg cttactgaac aaataatgaa tgagccaacc    4860
caggcctagg gtgagatgtt gaggctctgg gtgggtggga gatatgtgct caccggtctt    4920
tcctctctga gccactgaga actgagtagg atggagggtt ggcttgtttg tttttattgt    4980
tgagaaccct gaggatggga agaagagcag aatgagtctt ttctttcatc aaagttagga    5040
aaacccccac aattaagaat acccaaactc taaatactgc ttgaaagttt agtctattat    5100
aatgggaatt aatgatccca aaacaaagga ggcaggggac gaaccgaaaa caaaaatggc    5160
tccttcgaat aaatgagtaa accaagctag ggcaagggct gtgagagtca aggccggagg    5220
actcctgaga gcctgggtac taaccctcct cccaagcact ttaacgtttt ctagttgcca    5280
aaggatataa agtacatgat taaatgctaa ctccccatga aatcattgcc ttccacattc    5340
agcacaggga tccaagcctg ctttgtttga tgggaaaggc cactacaatt tactggtcat    5400
ttaaaagtag aatttctgtt gcctataaga attagaggga ggtttatacc ctatgatgca    5460
tatagacaaa aaacctatca aaattcatta taactagttt gtgaatataa aatgaaagca    5520
catagttaga gttggtgact ttaaaaagat tgaatgttga atcagattct catactgacc    5580
cttgcagagg ccctgaagct cgagcgggac acaagtcatt atgcctatct gaaccagaaa    5640
gtgtctagag ttgatggcat ggacgatgcc tccaacttca agtctgtaca ggtgggtgcc    5700
cagggtgggc cttaggctat cccctgagcc caggctttgg ctttgagaag ggaggcattg    5760
agctggcacc acagttcaac ttctcatttc tgctatctcc tccagaatgc aatgactgtg    5820
attgggttct cggaggtaga gattcagcag gtgctagagg tgacggccct ggtgctgaag    5880
ctggggaacg tggagctagc agatgagtcc caggccaatg ggacatcagc aagtggcatc    5940
cgtgatggga gaggtctgca ccgccctgct ggtaccctct aagccgctcc ctgaatctcc    6000
tactacaatt tctgttcgtc caccatctgc tgagtaactg acttcattcc gattcagtcc    6060
cactcagcca ttcctgagtt ctaccccaaa cacactcatt aagaattcct agtgaggcat    6120
tttggagtga ggttatgaag ttagaccttg gttctggcac gtctctgagt ctaagtggag    6180
tctttgcaaa gaatttcagg agattctcct attgaagtag ataatgcagg ggcacttggg    6240
tgggtcagtc agttaagtgt ctgactcttg atttcagctc aggtcttgat gtcagggttg    6300
```

```
tgagttcaag ccccacgttg ggctccactt tgggtgtgaa gactactcaa aaataaaata    6360
aagtagataa tgcatttaaa gtgtccgcag ctccctctcc tctccccaga gtttcctctt    6420
gggccatgtt atggatgggc tgcaagaata tccccaagac cttgggagac cagtctccta    6480
gcagtgtcac ttctcagccc tccctcccta ggagatagct ctctttcagg ccatgttgta    6540
tttcctcatc actccaggag tccaggagat tggggaaatg ataggtttga attcagagga    6600
actagagaaa gctttgtgct caaggaccat gaaaacagcc aaagaggagg tggtcactac    6660
actgaacttc acccaggtaa gggccctatg ggaggggggct gattttgaga ctattctgtg    6720
gctgccatcc taaccagctg gctctgccca acaggctcag tatgctcggg atgctctggc    6780
taagaacatc tacagccgcc ttttcaactg gatagtgaat cgaatcaatg agagtatcaa    6840
ggtgagagat tgctctcctc cctcaacact ctcctgtctg cctcactttt cttgtcccgg    6900
tcaccatccc tatacttcgg gttctgagat gaagagagta agaaggatga agggtaaggt    6960
acagttgctt ccaatagtgt gttgttgtgg aagcatctct ggttttgag tttgactgtc    7020 tggatcccct gcttaccagc tgtgtggcct tttagtttca cagagattct gagcctcagt    7080
ttcctgattt ggaaaattgg atgctaatgc ctacctcctt catagtgagg atcagataaa    7140
attatgcaca tggttaccat ataacccaga aattccactc cagatataga tccaagagaa    7200
ttgaaaacag atgttcacgt aaaaacctgt acccaaatgt tcatagaggc attacccata    7260
atagccaaaa agtggaaaca actcaaatgt ccatcagttg atgaatgggt aaataaaagt    7320
ggtatatcca tacaatggga tataaataaa taaacaggcc ataaaaagga atgaagtact    7380
gatacatgct caacacagac aaatcgtgaa aacattcaag tggaagcagc cagacacaaa    7440
aggtgattcc atttatatga aatgtaatag gcaaatctat ggagagggtg gtagattaat    7500
ggttagcagg ggcttggagt ggagggagag gggaaggtgg aatgacagct aatgggtatg    7560
agtacaagat ttctttgggg gatcatgaaa atgctctgga attaggtagt ggtgatggtc    7620
atacactttt tttttttttaa gtttattttg agagagtggg ggaggagcag agagaaagag    7680
gaagagagag agagaatctt aagcagggcc tgtgctgtcg gcgtagagcc tagtgcaggg    7740
cttgaactca tgaactgtga gatcatgacc tgagctaaaa ccaagagttg gacacttacc    7800
cgattgagcc acctaggcac ccccatatgc atttttgaata tactgaaaaa tcactgaatt    7860
gtataccttt aaagggcaaa ttttatagaa tgtgaattag ataaaaatag agctattatt    7920
taaaaaattt tgtgcatgag aggtgcctgg gtggctcagt cggttaagca tccgacttag    7980
gctcagctca tgatctcacg gtttgtgggt tcgagtccca cgtcaggctc tgtgctgtca    8040
gctcggagcc tggaacctgc ttccgattct gtcactccct cttctctgc ccctccccca    8100 cttgcagtct gcctctctct ctcaaaaaat aaataaacat taaaaaaaat tttttttaat    8160
cttgtacatg aaaatgcctt caattcagaa gctactatgg aaaggcaaca ggggaaaatg    8220
ggatttaaaa acgcttagtc cctttgaaat ttgatctgtc catctgtaaa atgaaattaa    8280
tcacaccata tagggttatc atgagattta atgaagtaag aacatagaat tttttctaaa    8340
ttgctctaca aatgtacgag atggttattt tcctcagaag attttaaagt ctttctacct    8400
cgtcccctgg gagcaccatc ctggaatctg cttacatctc cctcccccctc tcctccctct    8460 gcttggcccc tagtgtgtag aggaggaagg agaataaaat cacaactggt caagctcacc    8520
cgagttctgt ttgccctctg ctccaatcac atccgcccca gaagggcctg gcctggtgtg    8580 cagaggggc ccgtcctcag atttatcttt ccctcctctt caggtgggca gcggggagaa    8640
aaagaaggta atgggggtcc tggatatcta cggctttgaa attttaaagg tgagagagct    8700
```

```
tcccccaacc gcagccaccc tgcatcccta gggttggggt gcggaggctc aaagggaggg    8760
gcttgcgaga ggggaggcgt ggggctgaga gggaggaagg gtcttggact gagctgctct    8820
ctctctaacc tgggtcccct ccttcaggac aatagctttg agcagtttgt gatcaactac    8880
tgcaatgaga agctgcagca ggtgttcatc gagatgacgc tgaaagagga gcaggaggaa    8940
tataagagag aggtgcgcgg agccttcccc cacagcccct ctccaaagtg acgctggtgt    9000
gcgcgccacg tctgtctttc tcctcaatcc cggtttcctc tcactcgtgc ccagatggga    9060
acacaaagga caaaaagttc ccctttcact gctcaacagt gcagcattac caagaagccc    9120 tagttttgc tctccacccc ccagtcccct gctcccaccc caggccgtgc cagcaagggg      9180
cagactgatg gaaggctgtg tggggggagt cctcacaagg gtgaagtgac agctgtgcgt    9240
ggcctgcagc acactgtgag cctgatttag aagggacatt tctcccaggc ttgtcacccc    9300
accacatcca ttttggtgct cttctctgac acctcacaat tctttgtctc ctcgggccct    9360
ggctgatgtc accatctcct cgtgtagcac cctgatccca gacttcctcc ccagaagttc    9420
cccatggctc aacatttcca cactccttcc cctgttcagc aagaaggctt gctttctatg    9480
gctaggtgtt agaaaagcta tctgattgag ctaattcccc ccaaagtgtg aatggctgag    9540
agtctcactc atcaaaacgc tgccagggat gctgcctgtg agcccttggg aatctgctgc    9600
agcagaattt cagacaatgt ggtcacaatg tgtgggaaag gttttttta agttgttttt      9660 catgttttta tcttaaaatt ttaaatgatc aactagagaa tacattccca tgcctcaaaa    9720
ttcaaaaagc ttaaaaaggc atataaagaa agggctctct cccagcctat ccccagcctc    9780
ttagttctcc aaccatctag aggcaactaa agtggccctc ttttcagagg tcttttatgt    9840
gtaatcaggc aaatgtagaa gtttattttc ccacagaatt ttttcaaat ggcagtgaat      9900 atgctctgct ctaccccttg ctttcatcaa ttaatgagat cttttccatat cgtatataaa   9960 gatgcatctt tacagctaca cagggttgta aggatatcat acttcattta actagttggg   10020
gaaagtattt tggggatgaa atgggaaggc aactacttaa ttccactcta cattccctga   10080
agatctgtga gggggtggga gagtgttccc cagccacacc cccacacctg ggaatggtct   10140
gagtctggga gggctggccc ttgggtggga tcagaagcta tcctgtctgc ggctacccct   10200
aagtggggaa cgattgtctt tgggtctcct tctgtaccat tcttgcttaa aacaaaaaca   10260
aaaacaaaaa caaaaactat acagtcccag agtatcaggt agattagtag ttcttaaagt   10320
gtggtcctgg accagcagca tccctggaaa ggtgttagaa agacagattc ctaggctcta   10380
tcccagacat gctgaatcag aaaccctggg gatgggcct agcagtctgt ttttacaagc     10440
cctctagctg actgccatgc aagtttgaaa agcactgatg taggtctttg aagatgtatc   10500
aagttaggtt tgttgcttga tgaaattcac tcatgtgctt tggttttatt ggtcgttgcc   10560
agaacagtgt ggcctttgct cttgcacacg ctcaaggatc cttcctcact ccacagtggg   10620
gcaatcccta ccccgatctt caccccacac cacctacagg gctctcttca gcatctcccc   10680
ctctctcaca gctgctctgg gtcctttcac gtgtctccca cccacaaat tctccatcaa     10740 cctggagggga tgggaaccta aacagaagcc acaccaagga cccctcttaa ttatagggct   10800
ttctgagtcc ttcttgggtt gggtgagagg gagcctgagt ctggtgaggt ctttggagac   10860
ttgtcctgga cctgctcttg taacctgtca tgcctcttct tgccagggca taccgtggac   10920
aaaggtggac tactttgata atggcattat ctgtaacctc attgagcacg tgagttatct   10980
ttatgttatc tctgagacct cttgcagact gactgaatat ccttgtcctt cccctctccc   11040
```

```
ttgccccact tggtaaggat ggtgaagtgg gcaaaggatg aagggcaga gggacagcag    11100 tgaggatgtg gacatcttgg aggatcaggt ctaagttggg ctgatcttgt tccccctgacc   11160 agaatcagca aggcatcctg gccatgctgg atgaggagtg cctacggcct ggggtggtca    11220
gtgactccac cttcctagcg aagctgaacc aggtcttctc caagcatggt ttctatgaga    11280
gcaaagtcac ccagaatgcc cagcgccagt atgaccacac catgggcctc agctgctttc    11340
gcatctgcca ctatgcgggc aaggtgacat gcagggctgg agggtagaaa tgggcctggg    11400
catgggtgga aggcaatggg ggaggacctg cggggagatg agatctggga atacttcaca    11460
atgagattgg gagtgccaag tgctgggaca aggtcatgga ccctccagac ccatagctat    11520
tcctctacag gtgacttaca acgtgaacgg cttcattgat aagaacaatg acctactctt    11580 ccggacttg tcccaggcca tgtggaaggc ccagcacccc ctccttcagt ccttgttccc     11640
tgaaggagtt cccacacaga catctctcaa gcgcccccca actgctggag cccaattcaa    11700
gagttctgtg gccatactca tgaagaactt atattccaaa aaccccaact acatcaggtg    11760
acatgctggg tacatgggga aatgcagcat atgtgatggc agatgcaggg tccagcacta    11820
tagaacctgt ccattgttgg ggggagggt gtctctggaa taagagtatc agaaggccct     11880
tccctcataa aaaatgagga actgagaatc ctgtggcagg gagagcatca gactttagta    11940
ggaaccacgc tatagtgagt gaagctggga aggccagtgt gttcacttcc tctgaaaata    12000
accctccaga ataggggttat agagaccagg atgggtcaca cttgcaaagg tgaagctcct   12060
catgcctgtg ccttgcacct ctcccccac cccaaggtgt ataaagccca atgagcatca     12120
gcagcgaggt cagttctcgt cagagctggt ggccgtccag actcggtacc tgggactgct    12180
agagaacgtg cgggtgcgtc gggcgggcta tgcctaccgc cagaggtatg ggcccttcct    12240
ggaaaggtac cgattgttgg ggcggagcac gtggcctcgc tggaatgggg gagacaggta    12300
agactcctgg gggagatggg ggagcaggga aagggcagtgc agggaacatc tgggtggtgg   12360
gaagaacaga cagtgccatg taaattgcca aaactccatg aatggatact tggggaaatg    12420
aactgatcac tttgcagagg ctctgaagtc tgttcaagcc ctgaactcct ctccctgggt    12480
ataagaggtt ggggaaaggt gaaagaggat ccttctctgg gatgcccctt ggtagctttc    12540
cccatctgct cctgtaggga gggagttgag aaggtcctgg gggagctgag cttgtcctca    12600
gaggagctgg cctttgggaa gacaaagatc ttcatcagaa gccctaagac tgtgagttgg    12660
agggtgcact tgtgtttggt tggggtagga ggcagaagag ttggagggtc catgagtgag    12720
aggctggggc ggaggggagc atctataact tgggatggat ggtgggtgag gaagtctgct    12780
ttctgcaggg actttgtccc tggaaactga atccttgggc tcctaccca ccctgcttgc     12840 atggcccact ctgagtgcct ctacctgtag cagaactcct gaagatcaag gtgatgtgcc    12900
actcatgtct aaatttccag acctcgcacg tgcctctgac agagttagaa ttcagtaggt    12960
ttctgttaag gtgaataaca cttaacagaa taataatgag tgagcgaata aacgaatgca    13020
ctaagaagtc aatggaatga ataaaacact ggctgggaag cccctggcac ctgggctccg    13080
ggaggagaga gtgctattcc cctaggccag cctttccgcc ccaccttcca cctctccaca    13140
gctgttctac ctggaagaga agcggcgcct gagactgcag cagctggcca cgctcattca    13200
gaagatctac cggggctggc gctgccgcat ccactaccag ctgatgcgca agagtcagat    13260 cctcattttcc tcctggtttc gaggcaacat ggtatcagtt gctccctaaa gtcccatccc   13320
tttcactcca ataaaagagt cggggcacc tgggtggcac agtcggttaa gcatccaact    13380
cttgatttca gctcaagtca tgatctcctg gtttgtgaga tcaagcccta cgttgggctc    13440
```

```
tgtgctaaca gtgtggagtc tgcttgggat tctctctctc tgtctccgtc tctgtctctc    13500
aaaataaata aacatttaaa aaagagagag ggagagagtg ggaagtagga gaggtggttc    13560
aggggatgga gttttttctaa caggcctatt gttttttctgc agcaaaggaa gcgctatgcg   13620
aagataaagg catcagtggt gctgatccag gcttttgtga gaggggtggaa ggtaatgcgg   13680 aaggggagag gggtttcctc cgcacacatg gggtcttccc ccacatggtt tctcctggat    13740
tgtgccagct gctgggagga aagagtagca gaaagcaagt cctgcccaca cccagggcat    13800
acctctgtgt gatggcatgc ctgcatctgg gtgtgtgtct gggagtgtgg gtgcgtactg    13860
gggagatgtg tgtagacacc tgggtgtgtc cctgacttgg cttttgagtgc cttcctcatt    13920 gccagcttgt ctgcctttac tttctccctc cagtagagtc tcggcactttt atctaactgt   13980 gctctttgta tggttggaaa acagtagaac ctctgtctcc ttatcttcta ggtctgtcta    14040
tctttacttt ggctcctttc tcatgtatcc cttctaggcc cgcaaggatt atcgaaaata    14100
cttccggtcg gggggctgccc tcaccttggc agatttcatc tataagagca tggtaagtgg   14160
tcttacttac tatgggggtt gagggtggaa ggtggagggg aggttgtgga gggagggtca    14220
ggtttggaaa aggaagatga ggggtttgag aagaggtgat caaagttttc cctggaaggg    14280
tttctttgat ctgcatgtac ttaattatta agtcctaggg taagaaggaa tggggctttg    14340
gtgcctcagg gcccaggggc agaatcagag tgcactctgg aaggagtgga cactgtgggc   14400
aaccttgggg caggaagggg tcccagcaca cccactgact ggcccatgat gaataggccc    14460
gagaagagac gggctggatg gctaacaaca gtttaaagag actgagcctc atgaaagagc   14520
agagtgagga catagggtta cctaacttaa ccttccgaga tccattttat ggtaggggtg    14580
aaagtggagg gattgtatct ttcttttcggc tcttctgaag ctatagcaag caagtccaca   14640
atgaaatctc aggaaatatc ttaattctgg aggacttggg actttttttt ttttttttgaa   14700 cttttatttta tcattttcga gagacagaaa gagacagagc acaagcaggg aaggggcaga   14760
gagggagaca cagaatcgga agcaggctcc aggctctatc agcacagagc ccaacgcaga   14820
gctcaaaccc atggaatgtg agaccatgac ctgagctgaa gtcagacact taactgactg    14880
agccacccag gtgatctgac cccagagttt taatgcctgc cgaagactgc ttccccacac    14940
tgtcccccca ctcccctag agacctactg gggcaggagg gctatatagg gaaaggaaag     15000
actttctaga tctagaaaaa acaaacaatt aagaaaacct tcagagtttc gacatcagtt    15060
agcacatgag ggattggagg aaatgcttag gaatgtttat tgaattaaat caaactagac    15120
ctgaccaagt ccccttgggg acttaaacca aggtgtgagg tgattagacc aagcctgcaa    15180
gatctttgta gcagaggaat caaagagctt ggatagttcc tggagaatta tagcaatata    15240
ctgcataccc tccctttttcc cattttaatt tttttaacct aatgtgttag taagaagttt    15300
tcataaaaat tccaaaaact tggggggcgca tgggtggctc agtcagttaa gtgtctgact   15360
cttgattttg gcttaggtca cgatctcaca gtttgtgagt tcgagcccca catcaggctc    15420
catgctgaca gtgctaagcc tgcttggaat tctctctctc tcccctctctt tctgctcctc    15480 ccccacttgc tccctctctc tctctctctc aaaataaaat aaacttaaaa aaaaaaatcc   15540
aaaacttgga agtactcaag atcaagctat tttctatacc ttcaataatt ctaccccaca    15600
aacaaacagg gtgctgggtg ttccctggga tataaagact ggagagtcct tattctagat    15660
tgggggagac taaacagatg ccatgggtga tacttgatct gatcctggaa caggaagaat    15720
aagaacaaag ctacaaaggg cattttttaga agtttataaa ggacattagg agaaatttga   15780
```

```
gcatgcattg ctgttggatg agtgtatcca attaatgttt gtcttcttag gtatggaggt    15840
ggaattatga tttgtgtagg agaatgtcct ggttcttggg agatgtgtgc ttaagttttg    15900
ggggaaaatg ccatgatttc tctaacctac tttaggatga tatggtagca aagatttata    15960
tatgtgtgag tgtgtgtatg tatttattta tgcccatttg tatacatgtg tgcatgtgtt    16020
agaaagcctg caaatatggc caattgttaa cattatcagt tggtggattt aggtaaggaa    16080
tatgtggcat gcagatattc actgtaatgt ttcttcaact tttatgtaag tttaaaaact    16140
ttcaatataa gacagtaagt tatatgaaat aaaaaagaac gtaaggcaga ttatgtcact    16200
cttcccctta aaatcctcta atggcattcc atttgactcc caataaaagc cagtgttctt    16260
acctcagcct acaaggccct tcacgaatgt acttgaccaa ccagtcctct gatcttcttt    16320
cttcttgctc gatttaatcc agtctcactt tcttttcatt tctgggatat gctactgctc    16380
atttctggtc tcagggccag cttttttgca tcatagcata tataattatc tgcaattatt    16440
tgcatcatag catatataat taacatatat tatatatgtt tgtttgctgt ggggttcttc    16500
cctcccccgg tagaatataa gctcagtgag aatagagatt ttgtttgttc tgttcactgc    16560
tgtgtatcca tacctagaac agtgccaggc acagagcaga cactcaataa atgttgttga    16620
atggcagggg aaaaaaaaca acaacaacaa gaactcagct tgggatccag actcccaagg    16680
actcattgtc tagaagaggg aaaagatttc cacacagata atagtagtac aaacacagaa    16740
gtatagacaa agtgctgtgg ggcttcaaag aaaggagagg cagccctggc ccagggaatc    16800
agggagggct tcgagctgtg tctgaaagga taggtagaat ctagatgggc acagctgagt    16860
tgagagcagg atgggctgag gcaccgagtg atcacgcctg ggctaggcag agggcttgat    16920
gaggaacact acctgagagg tgtgctggga tcatgcaggg gatcctgggg catgagattg    16980
ggccctaaat agaagacttt gaatgccagg ttgaggcatt gggcttgacc gatcagggaa    17040 gggggggaggt ttggtacctg tcctatagcc aatgcagaca gtggcagcca gctgtaggca    17100
gctatgaact gagacaatag gaagtcacag gagcaaaata ctgaggccag ttttcatctt    17160
ggttgctttc acctcactac cctgggcagc aggtctctgc ttggaactaa cccttccttc    17220
cctccctccc agtctcctgt tcacgctctc actgcccagc ctccagtgaa cactggaccc    17280
acaagagatc caggaggtga ctcccttctg actcctcgct ctacttgttg cttcttactc    17340
tgggtggcct ccctccttc aggtggcagg tcctggatga gagtttgcct gttgggaggt    17400
ctgtcttctc atccgtccac tcccaatccc cctgcttcca atctagacgc agaagttcct    17460
gctggggctg aggaacaatt tgccgtctac caacatcctg gacagaacgt ggccagcggc    17520
cccttacaga tgcttcaaca cagcaaacca ggagctacag cagctcttct accgctggaa    17580
ggtgagtggg gccagcacg actcctctca tttgtctttt tttcctcctc cctctgattt    17640
tcatcttctg cctccttctt ccactttttt tcttcatggt gaaaacaaca tagatcacaa    17700
aattggccat cttaaccatt tgtaagtccg gtgtcataaa gcacgttcac actattgtgc    17760
agccgtcacc accatccgtc tctgtatttc tttttttatca gcccaaactg caatcctgta    17820
cacattaagc agtaactccc cattccccac tcttgtagcc cctgggactt ataatcgact    17880
ttctctgtga atttgactgt tctcggtacc tcatggaagt agaatcatac atttgtcctt    17940
ttctatctgg cttatttcac tcagcacagt gtgcttccat tcaggaaata tgtaccgagc    18000
acctgtctag agtaggcctt gtgctgtgtg ctggcatata gccctcctcc tgggtctgac    18060
acatttgatt gtttccatcc ccctctccca gagtcccttt gaggggggggc agtgctcctc    18120 cagcagctgc cctctctgaa gtgcctagag cctattctat tccctgtctc tcctcttttc    18180
```

```
cagcccctgc cctccttcca cctctcagtg ttctcccaaa cccccacccc aggcctgcct    18240
tctgcctcca cgagcttagc ccctgccect cectctcaca gtgcaagaga ttccgggatc    18300
gactgtcccc aaagcaggta gagatcctga aggagaagct ctgtgccagt gaactgttca    18360
agggcaagaa ggcttcctac ccccagaggt gagggcccccg cagaccctgc acagtcagtt    18420
tcatccagag caaagacagg atccccagg tgggataggg cagtggtccc caaactagtg     18480
tgcatcagca ccacttggca ggcttgatga cacccagatg gctgcaccac cccccgccca    18540
gagtttctga ttcagcagat ctggggctgg ggcccaataa tttgccttc taacaagttc     18600 tcaggggatg ctgatgttgg tcctggacca tgctgagata gaggatatgg tggagcatgg    18660
gggaagggac atgggaactc actgtgggga ggctcagggc cttggggtc agtggtgagg     18720 aacttgtctc caccacatac ctcctgtgtg tcttcagtgt ccccattcca ttctgcggtg    18780
actaccttgg gctgcaaggg aaccccaagc tgcagaagct gaagggcggg gaggaagggc    18840
ctgttctgat ggcagacact gtgaagaagg tcaatcgtgg caatggcaag gtgaatgcct    18900
gcaccctgga cttctgccca cggccggatc cagagccttg ggactggtag ctggaagggt    18960
ggggttaatc ttcacctttc ctcacatttt cctcttctgt ccttagactt cctctcgaat    19020
tcttctcttg accaaggggc atgtgattct catagacacc aagaagtccc aggccaaaac    19080
cgtcattgga ctagatagtg tggccgaggt gtcagtcacc agcttcaagg atgggctttt    19140
cagcttgcat ctgaatgagg tatcagagct ctgtgggtgc agtacctcac gctggagaag    19200
gtggtgggca tcacggggct ggggtgggct ggaggtgatg aggaccagac ctctcactct    19260
gggccttcag tgcctctcag gctgctcctg cagagggaaa aatgaatccc ttccccactt    19320
tttccccctt cctaagatat catcagtggg ctccagggg gacttcctgc tggtcagcga    19380
acatgtgatt gaactgctaa ccaaaatgta ccaggctgtg ctggatgcca cacagaggca    19440
gcttctaatc tccgtgactg agaagtaagg ccatgagctg ggggtgaggg ccagcctggg    19500
ggcagatgac caagctgttg gtcattgtga ccgggaaaat tcatgtagtc agaaagtgaa    19560
gcatattctg tcaaggcaag gtttggaggt gtttcttagt ctccccactc aggttctctg    19620
gggccctgaa tcttctgaca cgaggggagg agagatgtac ttcctttaag aaggagaatg    19680
gaaaccatca tgaaagtatg ggagtagaga tgagaggatg agggtaccag cttaccccct    19740
ctgtctgttt cccctccagg ttctcagtga ggttcaagga gagtagtgtg gctgtcaagg    19800
tcatccaggg ccctgagggt gataggaacg gcaagctaaa atgcaagaag aaagggagcc    19860
gttgcctgga agtgactgta tagtgaagag gtgggggcct gatgcagaga cagcagcttc    19920
tctggacccg tgccaacccc acccaccat gtttgcagga ggatctgatc gtggtgtggg    19980
gctcagagat tgaggaaccc ttgaagagga cctttcttct cccaaactct ctgggcccc    20040 tctcccttag aacttatcct cccaccctca gctgctttgc ccactaataa aacaagtgac    20100
ttcccaaata                                                          20110
```

<210> SEQ ID NO 6
<211> LENGTH: 1042
<212> TYPE: PRT
<213> ORGANISM: Felis catus

<400> SEQUENCE: 6

Met Thr Leu Met Glu Asp Ser Val Gly Val Gly Asp Leu Val Leu Leu
1               5                   10                  15

Glu Pro Leu Glu Glu Glu Pro Leu Leu Lys Asn Leu Gln Leu Arg Tyr

-continued

```
                20                  25                  30
Glu Asn Lys Glu Ile Tyr Thr Tyr Ile Gly Asn Val Leu Ile Ser Met
             35                  40                  45
Asn Pro Tyr Gln Gln Leu Pro Ile Tyr Gly Pro Glu Phe Ile Ala Lys
 50                  55                  60
Tyr Arg Asp Tyr Thr Phe Tyr Glu Leu Lys Pro His Ile Tyr Ala Leu
 65                  70                  75                  80
Ala Asn Val Ala Tyr Gln Ser Leu Arg Asp Arg Asp Arg Asp Gln Cys
                 85                  90                  95
Ile Leu Ile Thr Gly Glu Ser Gly Ala Gly Lys Thr Glu Ala Ser Lys
                100                 105                 110
Leu Val Met Ser Tyr Val Ala Ala Val Cys Gly Lys Gly Glu Gln Val
                115                 120                 125
Asn Ser Val Lys Glu Gln Leu Leu Gln Ser Asn Pro Val Leu Glu Ala
130                 135                 140
Phe Gly Asn Ala Lys Thr Ile Arg Asn Asn Ser Ser Arg Phe Gly
145                 150                 155                 160
Lys Tyr Met Asp Ile Glu Phe Asp Phe Lys Gly Ser Pro Leu Gly Gly
                165                 170                 175
Val Ile Thr Asn Tyr Leu Leu Glu Lys Ser Arg Val Val Lys Gln Leu
                180                 185                 190
Glu Gly Glu Arg Asn Phe His Ile Phe Tyr Gln Leu Leu Ala Gly Ala
                195                 200                 205
Asp Ala His Leu Leu Glu Ala Leu Lys Leu Glu Arg Asp Thr Ser His
                210                 215                 220
Tyr Ala Tyr Leu Asn Gln Lys Val Ser Arg Val Asp Gly Met Asp Asp
225                 230                 235                 240
Ala Ser Asn Phe Lys Ser Val Gln Asn Ala Met Thr Val Ile Gly Phe
                245                 250                 255
Ser Glu Val Glu Ile Gln Gln Val Leu Glu Val Thr Ala Leu Val Leu
                260                 265                 270
Lys Leu Gly Asn Val Glu Leu Ala Asp Glu Ser Gln Ala Asn Gly Thr
                275                 280                 285
Ser Ala Ser Gly Ile Arg Asp Gly Arg Gly Val Gln Glu Ile Gly Glu
                290                 295                 300
Met Ile Gly Leu Asn Ser Glu Glu Leu Glu Lys Ala Leu Cys Ser Arg
305                 310                 315                 320
Thr Met Lys Thr Ala Lys Glu Glu Val Val Thr Thr Leu Asn Phe Thr
                325                 330                 335
Gln Ala Gln Tyr Ala Arg Asp Ala Leu Ala Lys Asn Ile Tyr Ser Arg
                340                 345                 350
Leu Phe Asn Trp Ile Val Asn Arg Ile Asn Glu Ser Ile Lys Val Gly
                355                 360                 365
Ser Gly Glu Lys Lys Val Met Gly Val Leu Asp Ile Tyr Gly Phe
                370                 375                 380
Glu Ile Leu Lys Asp Asn Ser Phe Glu Gln Phe Val Ile Asn Tyr Cys
385                 390                 395                 400
Asn Glu Lys Leu Gln Gln Val Phe Ile Glu Met Thr Leu Lys Glu Glu
                405                 410                 415
Gln Glu Glu Tyr Lys Arg Glu Gly Ile Pro Trp Thr Lys Val Asp Tyr
                420                 425                 430
Phe Asp Asn Gly Ile Ile Cys Asn Leu Ile Glu His Asn Gln Gln Gly
                435                 440                 445
```

```
Ile Leu Ala Met Leu Asp Glu Glu Cys Leu Arg Pro Gly Val Val Ser
    450                 455                 460
Asp Ser Thr Phe Leu Ala Lys Leu Asn Gln Val Phe Ser Lys His Gly
465                 470                 475                 480
Phe Tyr Glu Ser Lys Val Thr Gln Asn Ala Gln Arg Gln Tyr Asp His
                485                 490                 495
Thr Met Gly Leu Ser Cys Phe Arg Ile Cys His Tyr Ala Gly Lys Val
                500                 505                 510
Thr Tyr Asn Val Asn Gly Phe Ile Asp Lys Asn Asn Asp Leu Leu Phe
                515                 520                 525
Arg Asp Leu Ser Gln Ala Met Trp Lys Ala Gln His Pro Leu Leu Gln
    530                 535                 540
Ser Leu Phe Pro Glu Gly Val Pro Thr Gln Thr Ser Leu Lys Arg Pro
545                 550                 555                 560
Pro Thr Ala Gly Ala Gln Phe Lys Ser Val Ala Ile Leu Met Lys
                565                 570                 575
Asn Leu Tyr Ser Lys Asn Pro Asn Tyr Ile Arg Cys Ile Lys Pro Asn
                580                 585                 590
Glu His Gln Gln Arg Gly Gln Phe Ser Ser Leu Val Ala Val Gln
    595                 600                 605
Thr Arg Tyr Leu Gly Leu Leu Glu Asn Val Arg Val Arg Arg Ala Gly
    610                 615                 620
Tyr Ala Tyr Arg Gln Arg Tyr Gly Pro Phe Leu Glu Arg Tyr Arg Leu
625                 630                 635                 640
Leu Gly Arg Ser Thr Trp Pro Arg Trp Asn Gly Gly Asp Arg Glu Gly
                645                 650                 655
Val Glu Lys Val Leu Gly Glu Leu Ser Leu Ser Ser Glu Glu Leu Ala
                660                 665                 670
Phe Gly Lys Thr Lys Ile Phe Ile Arg Ser Pro Lys Thr Leu Phe Tyr
                675                 680                 685
Leu Glu Glu Lys Arg Arg Leu Arg Leu Gln Gln Leu Ala Thr Leu Ile
    690                 695                 700
Gln Lys Ile Tyr Arg Gly Trp Arg Cys Arg Ile His Tyr Gln Leu Met
705                 710                 715                 720
Arg Lys Ser Gln Ile Leu Ile Ser Ser Trp Phe Arg Gly Asn Met Gln
                725                 730                 735
Arg Lys Arg Tyr Ala Lys Ile Lys Ala Ser Val Val Leu Ile Gln Ala
                740                 745                 750
Phe Val Arg Gly Trp Lys Ala Arg Lys Asp Tyr Arg Lys Tyr Phe Arg
                755                 760                 765
Ser Gly Ala Ala Leu Thr Leu Ala Asp Phe Ile Tyr Lys Ser Met Thr
    770                 775                 780
Gln Lys Phe Leu Leu Gly Leu Arg Asn Asn Leu Pro Ser Thr Asn Ile
785                 790                 795                 800
Leu Asp Arg Thr Trp Pro Ala Ala Pro Tyr Arg Cys Phe Asn Thr Ala
                805                 810                 815
Asn Gln Glu Leu Gln Gln Leu Phe Tyr Arg Trp Lys Cys Lys Arg Phe
                820                 825                 830
Arg Asp Arg Leu Ser Pro Lys Gln Val Glu Ile Leu Lys Glu Lys Leu
                835                 840                 845
Cys Ala Ser Glu Leu Phe Lys Gly Lys Lys Ala Ser Tyr Pro Gln Ser
    850                 855                 860
```

Val Pro Ile Pro Phe Cys Gly Asp Tyr Leu Gly Leu Gln Gly Asn Pro
865                 870                 875                 880

Lys Leu Gln Lys Leu Lys Gly Glu Glu Gly Pro Val Leu Met Ala
                885                 890                 895

Asp Thr Val Lys Lys Val Asn Arg Gly Asn Gly Lys Thr Ser Ser Arg
                900                 905                 910

Ile Leu Leu Leu Thr Lys Gly His Val Ile Leu Ile Asp Thr Lys Lys
            915                 920                 925

Ser Gln Ala Lys Thr Val Ile Gly Leu Asp Ser Val Ala Glu Val Ser
        930                 935                 940

Val Thr Ser Phe Lys Asp Gly Leu Phe Ser Leu His Leu Asn Glu Ile
945                 950                 955                 960

Ser Ser Val Gly Ser Arg Gly Asp Phe Leu Leu Val Ser Glu His Val
                965                 970                 975

Ile Glu Leu Leu Thr Lys Met Tyr Gln Ala Val Leu Asp Ala Thr Gln
                980                 985                 990

Arg Gln Leu Leu Ile Ser Val Thr Glu Lys Phe Ser Val Arg Phe Lys
            995                 1000                1005

Glu Ser Ser Val Ala Val Lys Val Ile Gln Gly Pro Glu Gly Asp
    1010                1015                1020

Arg Asn Gly Lys Leu Lys Cys Lys Lys Lys Gly Ser Arg Cys Leu
    1025                1030                1035

Glu Val Thr Val
    1040

<210> SEQ ID NO 7
<211> LENGTH: 21
<212> TYPE: DNA
<213> ORGANISM: Artificial Sequence
<220> FEATURE:
<223> OTHER INFORMATION: Myo1a F1 primer

<400> SEQUENCE: 7
gaaaatactt ccggtcaggt g                                              21

<210> SEQ ID NO 8
<211> LENGTH: 22
<212> TYPE: DNA
<213> ORGANISM: Artificial Sequence
<220> FEATURE:
<223> OTHER INFORMATION: Myo1a R1 primer

<400> SEQUENCE: 8
caagggttct tcatctctga gt                                             22

<210> SEQ ID NO 9
<211> LENGTH: 22
<212> TYPE: DNA
<213> ORGANISM: Artificial Sequence
<220> FEATURE:
<223> OTHER INFORMATION: Myo1a F2 primer

<400> SEQUENCE: 9
taccagtgga agtgcaagaa gt                                             22

<210> SEQ ID NO 10
<211> LENGTH: 42
<212> TYPE: DNA
<213> ORGANISM: Artificial Sequence
<220> FEATURE:
<223> OTHER INFORMATION: Myo1a R2+T7 primer -continued

```
<400> SEQUENCE: 10
taatacgact cactataggg acactacgaa gttctgctcc ag          42

<210> SEQ ID NO 11
<211> LENGTH: 21
<212> TYPE: DNA
<213> ORGANISM: Artificial Sequence
<220> FEATURE:
<223> OTHER INFORMATION: Gabra2 F1/F2 primer

<400> SEQUENCE: 11
acttggttac ttttgggctg t                                 21

<210> SEQ ID NO 12
<211> LENGTH: 22
<212> TYPE: DNA
<213> ORGANISM: Artificial Sequence
<220> FEATURE:
<223> OTHER INFORMATION: Gabra2 R1 primer

<400> SEQUENCE: 12
tgattgaagt gagctgaaag gt                                22

<210> SEQ ID NO 13
<211> LENGTH: 42
<212> TYPE: DNA
<213> ORGANISM: Artificial Sequence
<220> FEATURE:
<223> OTHER INFORMATION: Gabra2 R2+T7 primer

<400> SEQUENCE: 13
taatacgact cactataggg aacatccttt catggtgact ca          42

<210> SEQ ID NO 14
<211> LENGTH: 20
<212> TYPE: DNA
<213> ORGANISM: Artificial Sequence
<220> FEATURE:
<223> OTHER INFORMATION: TrkB-F1 primer

<400> SEQUENCE: 14
ctgagagggc cagtcacttc                                   20

<210> SEQ ID NO 15
<211> LENGTH: 20
<212> TYPE: DNA
<213> ORGANISM: Artificial Sequence
<220> FEATURE:
<223> OTHER INFORMATION: TrkB-R1 primer

<400> SEQUENCE: 15
catggcaggt caacaagcta                                   20

<210> SEQ ID NO 16
<211> LENGTH: 20
<212> TYPE: DNA
<213> ORGANISM: Artificial Sequence
<220> FEATURE:
<223> OTHER INFORMATION: TrkB-F2 primer

<400> SEQUENCE: 16
cagtgggtct cagcacagaa                                   20

<210> SEQ ID NO 17
```

<211> LENGTH: 40
<212> TYPE: DNA
<213> ORGANISM: Artificial Sequence
<220> FEATURE:
<223> OTHER INFORMATION: TrkB-R2+T7 primer

<400> SEQUENCE: 17
taatacgact cactataggg ctaggaccag gatggctctg                        40

<210> SEQ ID NO 18
<211> LENGTH: 20
<212> TYPE: DNA
<213> ORGANISM: Artificial Sequence
<220> FEATURE:
<223> OTHER INFORMATION: Myo1a F primer

<400> SEQUENCE: 18
ctacgagcag cttcccatct                                              20

<210> SEQ ID NO 19
<211> LENGTH: 20
<212> TYPE: DNA
<213> ORGANISM: Artificial Sequence
<220> FEATURE:
<223> OTHER INFORMATION: Myo1a R primer

<400> SEQUENCE: 19
ccacatttgc caaagcatag                                              20

<210> SEQ ID NO 20
<211> LENGTH: 20
<212> TYPE: DNA
<213> ORGANISM: Artificial Sequence
<220> FEATURE:
<223> OTHER INFORMATION: Gabra2 F primer

<400> SEQUENCE: 20
acaaaaagag gatgggcttg                                              20

<210> SEQ ID NO 21
<211> LENGTH: 20
<212> TYPE: DNA
<213> ORGANISM: Artificial Sequence
<220> FEATURE:
<223> OTHER INFORMATION: Gabra2 R primer

<400> SEQUENCE: 21
tcatgacgga gcctttctct                                              20

<210> SEQ ID NO 22
<211> LENGTH: 18
<212> TYPE: DNA
<213> ORGANISM: Artificial Sequence
<220> FEATURE:
<223> OTHER INFORMATION: Wdfy1 F primer

<400> SEQUENCE: 22
aaaggccgga cactcctc                                                18

<210> SEQ ID NO 23
<211> LENGTH: 20
<212> TYPE: DNA
<213> ORGANISM: Artificial Sequence
<220> FEATURE:
<223> OTHER INFORMATION: Wdfy1 R primer

<400> SEQUENCE: 23

```
tgagctgcag gtagcacagt                                                    20

<210> SEQ ID NO 24
<211> LENGTH: 18
<212> TYPE: DNA
<213> ORGANISM: Artificial Sequence
<220> FEATURE:
<223> OTHER INFORMATION: Nnt F primer

<400> SEQUENCE: 24
cctggtggca ccttcgta                                                      18

<210> SEQ ID NO 25
<211> LENGTH: 21
<212> TYPE: DNA
<213> ORGANISM: Artificial Sequence
<220> FEATURE:
<223> OTHER INFORMATION: Nnt R primer

<400> SEQUENCE: 25
ctgagcccag gtacatgatt t                                                  21
```

MYO1A FOR PREDICTING CONVERSION OF ACUTE PAIN INTO CHRONIC PAIN AND USE OF MYO1A FOR THERAPY OF PAIN

CROSS-REFERENCE TO RELATED APPLICATION

This application is the U.S. national stage application of International Patent Application No. PCT/EP2017/055354, filed Mar. 7, 2017.

The Sequence Listing for this application is labeled "Seq-List.txt" which was created on Aug. 2, 2018 and is 114 KB. The entire content of the sequence listing is incorporated herein by reference in its entirety.

The present invention relates to the identification of Myo1a as a biomarker of conversion of acute pain into chronic pain, and as a therapeutic target. The invention in particular relates to products and methods for assessing the predisposition of a subject to develop an injury-induced chronic mechanical pain and/or an inflammatory-induced chronic thermal pain, and is particularly suited for mammals, preferably human subjects. The present invention more specifically relates to the assessment of the predisposition of a subject to develop an injury-induced chronic mechanical pain and/or an inflammatory-induced chronic thermal pain using preferably the MYO1A gene as a biomarker. Inventors herein provide binding reagents specific for MYO1A, compositions, devices, kits containing the same and animal model, and further describe their uses for assessing the predisposition of a subject to suffer from chronic pain. The invention also relates to products and methods for diagnosing, preventing, managing or treating chronic pain.

BACKGROUND

Pain is commonly classified into acute and chronic. Acute pain is short lasting and is essential for the maintenance of our physical integrity, whereas chronic pain persists beyond the normal time of healing and adversely impacts on our well-being. Chronic inflammatory or neuropathic pain gives rise to highly debilitating and long lasting sensory abnormalities such as hyperalgesia, allodynia and spontaneous pain (Munro et al., 2009). These symptoms occur as a consequence of aberrantly prolonged sensitization of pain pathways both in the peripheral and central nervous systems, causing either increased facilitation or loss of inhibition in pain-transmitting circuits (Sandkuhler, 2009; Zeilhofer et al., 2012). Diminished spinal inhibition occurs in the setting of inflammation and nerve injury through various mechanisms. These include prostaglandin E2-mediated inhibition of the inhibitory glycine receptor (Ahmadi et al., 2002; Harvey et al., 2004; Muller et al., 2003; Zeilhofer et al., 2012) and brain-derived neurotrophic factor (BDNF)-mediated downregulation of the potassium chloride exporter KCC2 that perturbs chloride homeostasis thus altering GABAergic and glycinergic inhibitory functions (Coull et al., 2005; Coull et al., 2003; Zeilhofer et al., 2012). More recently studies deciphered several micro-circuits involving distinct subsets of spinal cord (SC) excitatory and inhibitory interneurons involved in the control of acute and injury-induced persistent pain (Bourane et al., 2015a; Bourane et al., 2015b; Duan et al., 2014; Foster et al., 2015; Peirs et al., 2015; Petitjean et al., 2015). Together, these data demonstrate that we know a great deal about the molecular and cellular mechanisms that underlie both peripheral and central sensitization that control the onset of injury-induced acute pain. However, our knowledge on the molecular and cellular events that trigger the transition from acute to chronic pain is still limited. For example, it is well-established that acute post-operative pain is followed by persistent pain in about 10 to 50% of individuals after common surgical procedures such as breast and thoracic surgery, leg amputation and coronary arteries bypass (Gilron et al., 2013; Kehlet et al., 2006). How and why only a fraction of these patients develop chronic postsurgical pain (CPSP) is unknown. In the clinic, several risk factors predicting the development of CPSP have been suggested. These include age, sex, and the type of surgery, the preoperative and postoperative assessment of the response of patients to evoked painful stimuli as well as their genetic susceptibility to develop CPSP (Kehlet et al., 2006).

In the light of the lack of information about the development, prevention and treatment of chronic pain, there is a clear need for identifying new biomarkers allowing its adequate management, and for new therapeutic compounds allowing its prevention, attenuation or treatment.

BRIEF DESCRIPTION OF THE INVENTION

Surprisingly, inventors herein demonstrate for the first time that loss of Myo1a or an altered expression thereof is associated to the predisposition of a subject to develop an injury-induced chronic mechanical pain and/or an inflammatory-induced chronic thermal pain.

A first object of the invention thus relates to the use of the DNA or mRNA encoding Myosin IA (Myo1a), preferably the Myo1a gene, or of the Myo1a protein, as a biomarker for assessing the predisposition of a subject to develop an injury-induced chronic mechanical pain and/or an inflammatory-induced chronic thermal pain.

The present invention also relates to an in vitro method of assessing the predisposition of a subject to develop an injury-induced chronic mechanical pain or an inflammatory-induced chronic thermal pain, wherein the method comprises a step of analyzing, typically sequencing, the Myo1a nucleic acid sequence obtained from a biological sample of the subject, the detection of an alteration of the nucleic acid sequence of Myo1a in the subject when compared to the Myo1a wild-type nucleic acid sequence as identified in SEQ ID NO: 1 indicating that the subject is predisposed to develop an injury-induced chronic mechanical pain and/or an inflammatory-induced chronic thermal pain whereas the absence of alteration indicates that the subject is not predisposed to develop an injury-induced chronic mechanical pain and/or an inflammatory-induced chronic thermal pain.

Further objects of the invention relates to the DNA encoding Myo1a, mRNA encoding Myo1a, or an agonist of the Myo1a protein ("Myosin IA") for use for preventing or treating pain, in particular an injury-induced chronic mechanical pain and/or an inflammatory-induced chronic thermal pain, in a subject, to a composition comprising an agonist of the Myo1a protein together with a pharmaceutically acceptable carrier or support, and to uses thereof for preventing or treating pain in a subject, in particular an injury-induced chronic mechanical pain and/or an inflammatory-induced chronic thermal pain.

Also herein described is an in vitro or ex vivo screening method of a Myo1a modulator, comprising determining the ability of a drug candidate to activate or stimulate, or on the contrary to decrease or suppress, Myo1a functional expression and/or biological function, and, if the ability is confirmed, the identification of the drug candidate as a Myo1a agonist (activator), and potentially as a drug candidate for preventing, reducing or treating pain, or on the contrary as a Myo1a antagonist (inhibitor).

Inventors herein reveal the possible use of a Myo1a KO (Myo1a$^{-/-}$) animal model for screening for Myo1a modulators and/or for drugs for preventing, reducing or inhibiting pain.

The invention also relates to kits and devices suitable for implementing the above methods, for example a device comprising at least one complementary nucleic acid that binds all or part of the Myo1a gene or of a Myo1a gene locus immobilized on a support, typically oligonucleotides for sequencing the Myo1a nucleic acid, or a kit for assessing the predisposition of a subject to develop an injury-induced chronic mechanical pain or an inflammatory-induced chronic thermal pain comprising oligonucleotides for sequencing the Myo1a nucleic acid obtained from a biological sample of the subject.

In a particular aspect, the invention relates to the use of a device comprising at least one complementary nucleic acid that binds all or part of the Myo1a gene or of a Myo1a gene locus immobilized on a support for assessing the predisposition of a subject to develop an injury-induced chronic mechanical pain or an inflammatory-induced chronic thermal pain.

In another particular aspect, the invention relates to the use of a kit for assessing the predisposition a subject to develop an injury-induced chronic mechanical pain or an inflammatory-induced chronic thermal pain, wherein the kit comprises oligonucleotides for sequencing the Myo1a nucleic acid obtained from a biological sample of the subject.

In the context of the invention, the subject is any mammalian subject, particularly a human subject.

DETAILED DESCRIPTION OF THE INVENTION

Pain is an unpleasant sensory experience associated with actual or potential tissue damage. Thus, pain is the most common symptom of various injuries and diseases. There exists different classifications of pain, for example nociceptive pain is generally distinguished from inflammatory pain and from pathological pain which is a disease state caused by damage to the nervous system (i.e., neuropathic pain) or by its abnormal function (dysfunctional pain, like in fibromyalgia, irritable bowel syndrome, tension type headache, etc.).

Pain is usually transitory, lasting only until the noxious stimulus is removed or the underlying damage or pathology has healed, but some painful conditions, such as rheumatoid arthritis, peripheral neuropathy, cancer and idiopathic pain (pain that persists after the trauma or pathology has healed, or that arises without any apparent cause), may persist for years. Pain that lasts a long time is called chronic, and pain that resolves quickly is called acute. Traditionally, the distinction between acute and chronic pain has relied upon an arbitrary interval of time from onset; the two most commonly used markers being 3 months and 6 months since the onset of pain (Turk, Okifuji, Pain terms and taxonomies of pain; In: Bonica, Loeser, Chapman, Turk, Butler, Bonica's management of pain. Hagerstwon: Lippincott Williams & Wilkins, 2001), though some theorists and researchers have placed the transition from acute to chronic pain at 12 months (Spanswick, Main, Pain management: an interdisciplinary approach. Edinburgh: Churchill Livingstone, 2000). Others apply acute to pain that lasts less than 30 days, chronic to pain of more than six months duration, and subacute to pain that lasts from one to six months (Thienhaus, Cole, Classification of pain. In: Weiner, Pain management: a practical guide for clinicians. Boca Raton: CRC Press, 2002). A popular alternative definition of chronic pain, involving no arbitrarily fixed durations is "pain that extends beyond the expected period of healing" (Turk, Okifuji, 2001, Pain terms and taxonomies. In Loeser, Butler, Chapman, et al. Bonica's management of pain, Lippincott Williams&Wilkins. ISBN 0-683-30462-3). Chronic pain may be classified as cancer pain or benign (Thienhaus, Cole, 2002, Classification of pain. In Weiner, Pain management: A practical guide for clinicians, American Academy of Pain Management, ISBN 0-8493-0926-3).

Pain sensation is conveyed to the brain by sensory neurons which are also called nociceptors. Nociceptors are considered as polymodal since they may respond to multiple forms of noxious or intense stimuli, such as thermal (heat/cold), mechanical, and chemical stimuli. Sensory afferent fibers of nociceptors are heterogeneous in many aspects. For example, sensory nerves are classified as A$\alpha$, -$\beta$, -$\delta$ and C-fibers according to their diameter and degree of myelination. Then, sensory inputs from the periphery are processed and conveyed to higher brain regions by complex circuits involving excitatory and inhibitory interneurons within the spinal cord (Basbaum et al., 2009; Todd, 2010). The balance between excitation and inhibition is crucial for maintenance of normal sensory function, and dysfunction of these circuits leads to the development of pain such as inflammatory and neuropathic pain.

Treatment of pain includes the use of local anesthetics, which block neuronal transmission and affect sensation as well as pain, and analgesics, which relieve pain and additionally may interfere with the activity of chemical mediators of inflammation. Acute pain is usually managed with medications such as analgesics and anesthetics. Management of chronic pain, however, is much more difficult. In addition, inadequate treatment of pain is widespread throughout surgical wards, intensive care units, accident and emergency departments, in general practice, in the management of all forms of chronic pain including cancer pain, and in end of life care. This neglect is extended to all ages, from neonates to the frail elderly. Improved treatments of pain are up to date still highly requested by patients in particular when considering neuropathic, inflammatory and/or chronic pains for which treatment remains incomplete whatever the selected known analgesic molecule.

The purpose of the present invention is to distinguish between subjects those who are prone to develop chronic pain in order to help the practitioner optimizing pain treatment for them.

In the context of the present invention, the patient or subject is an animal, preferably a vertebrate, typically a mammal. In a preferred embodiment, the mammal is a human being, whatever its age or sex. The mammal may further be an animal, in particular a domestic or breeding animal, in particular a horse, a dog, a cat, etc.

Inventors herein demonstrate that in Myo1a KO mice, a short lasting and reversible inflammatory, neuropathic and post-operative pain is converted into an irreversible chronic pain, indicating that loss of Myo1a predisposes the mice to develop chronic pain regardless the etiology of the incurred lesion. Using behavioral pharmacology, they found that Myo1a KO mice were selectively insensitive to the analgesic effects of the GABA$_A$-R agonist muscimol in the setting of inflammation and nerve injury, demonstrating that loss of Myo1a impaired the ionotropic GABAergic signaling. Accordingly, electrophysiological recordings on SC slices demonstrated that under inflammatory conditions, muscimol-evoked increase in excitatory glutamatergic activity of lamina II interneurons was completely abolished in Myo1a KO mice. Using an unbiased RNA deep sequencing screen, they uncovered a selective upregulation of the α2 subunit of the $GABA_A$-R (GABRA2) both in DRG and SC neurons. Together, their data identify Myo1a gene as a predictive genetic factor for the development of injury-induced chronic pain and inflammatory-induced chronic thermal pain through a selective alteration of ionotropic GABAergic signaling.

Inventors now herein describe the use of a nucleic acid sequence encoding Myosin IA (Myo1a), typically the DNA or the mRNA encoding Myo1a, preferably the Myo1a gene, as a biomarker (or predictive genetic factor) for assessing the predisposition of a subject to develop an injury-induced chronic mechanical pain, and/or an inflammatory-induced chronic thermal pain. The mechanical or thermal pain can be a mechanical or thermal allodynia (pain caused by a stimulus that normally is not painful) or hyperalgesia (exaggerated response to a stimulus which is normally painful).

The injury-induced chronic mechanical pain is typically an inflammatory-, a neuropathic- and/or a post-operative-chronic mechanical pain. Each of these three classically distinguished kinds of pain is triggered by an injury, i.e. is associated with tissue damage. More particularly, in the context of the invention:

inflammatory chronic mechanical pain is associated with tissue damage and with the infiltration of immune cells;

neuropathic chronic mechanical pain is triggered by an injury which impacts the nervous system and may or may not involve actual damage to the nervous system, i.e. nerves can be infiltrated or compressed by tumors, strangulated by scar tissue, or inflamed by infection. The pain frequently has burning, lancinating, or electric shock qualities. Persistent allodynia is also a common characteristic of neuropathic pain. The pain may persist for months or years beyond the apparent healing of any damaged tissues.

Examples of neuropathic pain include post herpetic (or post-shingles) neuralgia, reflex sympathetic dystrophy/causalgia (nerve trauma), components of cancer pain, phantom limb pain, entrapment neuropathy (e.g., carpal tunnel syndrome), and peripheral neuropathy (widespread nerve damage). Among the many causes of peripheral neuropathy, diabetes is the most common, but the condition can also be caused by chronic alcohol use, exposure to other toxins (including many chemotherapies), vitamin deficiencies, and a large variety of other medical conditions—it is not unusual for the cause of the condition to go undiagnosed; and post-operative chronic mechanical pain directly results from a tissue damage which occurred during surgery.

The Myo1a gene encodes a member of the myosin superfamily, Myosin-1a (herein also identified as "Myo1a"). The protein represents an unconventional myosin. It should not be confused with the conventional skeletal muscle myosin-1 (MYH1). Unconventional myosins contain the basic domains characteristic of conventional myosins and are further distinguished from class members by their tail domains. They function as actin-based molecular motors. Myosin IA is known to be expressed in neurons of the spinal cord [more specifically in LTMR neurons from the adult lumbar Dorsal Root Ganglion (DRG) also herein identified as "lumbar LTMRs"] and in neurons of specific area of the intestine. Myosin IA is also expressed in the trigeminal nerve (Tyska, M. J. et al.).

The Myo1a gene has been identified as highly polymorphic. More variants than expected were indeed observed (Synonymous: 153.1 expected, 158 observed, $z=-0.25$. Missense: 363.9 expected, 405 observed, $z=-1.05$).

In a typical embodiment of the invention, the absence, a reduced or insufficient expression or a non-functional expression of Myosin IA (Myo1a) in a subject when compared to the expression observed in a Myo1a homozygote ($Myo1a^{+/+}$) reference subject expressing a functional Myosin Ia (Myo1a), predisposes the subject to develop an injury-induced chronic mechanical pain and/or an inflammatory-induced chronic thermal pain.

The reference subject expressing a functional Myosin Ia is a Myo1a homozygote ($Myo1a^{+/+}$) subject. The Myo1a gene of the reference subject consists in SEQ ID NO: 1 or in a functional variant thereof. A functional Myo1a variant of SEQ ID NO:1 encodes a functional Myosin Ia (SEQ ID NO: 2). Functional Myo1a variants can for example, and without limitations, be selected from orthologs of SEQ ID NO: 1 such as SEQ ID NO: 3 (dog) and SEQ ID NO: 5 (cat).

A non-functional expression of Myosin IA is typically associated to a selective upregulation of the α2 subunit of the GABA receptor (GABA-R) in the dorsal root ganglia (DRG) and spinal cord, and can thus be indirectly detected by the skilled person. As well, a detected alteration of the GABAergic signaling in a subject should be a reason for verifying the expression of Myosin IA or for sequencing Myo1a in said subject.

Methods usable by the man of the art to detect or quantify a protein, typically Myosin Ia, are well-known by the skilled man of the art and further identified below in the description.

A preferred method of assessing the predisposition of a subject to develop an injury-induced chronic mechanical pain or an inflammatory-induced chronic thermal pain is an in vitro method comprising a step of analyzing, preferably sequencing, the Myo1a nucleic acid sequence obtained from a biological sample of the subject, the detection of an alteration of the nucleic acid sequence of Myo1a in the subject when compared to the Myo1a wild-type nucleic acid sequence as identified in SEQ ID NO: 1, indicating that the subject is predisposed to develop an injury-induced chronic mechanical pain and/or an inflammatory-induced chronic thermal pain whereas the absence of alteration indicates that the subject is not predisposed to develop an injury-induced chronic mechanical pain and/or an inflammatory-induced chronic thermal pain.

The alteration of the nucleic acid sequence is responsible for an abnormal expression of the Myo1a nucleic acid, typically a reduced, decreased or insufficient expression when compared to the expression observed in a Myo1a homozygote ($Myo1a^{+/+}$) reference subject expressing a functional Myo1a, or of an abnormal, typically a non-functional, expression or activity of the protein (Myo1a) encoded by the nucleic acid.

Typically, the alteration in a nucleic acid sequence may be determined at the level of the Myo1a gene, typically DNA, cDNA or RNA. Preferably, the detection is performed by sequencing all or part of the gene locus or by selective hybridization or amplification of all or part of the gene locus. More preferably a gene locus specific amplification is carried out before the alteration identification step. The altered nucleic acid or gene locus is typically a nucleic acid or gene locus sequence comprising a mutation or combination of mutations in the coding and/or non-coding region of the locus.

The mutation is typically a point mutation, or a deletion or insertion of two or more residues (bases). The point mutation can be a substitution that exchanges one base for another, an insertion in which an extra base is inserted into a new place in the nucleic acid sequence. The point mutation can be a missense mutation, which is a point mutation where a single nucleotide is changed to cause substitution of a different amino acid, or a nonsense mutation, for example a frameshift mutation, that results in a premature stop codon or a nonsense codon in the transcribed mRNA and in a truncated or incomplete protein product.

Deletions may encompass any region of two or more residues in a coding or non-coding portion of the gene locus, such as from two residues up to the entire gene or locus. Typical deletions affect smaller regions, such as domains (introns) or repeated sequences or fragments of less than about 50 consecutive base pairs, although larger deletions may occur as well. Insertions may encompass the addition of one or several residues in a coding or non-coding portion of the gene locus. Insertions may typically comprise an addition of between 1 and 50 base pairs in the gene locus. Rearrangement includes inversion of sequences. The gene locus alteration may result in the creation of stop codons, frameshift mutations, amino acid substitutions, particular RNA splicing or processing, product instability, truncated polypeptide production, etc.

In all cases encountered in the context of the invention, the mutation stops or decreases the production of a functional protein product or results in a non-functional protein product. The mutation is typically a loss-of-function mutation.

A variation or polymorphism which does not impact the functional expression of Myosin Ia will not be identified by the skilled person as an alteration of the nucleic acid sequence.

Within the context of this invention, the "Myo1a gene locus" designates all sequences or products in a cell or organism including the Myo1a coding sequences, Myo1a non-coding sequences (e.g., introns), Myo1a regulatory sequences controlling transcription and/or translation (e.g., promoter, enhancer/silencer regions, terminator, 5'UTR, 3'UTR, etc.), all corresponding expression products, such as Myo1a RNAs (e.g., mRNAs); as well as surrounding sequences of 20 kb region, preferably 15.3 kb region, upstream the starting codon (flanking the 5'UTR region) of the Myo1a gene and 20 kb region, preferably 14.1 kb region, downstream the untranslated region (flanking the 3'UTR region). In a particular embodiment most alterations are not in the promoter sequence.

In a particular embodiment, the altered Myo1a nucleic acid is a Myo1a wild-type nucleic acid comprising at least one point mutation, preferably a single nucleotide polymorphism (SNP), for example a loss-of-function SNP, i.e., a SNP responsible for the absent or abnormal (non-functional) expression of the protein encoded by the nucleic acid. The Myo1a wild-type nucleic acid may also comprise several single nucleotide polymorphism(s) (SNPs).

Once a first SNP has been identified in the genomic region of interest comprising Myo1a other additional SNPs in linkage disequilibrium with this first SNP can be identified. Indeed, any SNP in linkage disequilibrium with a first SNP associated with chronic pain predisposition phenotype will be associated with this trait. Therefore, once the association has been demonstrated between a given SNP and chronic pain predisposition phenotype, the discovery of additional SNPs associated with this trait can be of great interest in order to increase the density of SNPs in this particular region. Identification of additional SNPs in linkage disequilibrium with a given SNP involves: (a) amplifying a fragment from the genomic region comprising or surrounding a first SNP from a plurality of individuals; (b) identifying of second SNP in the genomic region harboring or surrounding said first SNP; (c) conducting a linkage disequilibrium analysis between said first SNP and second SNP; and (d) selecting said second SNP as being in linkage disequilibrium with said first marker. Sub-combinations comprising steps (b) and (c) are also contemplated. These SNPs in linkage disequilibrium can also be used in the methods according to the present invention, and more particularly in the methods of assessing the predisposition of a subject to develop an injury-induced chronic mechanical pain or an inflammatory-induced chronic thermal pain according to the present invention.

Mutations in a gene locus which are responsible for chronic pain predisposition phenotype may be identified by comparing the sequences of the gene locus from patients presenting chronic pain predisposition phenotype to the sequences of the gene locus from reference patients (as defined herein above containing SEQ ID NO:1 or a functional variant thereof). Based on the identified SNPs or association of SNPs of the Myo1a gene, the identified locus can be scanned for mutations. In a preferred embodiment, functional regions such as exons and splice sites, promoters and other regulatory regions of the gene locus are scanned for mutations. Preferably, patients presenting chronic pain predisposition phenotype carry a mutation or a mutated allele shown to be associated with chronic pain predisposition phenotype and referent patients do not carry the mutation or mutated allele associated with chronic pain predisposition phenotype. The method used to detect such mutations generally comprises the following steps: amplification of a region of the gene locus of interest comprising a SNP or a group of SNPs associated with chronic pain predisposition phenotype from DNA samples of the gene locus from patients presenting chronic pain predisposition and from referent patients; sequencing of the amplified region; comparison of DNA sequences of the Myo1a genes from patients presenting chronic pain predisposition phenotype and from patients presenting referent phenotype; determination of mutations specific to patients presenting chronic pain predisposition phenotype.

In a particular embodiment, the method of assessing the predisposition of a subject to develop an injury-induced chronic mechanical pain or an inflammatory-induced chronic thermal pain is an in vitro method comprising the following steps of (a) obtaining from the subject a test sample of Myo1a DNA, cDNA or RNA, preferably DNA, (b) contacting the test sample with at least one nucleic acid probe, wherein said nucleic acid is complementary to and specifically hybridises with a targeted altered Myo1a nucleic acid sequence preferably comprising at least one mutation, typically a point mutation, for example a single nucleotide polymorphism (SNP), to form a hybridization sample, (c) maintaining the hybridization sample under conditions sufficient for the specific hybridization of the targeted nucleic acid sequence with the nucleic acid probe to occur, and (d) detecting whether there is specific hybridization of the altered targeted nucleic acid sequence with the nucleic acid probe, such a specific hybridization revealing the predisposition of the subject to develop an injury-induced chronic mechanical pain or an inflammatory-induced chronic thermal pain.

Most of the herein described preferred methods of assessing the predisposition of a subject to develop an injury-induced chronic mechanical pain or an inflammatory-induced chronic thermal pain are performed on the nucleic acid obtained from cells of a biological sample which is typically a blood sample, a plasma sample or a serum sample of the subject.

Although less preferred, the alteration may also be determined at the level of the Myosin IA polypeptide (e.g., a pre-protein and the mature protein).

Examples of particular techniques the aim of which is to determine the abnormal (in particular low or absent) expression of a particular nucleic acid, or the abnormal expression of the corresponding Myosin IA polypeptide or protein are detailed in the present description.

The presence of an alteration in a nucleic acid may be easily detected by the man skilled in the art using methods of the art such as restriction digestion, sequencing, selective hybridisation (for example with a nucleic acid probe present on a nucleotide array), and/or selective amplification, as further explained below.

Alterations in a gene may also be detected by determining the presence of an altered RNA expression. Altered RNA expression includes the presence of an altered RNA sequence, the presence of an altered RNA splicing or processing, the presence of an altered quantity of RNA, etc. These may be detected by various techniques known in the art, including by sequencing all or part of the RNA or by selective hybridisation or selective amplification of all or part of said RNA, for instance.

The presence of an abnormal expression of a target nucleic acid, such as Myo1a, may be detected in particular by real time quantitative reverse transcription PCR (qRT-PCR) using probes designed to hybridize within the target nucleic acid sequence (see O'Driscoll L. et al., 1993 and Yajima T. et al, 1998).

In a further variant, the method comprises detecting the presence of an altered expression of the polypeptide or protein encoded by the gene of interest. Altered polypeptide expression includes the presence of an altered polypeptide sequence, the presence of an altered quantity of polypeptide, the presence of an altered tissue distribution, etc. These may be detected by various techniques known in the art, including by sequencing and/or binding to specific ligands (such as antibodies), for instance. In a particular embodiment, the detection of an abnormal protein expression may be easily performed, by the man skilled in the art, by measuring the cellular level of mRNA encoding a normal protein, a decreased level compared to a control or standard level being correlated to an abnormal protein expression.

Sequencing can be carried out using techniques well known in the art, using automatic sequencers. The sequencing may be performed on the complete gene locus or, more preferably, on specific domains thereof, typically those known or suspected to carry deleterious mutations or other alterations.

Amplification is based on the formation of specific hybrids between complementary nucleic acid sequences that serve to initiate nucleic acid reproduction. Amplification may be performed according to various techniques known in the art, such as by polymerase chain reaction (PCR), ligase chain reaction (LCR), strand displacement amplification (SDA) and nucleic acid sequence based amplification (NASBA). These techniques can be performed using commercially available reagents and protocols. Preferred techniques use allele-specific PCR or PCR-SSCP. Amplification usually requires the use of specific nucleic acid primers, to initiate the reaction. Nucleic acid primers useful for amplifying sequences from the gene locus of interest are able to specifically hybridize with a portion of the gene locus that flank a target region of said locus, said target region being altered in subjects predisposed to develop an injury-induced chronic mechanical pain or an inflammatory-induced chronic thermal pain.

Another particular object of this invention resides in a nucleic acid primer useful for amplifying sequences from the Myo1a gene or locus of interest including surrounding regions. Such primers are preferably complementary to, and hybridize specifically to nucleic acid sequences in the gene locus. Particular primers are able to specifically hybridize with a portion of the gene locus that flank a target region of said locus, said target region being altered in subjects predisposed to develop an injury-induced chronic mechanical pain or an inflammatory-induced chronic thermal pain. Primers that can be used to amplify a target region comprising SNPs may be designed based on their sequence or on the genomic sequence of the Myo1a gene.

The invention also relates to a nucleic acid primer, said primer being complementary to and hybridizing specifically to a portion of the Myo1a gene locus coding sequence (e.g., gene or RNA) altered in certain subjects predisposed to develop an injury-induced chronic mechanical pain or an inflammatory-induced chronic thermal pain. In this regard, particular primers of this invention are specific for altered sequences in a Myo1a gene locus or RNA. By using such primers, the detection of an amplification product indicates the presence of an alteration in the gene locus. In contrast, the absence of amplification product indicates that the specific alteration is not present in the considered sample.

The invention also concerns the use of a nucleic acid primer or a pair of nucleic acid primers as mentioned above, and as herein identified, in a method of assessing the predisposition of a subject to develop an injury-induced chronic mechanical pain or an inflammatory-induced chronic thermal pain.

Hybridization detection methods are based on the formation of specific hybrids between complementary nucleic acid sequences that serve to detect nucleic acid sequence alteration(s). A particular detection technique involves the use of a nucleic acid probe specific for wild-type (or a functional variant thereof) or altered gene or corresponding RNA, followed by the detection of the presence of a hybrid. The probe may be in suspension or immobilized on a substrate or support (as in nucleic acid array or chips technologies). The probe is typically labeled to facilitate detection of hybrids.

In this regard, a particular embodiment of this invention comprises contacting the sample from the subject with a nucleic acid probe specific for an altered Myo1a gene locus, and assessing the formation of a hybrid.

In a particularly preferred embodiment, the method comprises contacting simultaneously the sample with a set of probes that are specific, respectively, for wild type Myo1a gene locus and for various altered forms thereof. In this embodiment, it is possible to detect directly the presence of various forms of alterations in the gene locus in the sample. Also, various samples from a single subject or from various subjects may be treated in parallel.

Within the context of this invention, a probe refers to a polynucleotide sequence which is complementary to and capable of specific hybridization with a (target portion of) the Myo1a gene or RNA, and which is suitable for detecting mutations associated with the gene alleles which predispose to an injury-induced chronic mechanical pain or an inflammatory-induced chronic thermal pain ("mutated allele").

Probes are preferably perfectly complementary to the particular Myo1a gene, RNA, or target portion thereof probes typically comprise single-stranded nucleic acids of between 8 to 1000 nucleotides in length, for instance of between 10 and 800, more preferably of between 15 and 700, typically of between 20 and 500. It should be understood that longer probes may be used as well. A preferred probe of this invention is a single stranded nucleic acid molecule of between 8 to 500 nucleotides in length, which can specifically hybridize to a region of a Myo1a gene locus or RNA that carries an alteration.

The method of the invention employs a nucleic acid probe specific for an altered (e.g., a mutated) Myo1a gene or RNA, i.e., a nucleic acid probe that specifically hybridizes to said altered Myo1a gene or RNA and essentially does not hybridize to a Myo1a gene or RNA lacking said alteration.

Specificity indicates that hybridization to the target sequence generates a specific signal which can be distinguished from the signal generated through non-specific hybridization. Perfectly complementary sequences are preferred to design probes according to this invention. It should be understood, however, that certain mismatch may be tolerated, as long as the specific signal may be distinguished from non-specific hybridization.

The invention also concerns the use of a nucleic acid probe as described above, and as herein identified, in a method of assessing the predisposition of a subject to develop an injury-induced chronic mechanical pain or an inflammatory-induced chronic thermal pain.

As indicated above, alteration in the Myo1a gene locus may also be detected by screening for alteration(s) in Myo1a polypeptide sequence or expression levels in a sample of a tissue expressing the protein of interest (Myosin IA). In order to detect a protein, immunohistochemistry (for example in a biopsy), immunoblotting (in particular Western blot), proteomics, or antibody-based biosensors directed against the protein of interest (Myosin IA), as well as any other method known from the man of the art, can be applied to a biological sample containing Myosin IA from the subject of interest. Contacting the sample with a ligand specific for a Myosin IA encoded by a particular nucleic acid sequence and determining the formation of a complex is also described.

Different types of ligands may be used, such as specific antibodies. In a specific embodiment, the sample is contacted with an antibody specific for a Myosin IA encoded by a particular nucleic acid and the formation of a complex is determined. Various methods for detecting such a complex can be used, such as ELISA, radio-immunoassays (RIA) and immuno-enzymatic assays (IEMA).

Within the context of this invention, an antibody designates a polyclonal antibody, a monoclonal antibody, as well as fragments or derivatives thereof having substantially the same antigen specificity. Fragments include Fab, Fab'2, CDR regions, etc. Derivatives include single-chain antibodies, humanized antibodies, poly-functional antibodies, etc. An antibody specific for a polypeptide encoded by a particular gene designates an antibody that selectively binds said polypeptide, i.e., an antibody raised against said polypeptide or an epitope-containing fragment thereof. Although non-specific binding towards other antigens may occur, binding to the target polypeptide occurs with a higher affinity and can be reliably discriminated from non-specific binding.

The methods according to the invention of assessing the predisposition of a subject to develop an injury-induced chronic mechanical pain or an inflammatory-induced chronic thermal pain are preferably performed on a subject before any surgical procedure.

It is also disclosed kits to assess the predisposition of a subject to develop an injury-induced chronic mechanical pain or an inflammatory-induced chronic thermal pain comprising products and reagents for detecting in a sample from a subject the presence of an alteration in a Myo1a gene locus or in the corresponding polypeptide or protein; in the Myo1a gene or corresponding polypeptide or protein expression; and/or in the Myo1a gene activity.

Such kits comprise any nucleic acid, typically any primer, any pair of primers and/or any nucleic acid probes (wild-type and mutant); any ligand, preferably antibody, described in the present invention; and/or any device comprising such nucleic acid(s) and/or ligand(s) immobilized on a support. The herein described kits can further comprise reagents and/or protocols for performing a hybridization, amplification or antigen-antibody immune reaction. These kits may further comprise a micro-array to be used for the herein described methods and read through quantitative PCR or multiplex technology. A particular device comprises at least one complementary nucleic acid, preferably several complementary nucleic acids, that bind all or part of the Myo1a gene or of a Myo1a gene locus immobilized on a support.

Particular kits, typically kits for assessing the predisposition of a subject to develop an injury-induced chronic mechanical pain or an inflammatory-induced chronic thermal pain, are the following kits:

a kit for sequencing the Myo1a nucleic acid obtained from a biological sample of a subject, wherein the kit comprises nucleic acid sequences, typically oligonucleotides, for example primers or pair(s) of primers;

a kit to detect the abnormal/altered expression, in a biological sample of the subject, typically a blood sample, of the Myo1a gene of the subject, the kit comprising (i) at least one pair of primers and (ii) at least one labelled/detectable (for example fluorescent) probe, for example two different probes, allowing the quantitative detection of the expression of Myo1a, and (iii) a leaflet providing the control quantitative expression value corresponding to Myo1a in a control population; and a kit to detect the abnormal/altered expression, in a biological sample of the subject, typically a blood sample, of the Myo1a gene of the subject, the kit comprising (i) at least one pair of primers, and (ii) at least two differently labelled probes, the first probe recognizing the wild-type allele and the second probe recognizing the mutated allele of Myo1a.

When a subject do not express or abnormally express Myosin Ia, i.e. insufficiently express Myosin Ia or express a non-functional Mysosin Ia, inventors herein indicate that an "adapted treatment of pain" has to be applied to the subject to prevent or treat pain. Indeed, inventors have discovered that once the injury-induced chronic pain is established in said subject, said pain cannot be reversed by alkaloids, in particular $GABA_A$-R agonists such as muscimol, and becomes irreversible.

Within the context of the present invention, the term "treatment" or "treating" pain in a subject, designates delaying, stabilizing, curing, healing, alleviating, relieving, altering, ameliorating, improving, remedying or affecting any form of pain in a subject as described herein, or any disease or condition associated with pain (in particular any inflammatory or neuropathic condition associated with pain), or any symptom of such a disease or condition, after the application or administration of a suitable compound or a composition according to the invention. The term "treatment" or "treating" also refers to any indicator of success in the treatment of pain (which may be associated with any injury, pathology or condition), including any objective or subjective parameter such as abatement, remission, slowing progression or severity, stabilization, diminishing of symptoms of pain, or making it more tolerable to the subject. The term "treating" pain, also includes increasing pain tolerance and/or decreasing perceived pain. In particular embodiments, the methods, compounds and composition of the invention are for increasing pain tolerance and/or for decreasing perceived pain. As used herein, the term "pain tolerance" refers to the amount of pain that a subject can perceive and withstand before breaking down emotionally and/or physically. Pain tolerance is distinct from pain threshold (the minimum stimulus necessary to produce pain). As used herein, "increasing pain tolerance" generally refers to a situation where a subject can develop a greater pain tolerance (that is, less perceived pain) when compared to a previous state, for instance, following administration of suitable compounds or compositions to a subject.

Within the context of this invention, "preventing" or "prevention" in relation to pain in a subject, refers to at least the reduction of likelihood of the risk of (or susceptibility to) acquiring any kind of pain by a subject, after the application or administration of a suitable compound or a composition according to the invention. For example, "preventing" includes causing at least one of the clinical symptoms of pain, typically chronic pain, not to develop in a subject, typically in a subject identified as predisposed to chronic pain, in particular to an injury-induced chronic mechanical pain and/or an inflammatory-induced chronic thermal pain, but does not yet experience or display symptoms of pain.

The adapted treatment of pain according to the present invention typically involves the exogenous supply, administration for example, to the subject, of a nucleic acid sequence (typically a DNA or a mRNA) encoding Myo1a, and/or of an agonist of the Myosin 1a protein. Administration can be for example an intrathecal (i.t.) administration.

An object of the invention therefore concern a nucleic acid sequence (typically a DNA or a mRNA) encoding Myo1a, and/or an agonist of the Myosin Ia protein, Myo1a being a functional Myo1a, for use for preventing or treating pain, in particular an injury-induced chronic mechanical pain and/or an inflammatory-induced chronic thermal pain, in a subject as herein defined.

In the present invention, the term "agonist of the Myosin Ia protein" is used to designate any protein capable of activating or stimulating the biological function of the wild-type Myosin IA protein or of restoring the function of a functionally altered Myosin IA protein. Such an agonist can be a natural or recombinant protein or a protein fragment that exhibits the properties of the corresponding wild-type protein, in particular that is able to activate or stimulate the biological function of the wild-type Myosin IA protein or of restoring the function of a functionally altered Myosin IA protein.

The present invention also concerns the use of a DNA encoding Myo1a, a mRNA encoding Myo1a, or an agonist of the Myosin 1a protein, Myo1a being a functional Myo1a, for preparing a composition, typically a pharmaceutical composition, for preventing or treating pain, in particular an injury-induced chronic mechanical pain and/or an inflammatory-induced chronic thermal pain, in a subject.

The present invention further concerns a composition comprising a DNA encoding Myo1a, a mRNA encoding Myo1a, or an agonist of the Myosin 1a protein and a pharmaceutically acceptable carrier or support, typically a composition for use for preventing or treating pain, in particular an injury-induced chronic mechanical pain and/or an inflammatory-induced chronic thermal pain, in a subject.

Appropriate excipient, diluant or carrier usable in the all present invention may be selected for example from saline, isotonic, sterile or buffered solutions, etc. They can further comprise stabilizing, sweetening and/or surface-active agents, etc. They can be formulated in the form of ampoules, flasks, tablets, or capsules, by using techniques of galenic known per se.

The present invention also relates to a method for preventing or treating pain, in particular injury-induced chronic mechanical pain and/or an inflammatory-induced chronic thermal pain, comprising the administration to the subject, typically a mammal, in particular a human being, in need thereof, of at least one compound selected from the previously described product.

A subject in need of a treatment or prophylaxis is subject that has been tested and identified as predisposed to develop an injury-induced chronic mechanical pain and/or an inflammatory-induced chronic thermal pain according to the method described above.

The present invention also provides:

an in vitro, in vivo or ex vivo method for screening or selecting a compound that is able to prevent the conversion of acute pain into chronic pain, in particular the occurrence of an injury-induced chronic mechanical pain and/or an inflammatory-induced chronic thermal pain in a subject identified as predisposed to such a pain, the method comprising a step of assessing the expression of Myo1a by a particular cell, tissue or animal model in the presence of a test compound, wherein an increased expression of functional Myo1a by the particular cell, tissue or animal model, in comparison with a control cell, tissue or animal model that has not been exposed to or contacted with the test compound, is indicative of the capacity of said compound to prevent the conversion of acute pain into chronic, in particular the occurrence of an injury-induced chronic mechanical pain and/or an inflammatory-induced chronic thermal pain in a subject identified as predisposed to such a pain, an in vitro, in vivo or ex vivo method for screening a compound usable for preventing or treating pain, in particular an injury-induced chronic mechanical pain and/or an inflammatory-induced chronic thermal pain, in a subject having an altered Myo1a nucleic acid, an altered Myo1a nucleic acid expression, or an altered/abnormal expression or activity of the corresponding Myosin IA protein, said method comprising determining in vitro, in vivo or ex vivo the ability of a test compound to (i) restore a functional expression of said altered or abnormal Myosin IA protein (ii) induce or increase the expression or activity of said protein, or (iii) induce or increase the expression or activity of an agonist ligand of said protein, an in vitro, in vivo or ex vivo screening method of a Myo1a modulator, comprising determining the ability of a drug candidate to activate or stimulate, or on the contrary to decrease or suppress, Myo1a functional expression and/or biological function, and, if the ability is confirmed, the identification of the drug candidate as a Myo1a agonist (activator), and potentially as a drug candidate for preventing, reducing or treating pain, or on the contrary as a Myo1a antagonist (inhibitor), and an in vitro or ex vivo screening method of a drug candidate for preventing, reducing or treating pain, comprising determining the ability of a drug candidate to activate or stimulate, or on the contrary to decrease or suppress, Myo1a functional expression, and, if the ability is confirmed, the identification of the drug candidate as a Myo1a agonist and as a drug candidate for preventing, reducing or treating pain, or on the contrary as a Myo1a antagonist.

The compounds identified with one of the herein described screening methods may be used, in the context of the present invention, for preventing or treating pain in a subject, in particular injury-induced chronic mechanical pain and/or an inflammatory-induced chronic thermal pain.

Inventors further herein describe, the first animal model, a Myo1a KO (Myo1a$^{-/-}$) mice, in which a loss-of-function mutation leads to an irreversible pain state after injury. This mouse model is described in Tyska et al. (2005).

An object of the invention thus concerns the use of such a Myo1a KO (Myo1a$^{-/-}$) animal model for screening for Myo1a modulators and/or for drugs for preventing, reducing or inhibiting pain.

This model can be used to design appropriate pharmacological therapies to prevent the onset and establishment of chronic pain.

This model can further be used to as a laboratory tool for use in research to deepen the understanding of the cellular and molecular mechanisms that trigger the transition from acute to chronic pain.

Other characteristics and advantages of the invention are given in the following experimental section (with reference to FIGS. 1-8 and Tables 1-4), which should be regarded as illustrative and not limiting the scope of the present application.

FIGURES

The patent or application file contains at least one drawing executed in color. Copies of this patent or patent application publication, with color drawing(s), will be provided by the Office upon request and payment of the necessary fee.

FIG. 1. Loss of LTMRs-enriched Myo1a converts injury induced acute mechanical pain into chronic pain.

(A-C) Characterization of Myo1a-expressing neurons in adult lumbar Dorsal Root Ganglion (DRG). ISH using Myo1a antisense probe (red) followed by double immunolabeling with anti-GINIP (blue) antibody and IB4 (green) (A) or anti-Ret antibody (blue) (C). (B) Double-ISH using Myo1a (red) and TrkB antisense probes (green). Scale bars: 100 µm.

(D-E) Analysis of Myo1a expression by ISH (red) in E15 and new-born (P0) DRG and SC tissues. Scale bars: 50 µm (D) and 100 µm (E).

(F) ISH using Myo1a probe (in white, left panel) or no probe (right panel) on adult SC tissue. Dashed area delimitates laminae I-IIo of SC.

(G) Quantification of Myo1a transcripts in adult DRG and SC (relative to β-actin). Data represent the mean±SEM of 3 independent experiments.

(H-J) Mechanical responses of WT and KO mice following carrageenan-induced inflammation (n=11 for WT and n=13 for KO) (H), CCI surgery (n=9 for WT and n=10 for KO) (I) and paw incision surgery (n=10 for WT and n=10 for KO) (J). Data are presented as mean±SEM for each group (*p<0.05; p<0.01; *p<0.001). (See also FIGS. 5-7).

Figure 2:
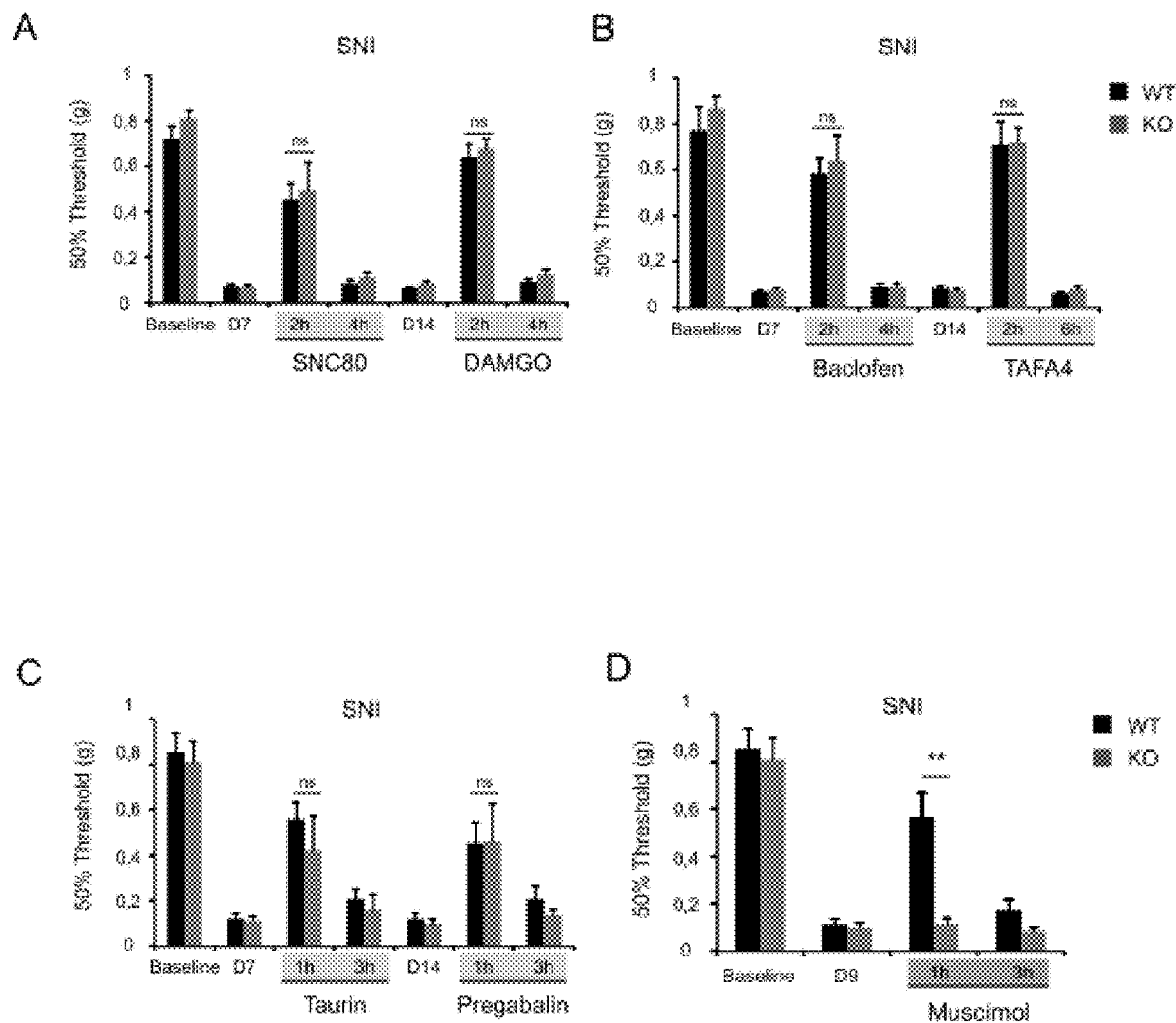
Figure 2:
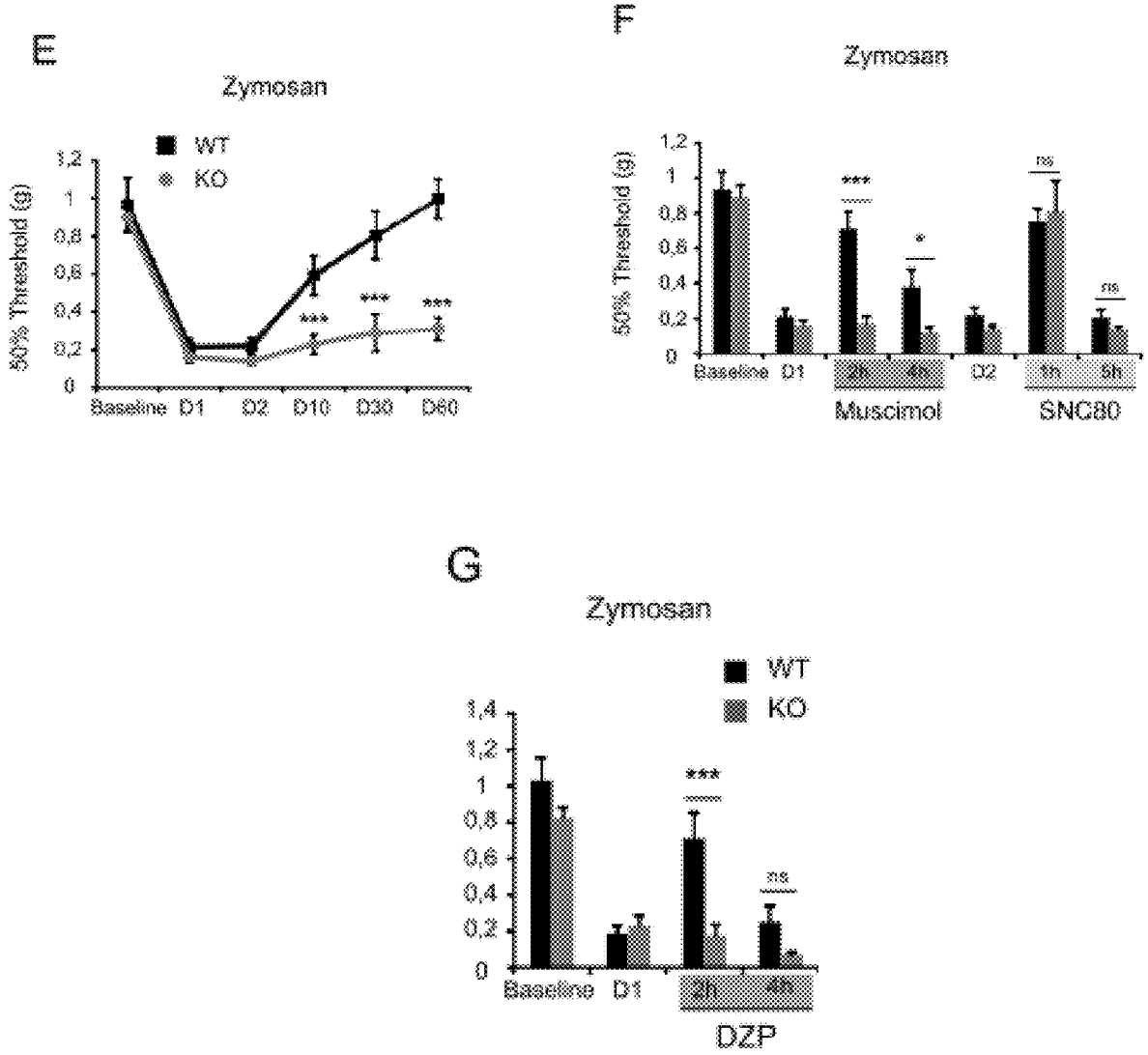

FIG. 2. Muscimol—and Diazepam-mediated analgesia is impaired in Myo1a KO mice.

(A-D) Mechanical responses of WT and KO mice following SNI surgery and i.t administration at indicated time-points of 10 nmol of SNC80, 0.2 nmol of DAMGO (A), 0.1 µg of baclofen, 2 µg of TAFA4 (n=6 mice per genotype) (B), 40 µg of taurine, i.p administration of 3 mg/kg of pregabalin (n=8 mice per genotype) (C) and i.t administration of 0.15 µg of muscimol (n=8 mice per genotype) (D).

(E-G) Mechanical responses of WT and KO mice following zymosan-induced inflammation (n=9 mice per genotype) (E) and i.t administration at indicated time-points of 0.15 µg of muscimol, 10 nmol of SNC80 (n=9 mice per genotype) (F) and 0.09 mg/kg of DZP (G) (n=7 mice per genotype). Data are presented as mean±SEM for each group (*p<0.05; p<0.01; *p<0.001; ns: non-significant).

Figure 3:
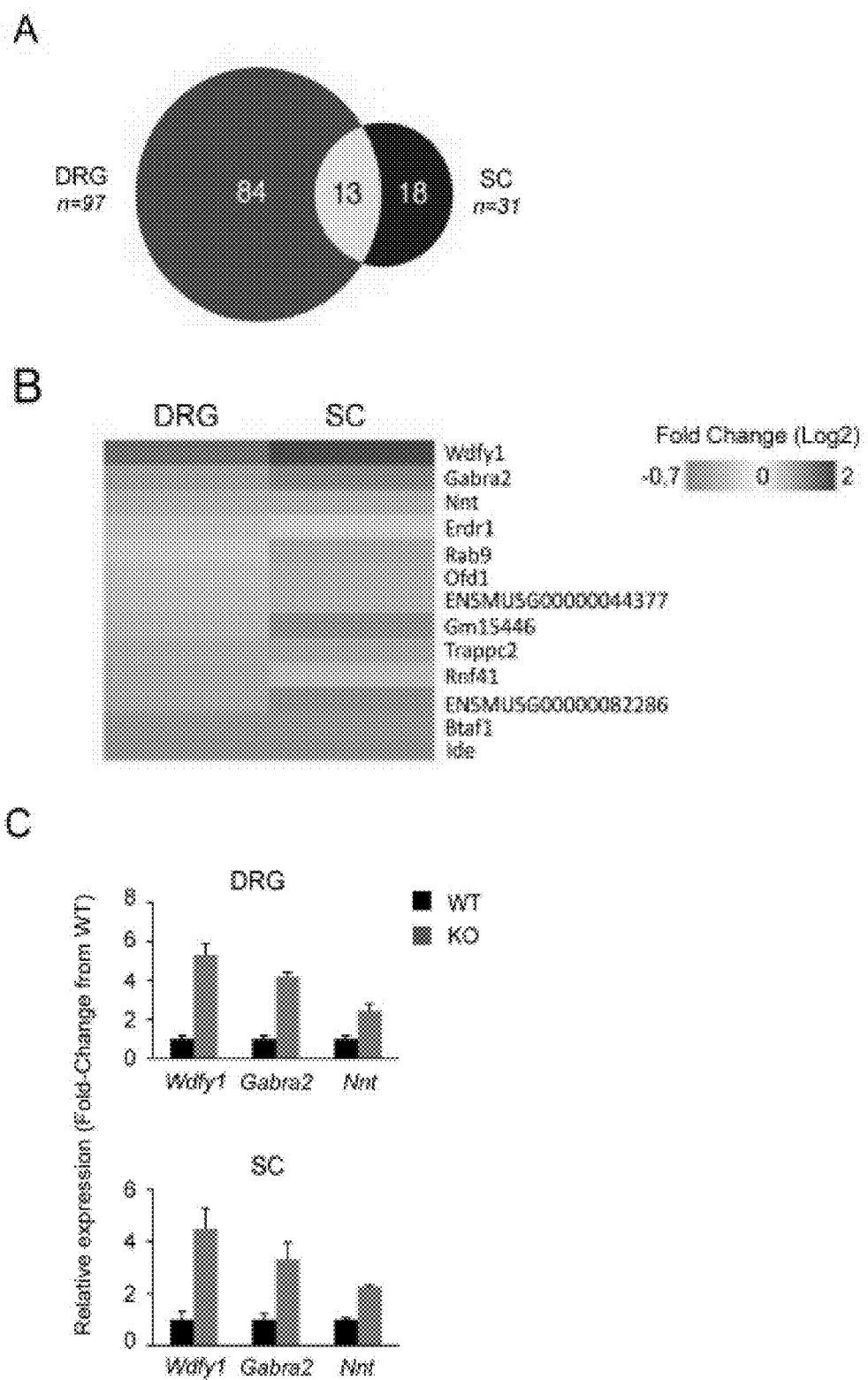
Figure 3:
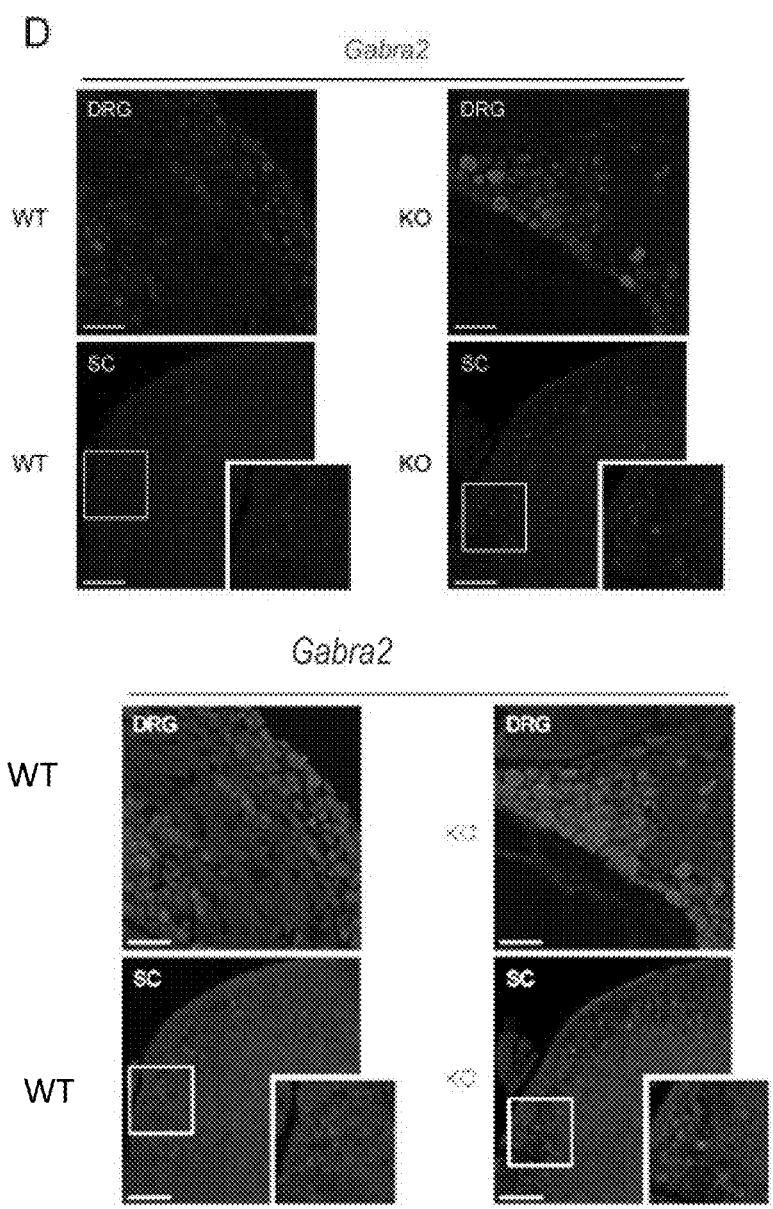
Figure 3:
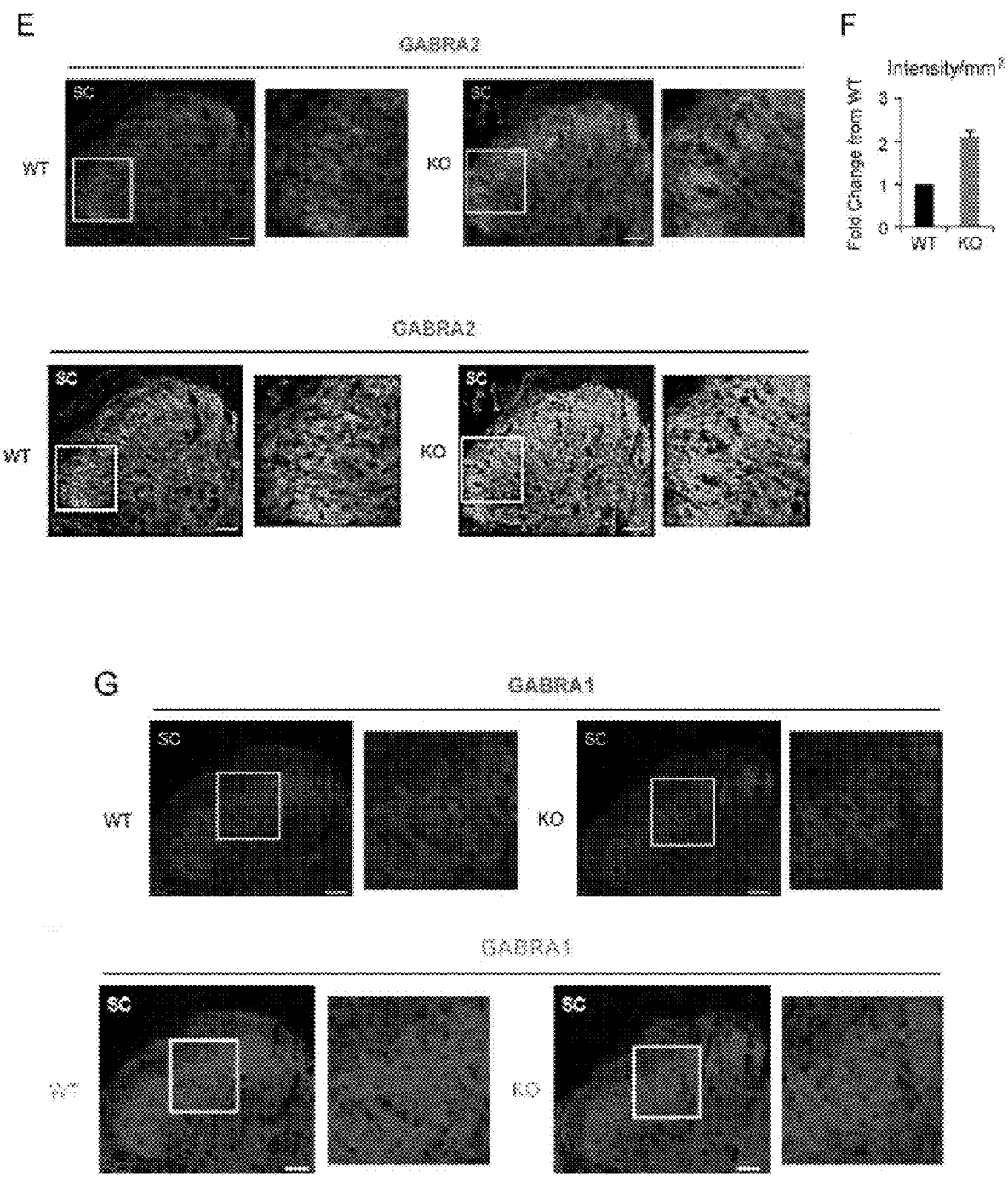

FIG. 3. Transcriptional analysis of DRG and SC tissue from WT and Myo1a KO mice reveals an increased Gabra2 expression.

(A) Venn diagram representing the number of differentially expressed (DE) genes (5% false discover rate) in KO mice with respect to WT in DRG (97 DE genes) and SC (31 DE genes) neurons. Genes differentially expressed only in DRG are represented in red (84 genes), only in SC in blue (18 genes) or in both DRG and SC neurons in yellow (13 genes).

(B) Heatmap representation of DE genes in both DRG and SC neurons, where genes showing increased expression are shown in red and those showing decreased expression in green. Scale represents the Log 2 fold change in expression observed in KO mice with respect to WT.

(C) Quantification of Wdfy1, Gabra2 and Nnt transcripts in DRG and SC tissues from WT and KO mice. Data represent the mean fold-change of KO vs WT±SEM (n=3 independent experiments).

(D) Gabra2 transcripts expression assessed by ISH (red) in L5 DRG (upper panels) and in lumbar SC (lower panels) from WT (left) and KO (right) mice. Scale bars: 100 µm.

(E) Immunostaining showing GABRA2 protein expression (green) in the dorsal horn of lumbar SC from WT (left) and KO (right) mice. Scale bars: 50 µm.

(F) Quantification of GABRA2 immunofluorescence intensity in the laminae I-III of SC from WT and KO mice. Data represent the mean fold change of KO vs WT±SEM (n=3 independent experiments).

(G) Immunostaining showing GABRA1 protein expression (red) in lumbar SC dorsal horn of WT (left) and KO (right) mice. Scale bars: 50 µm. (See also Tables 1-4).

Figure 4:
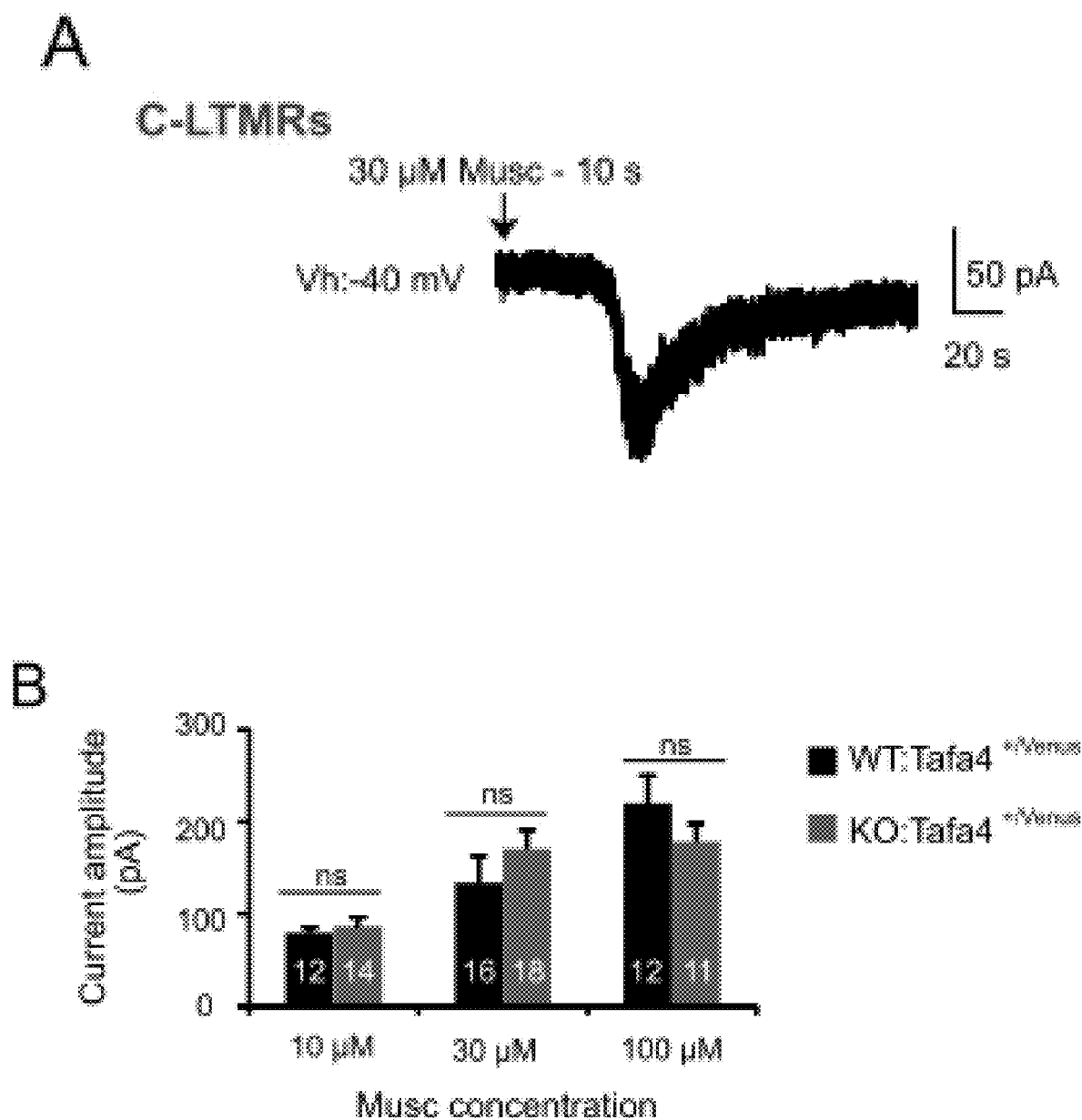
Figure 4:
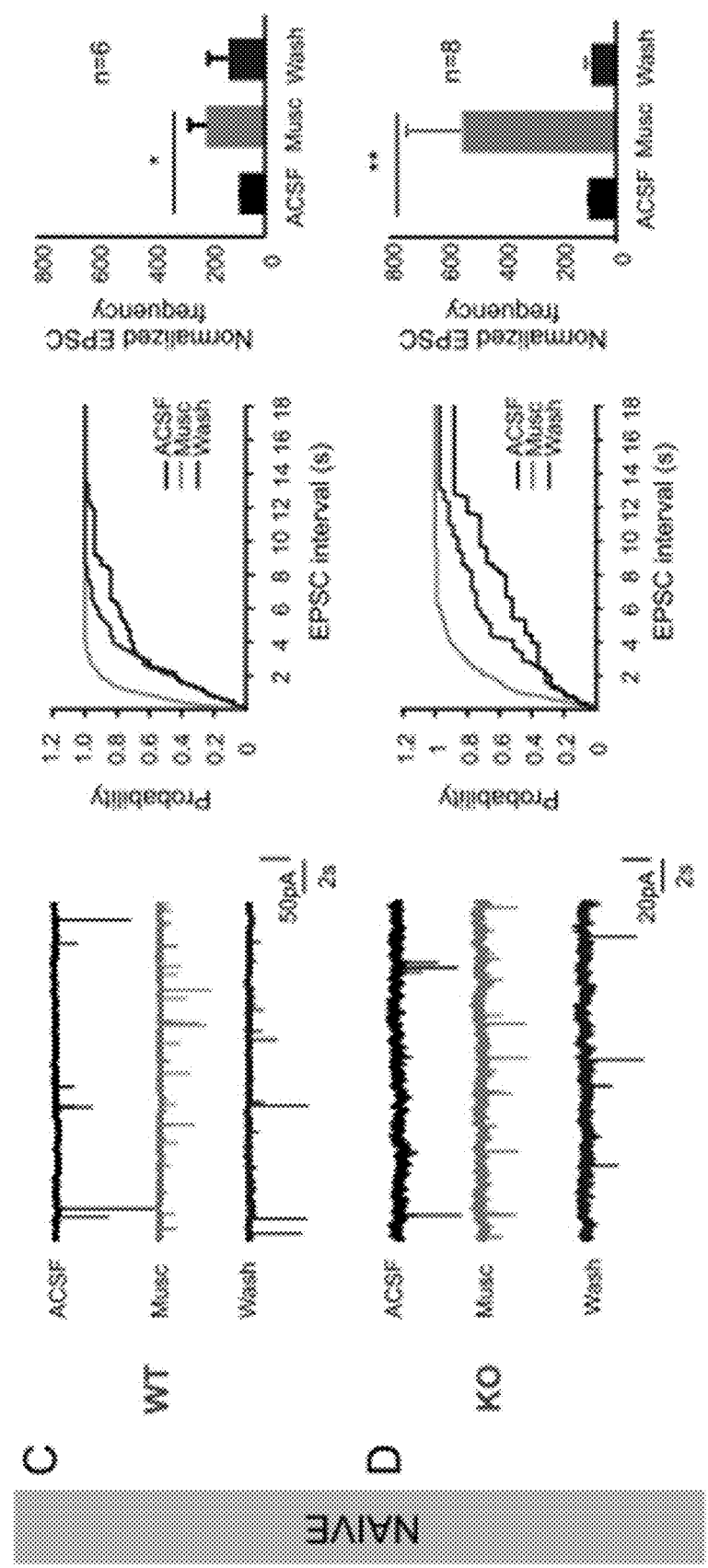
Figure 4:
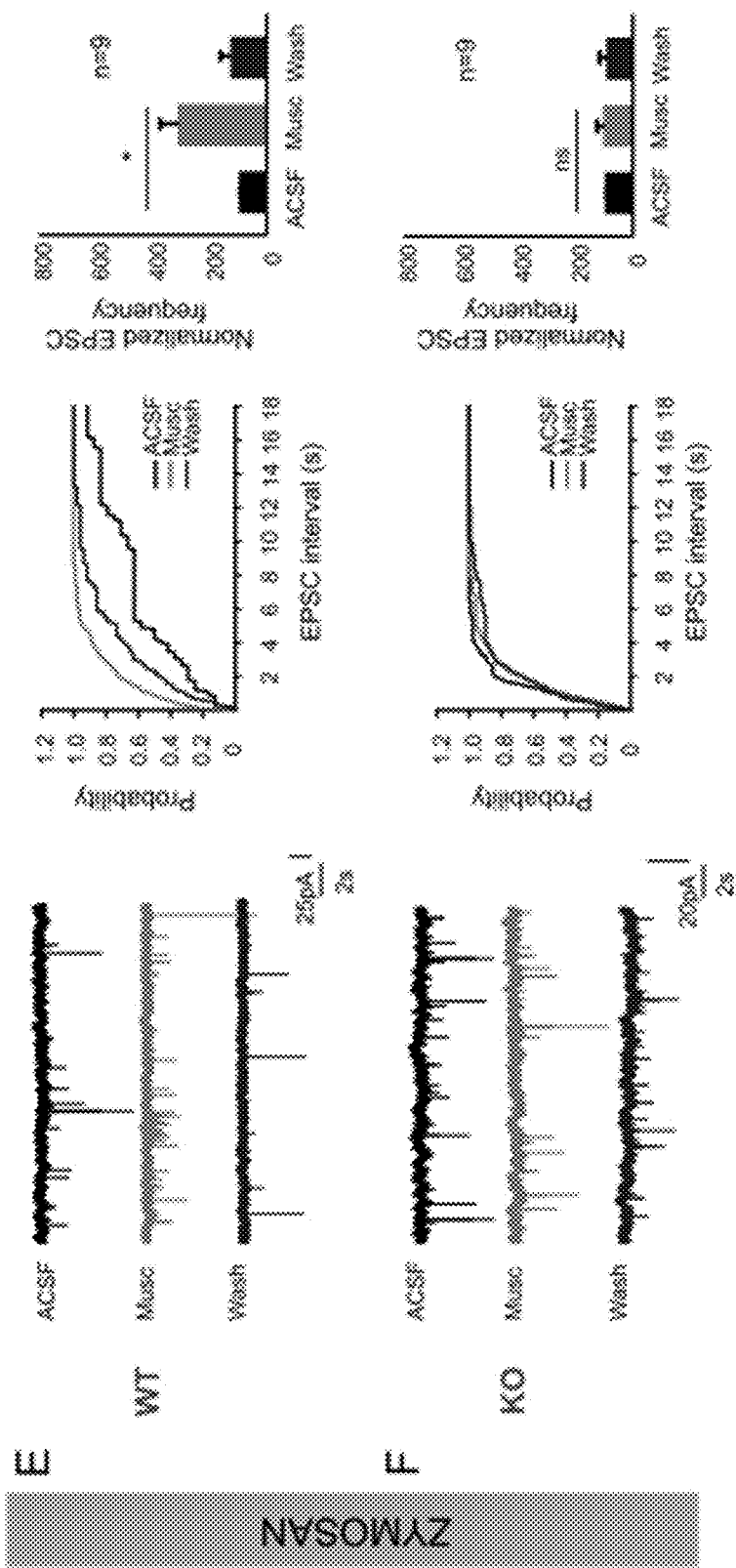

FIG. 4: Muscimol-induced increase in EPSC frequency is lost in Myo1a KO mice after zymosan inflammation.

(A) Representative traces of whole-cell recordings of muscimol-induced currents (Musc) in dissociated C-LTMRs.

(B) Current amplitude (mean±SEM) after bath application of indicated doses of Musc, recorded in C-LTMRs from WT:Tafa4$^{+/Venus}$ and KO:Tafa4$^{+/Venus}$s mice. The number of recorded cells is indicated on the histograms.

(C-F) Whole cell recordings of spontaneous EPSC in laminae II interneurons after Musc application in naïve (C-D) and in zymosan-inflamed WT and KO mice (E-F).

Left panels: representative traces of EPSC obtained under ACSF (black traces), following superfusion of 5 µM Musc (blue traces) and during wash (brown traces).

Middle panels: Cumulative distribution of EPSC intervals (in seconds) for the experiments shown in the left panels. Note the shift of the Musc/blue curves towards the left (C, D, E middle panels), indicating a reversible increase in EPSC frequency.

Right panels: Normalized EPSC frequency (mean±SEM) under ACSF, following superfusion of 5 µM Musc and during wash. Note the absence of effect of Musc in slices from zymosan inflamed mice. The number of recorded cells is indicated in the right panels (*p<0.05; **p<0.01; ns: non-significant). (See also FIG. 8).

Figure 5:
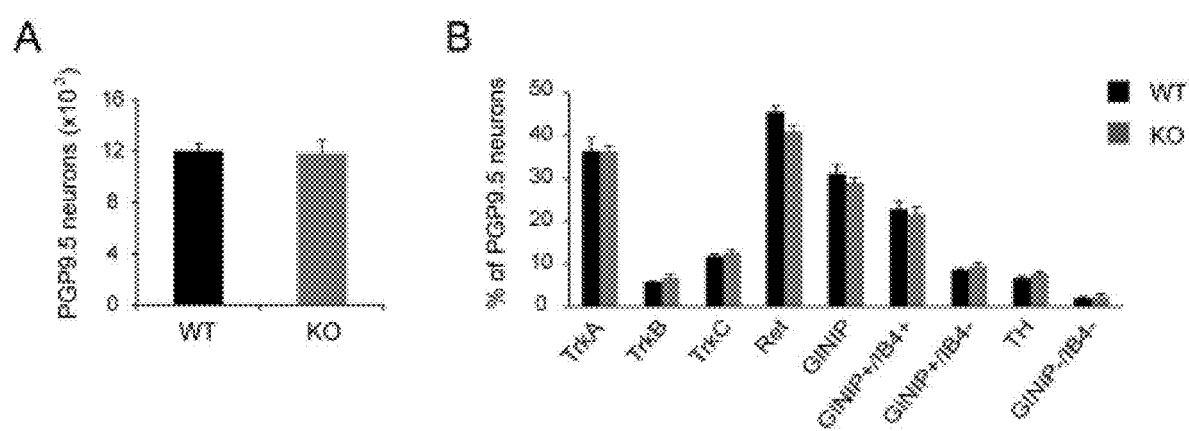
Figure 5:
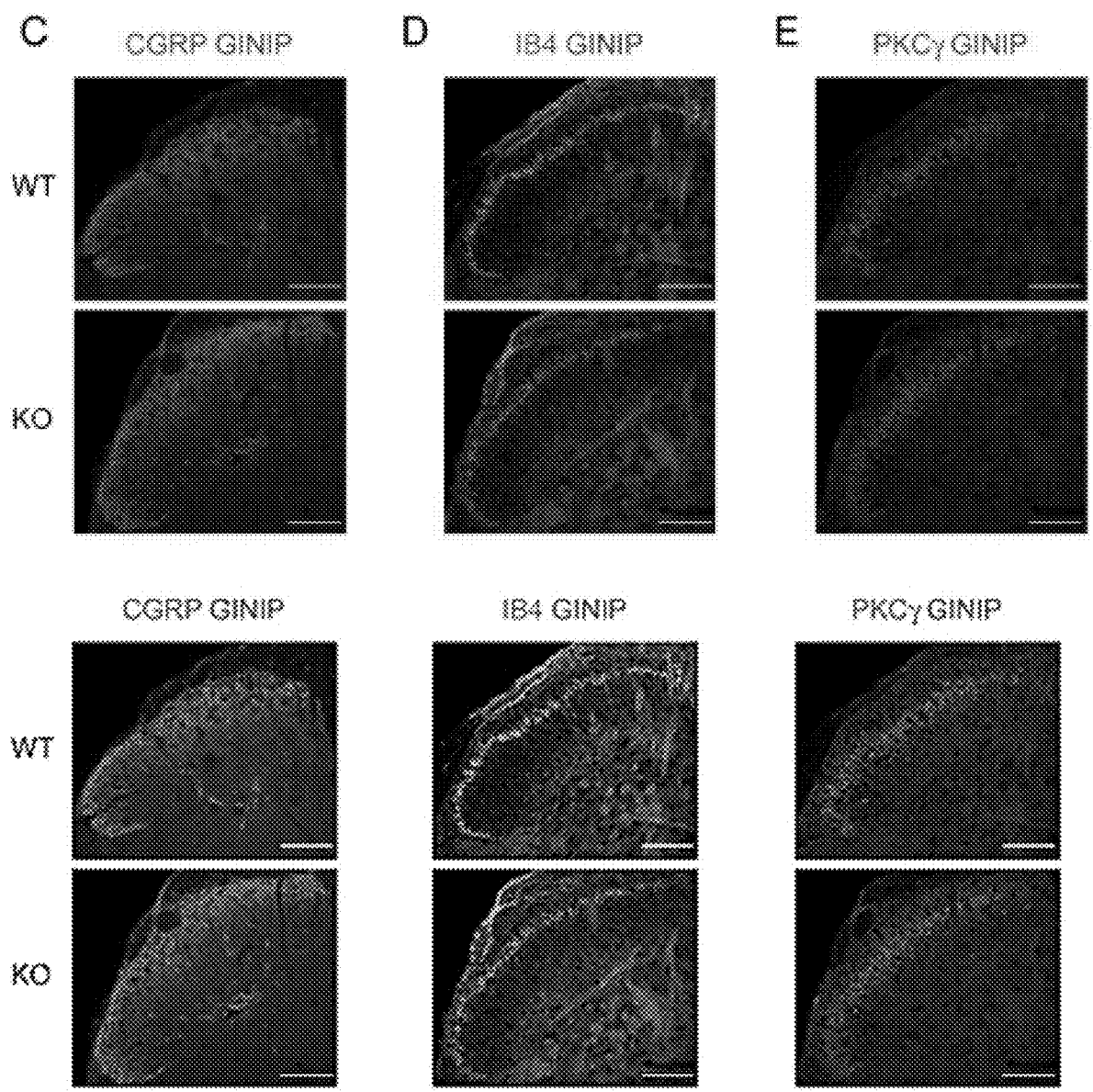
Figure 5:
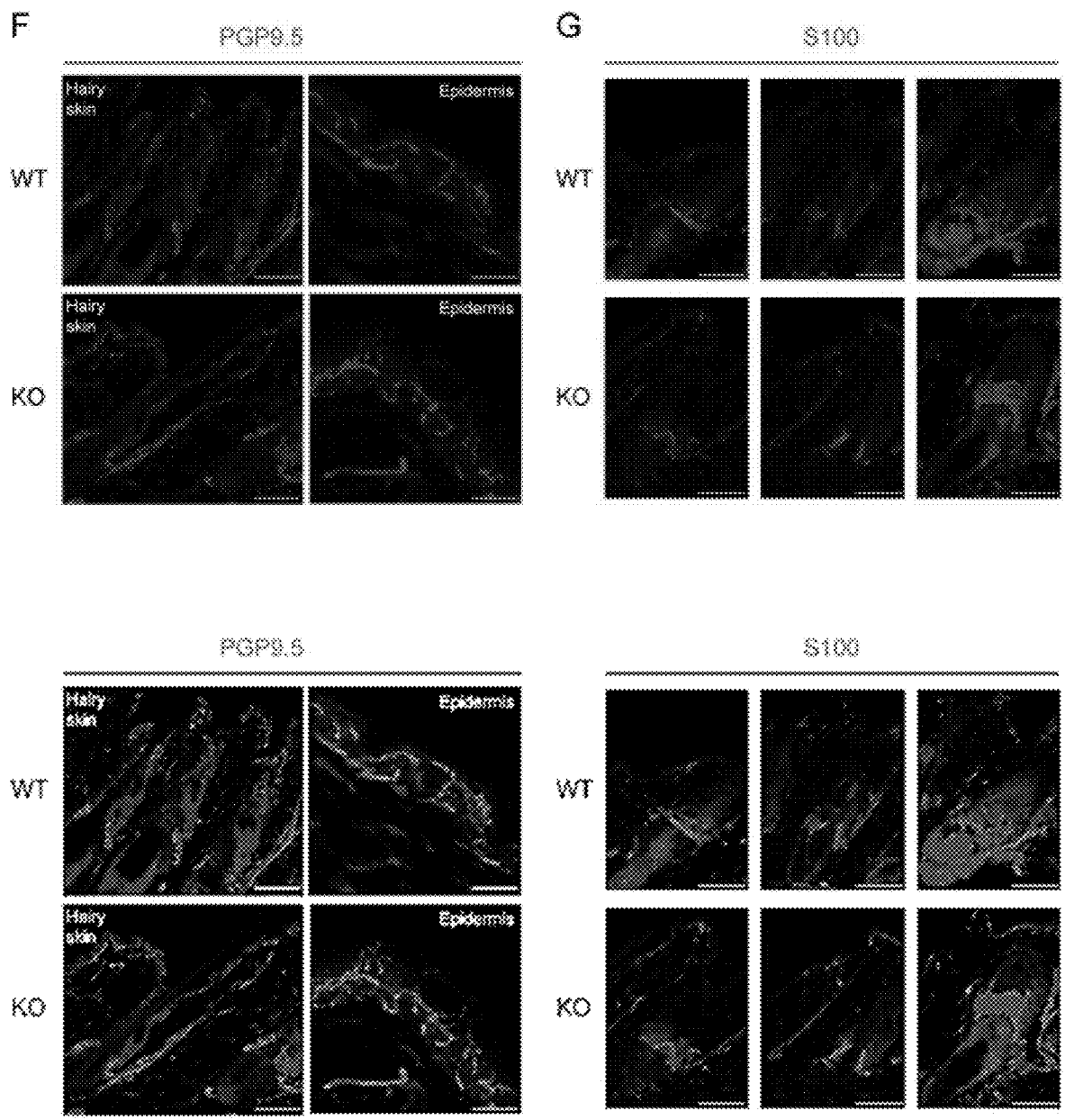

FIG. 5: Adult DRG neurons survival, specification, central and peripheral innervation are not impaired in absence of MYO1A.

(A-B) Cell counts of total PGP9.5$^+$ (A) and of indicated subsets (B) realized on adult lumbar L4 DRG sections from WT and KO mice. Data represent the mean absolute values (A) or the mean % of PGP9.5 neurons (B)±SEM of three independent experiments. No statistically significant differences were observed between genotypes.

(C-E) Sensory neurons innervation of the SC is preserved in Myo1a KO mice.

Immunostainings of SC transversal sections from WT (upper panels) and KO (lower panels) mice with anti-CGRP (red, C), GINIP (blue C-E), IB4 (green, D) and anti-PKCγ (red, E). Scale bars: 100 μm.

(F-G) Sensory neurons innervation of the hairy skin is preserved in Myo1a KO mice.

Immunostainings of hairy skin sections from WT (upper panels) and KO (lower panels) mice with anti-PGP9.5 (red, F) and anti-S100 (red, G). Scale bars: PGP9.5 and S100 showing hairy skin innervation: 50 μm. PGP9.5 showing epidermis innervation: 15 μm. (Related to FIG. 1).

Figure 6:
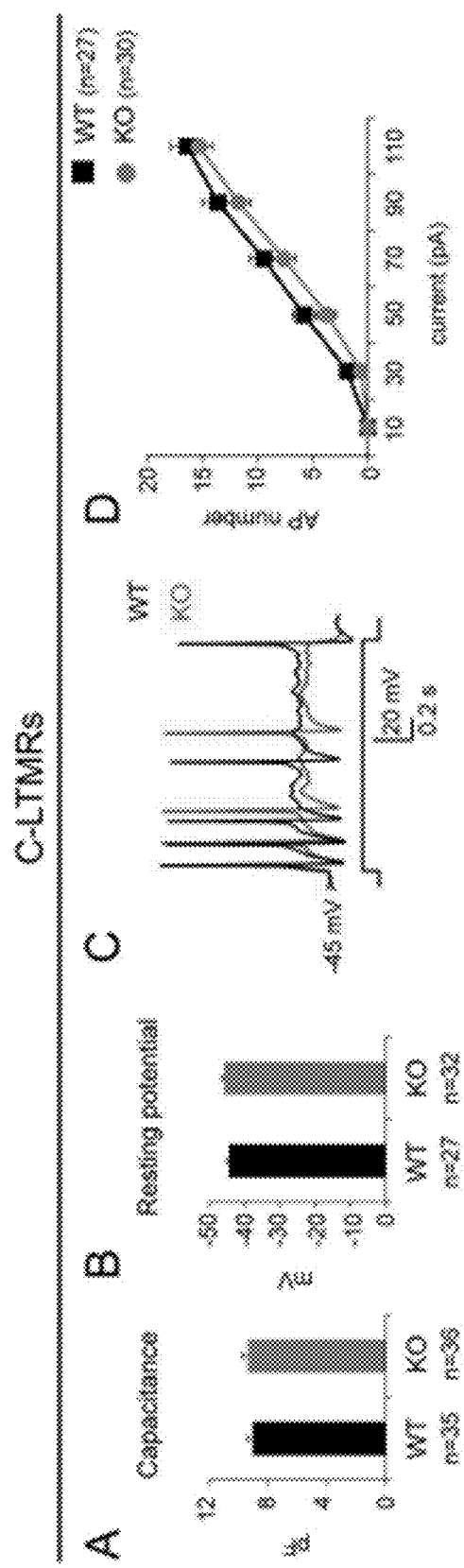
Figure 6:
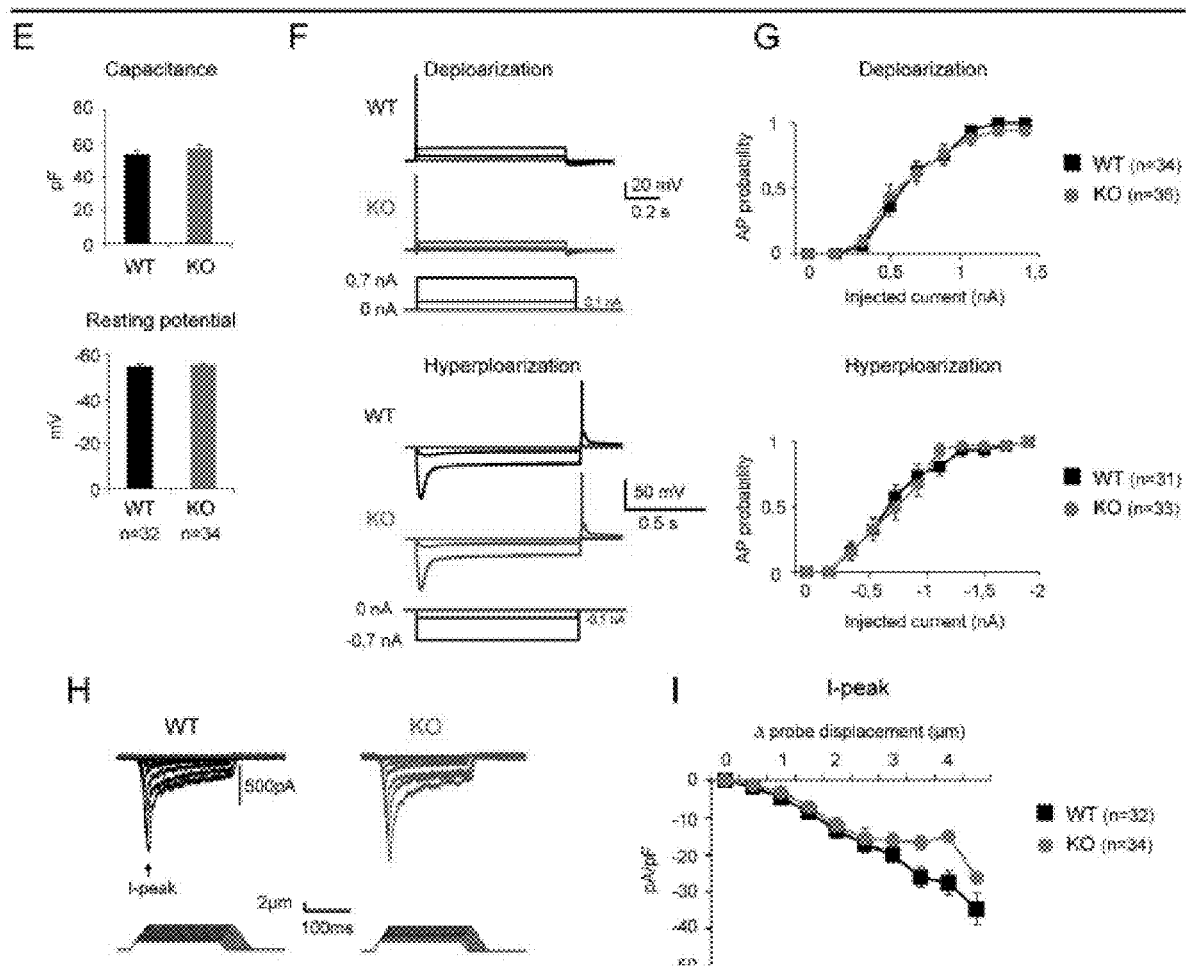

FIG. 6: C-LTMRs and Aδ-LTMRs electrophysiological properties are preserved in absence of MYO1A.

(A-D) Electrophysiological properties of C-LTMRs.

(A-B) The graphs show the capacitance and the resting membrane potential of WT and KO C-LTMRs.

(C) Representative traces illustrating the response of WT and KO C-LTMRs to depolarizing current pulse (50 pA, 1000 ms).

(D) The graph represents the number of Action Potentials (AP) evoked by depolarizing current steps of increasing amplitude (Δ10 pA, 1000 ms) of WT (black) and KO C-LTMRs (grey).

(E-I) Electrophysiological properties of Aδ-LTMRs.

The cell capacitance (upper panel) and resting membrane potential (lower panel) of WT and KO Aδ-LTMRs are shown in E. APs were evoked by depolarizing (F-G upper panels) or hyperpolarizing (F-G lower panels) current injection (1000 ms, Δ0.1 nA or Δ−0.1 nA, respectively). (F) The figure shows representative traces obtained for WT (black) and KO (red) Aδ-LTMRs. (G) The curves represent the probability of AP firing as function of the injected current during depolarizing (upper panels) or following hyperpolarizing (lower panels) current injection, respectively. The AP rebound observed at the termination of the hyperpolarizing pulse is a characteristic of Aδ-LTMRs.

(H) Representative mechano-activated (MA) currents in WT (black) and KO (red) Aδ-LTMRs elicited by incremented mechanical stimulations of the soma at a holding potential of −60 mV.

(I) Peak amplitude (I-peak) was normalized to obtain the current/probe displacement curve. The curves show the normalized peak current (I-peak) as function of the probe displacement.

Mean normalized amplitudes do not differ between WT and KO Aδ-LTMRs.

No statistically significant differences were observed between genotypes in C-LTMRs and Aδ-LTMRs. Data are expressed as mean±SEM. (Related to FIG. 1).

Figure 7:
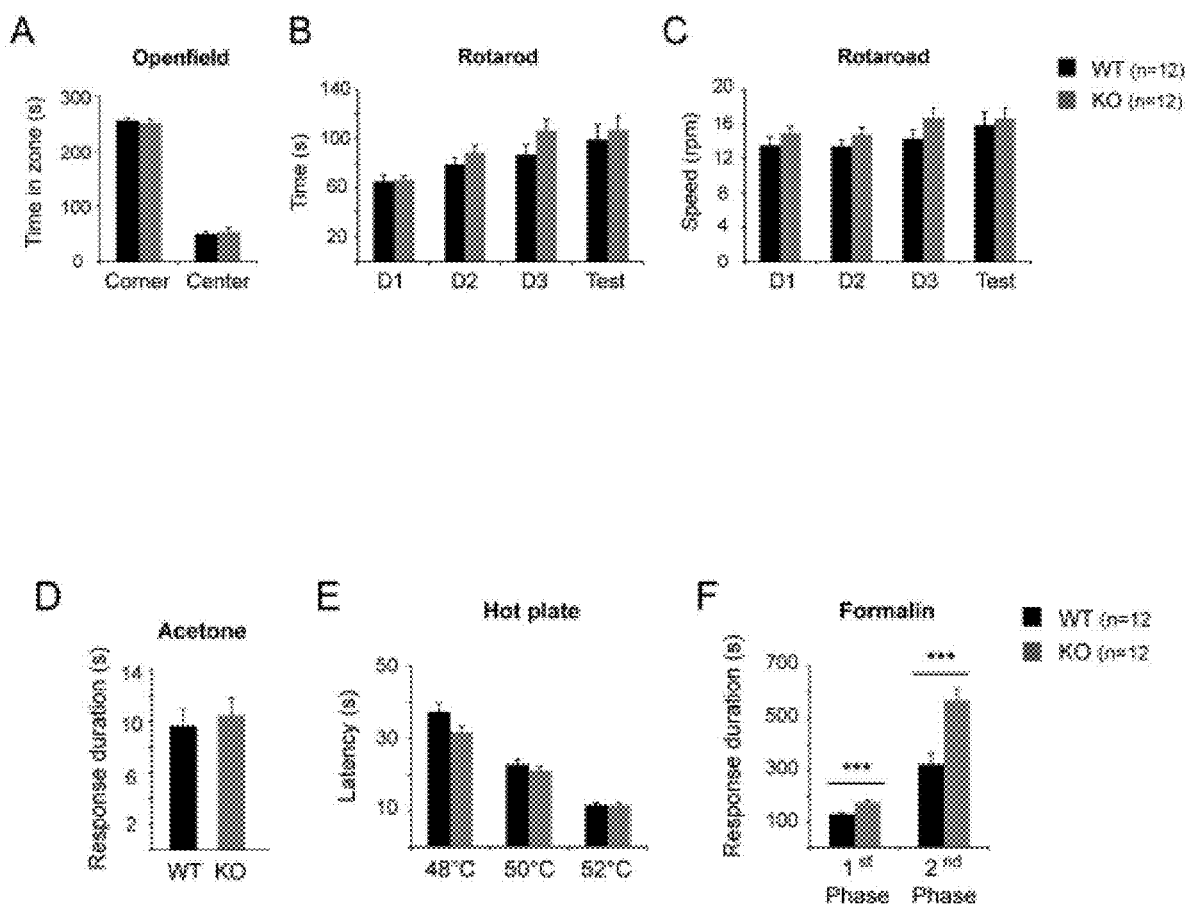
Figure 7:
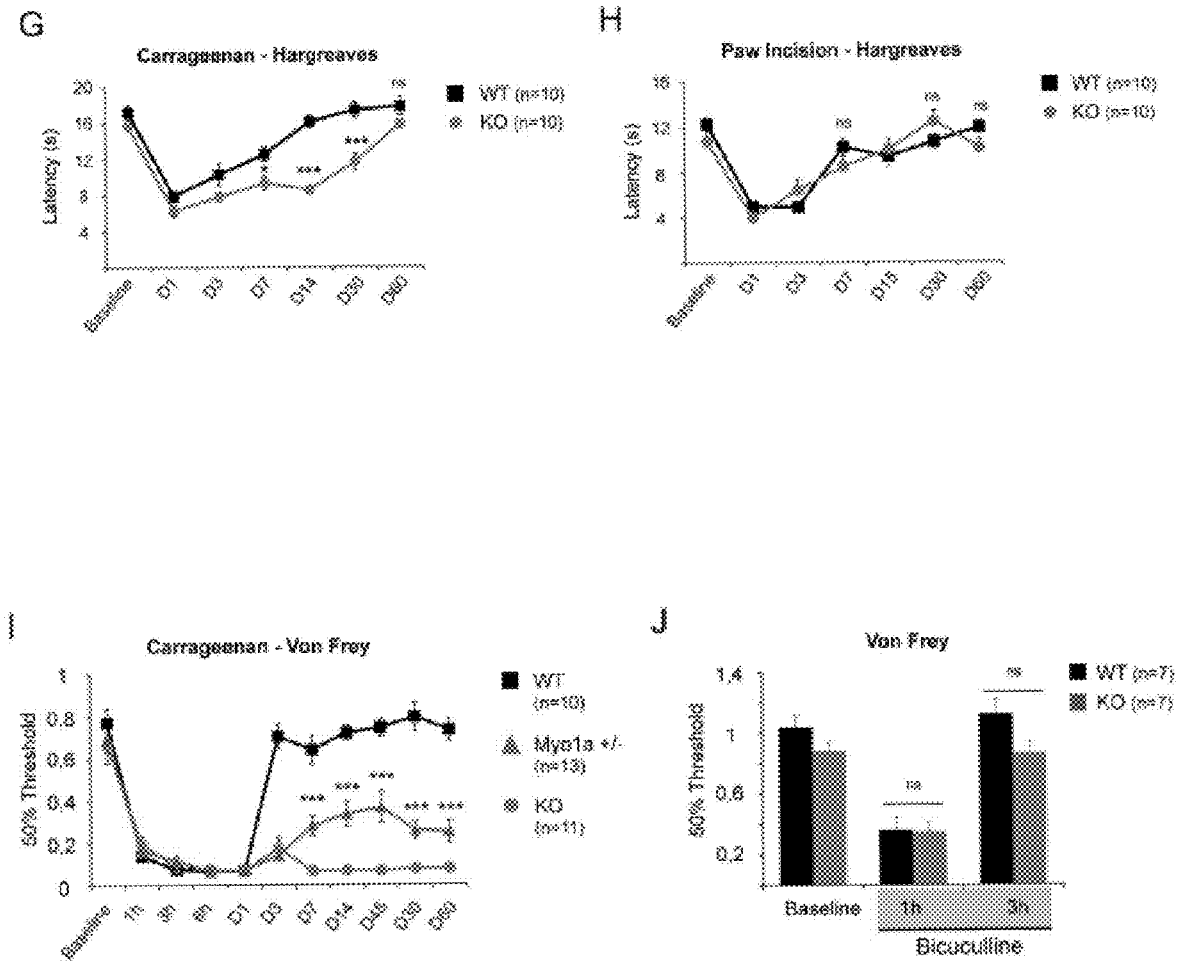

FIG. 7: Behavioral characterization of naive Myo1a KO mice and Myo1a$^{+/-}$ mice and thermal and mechanical hypersensitivity post-injury.

Behavior of WT and KO in the open field (A) and rotarod (B: time and C: speed) tests. Thermal sensitivity to paw cooling (D: acetone test) and noxioux heat (E: hotplate test) show no difference between genotypes.

(F) The graph illustrates WT and KO mice pain behavior in formalin test. The histograms represent the response duration during the 1$^{st}$ and the 2$^{nd}$ phase. Note that KO mice exhibit increased response duration in this test (***p<0.001).

(G-H) Thermal hypersensitivity of WT and KO mice following carrageenan-induced inflammation (G) and paw incision surgery (H) was determined in Hargreaves test (***p<0.001, ns: non significant).

(I) Mechanical responses of WT, Myo1a$^{+/-}$ and KO mice following carrageenan-induced inflammation (***p<0.001, Myo1a$^{+/-}$ versus WT).

(J) Mechanical responses of WT and KO mice after i.t injection of bicuculline (0.01 μg in 10 μL) (ns: non significant).

Data are presented as mean±SEM for each group. (Related to FIG. 1).

Figure 8:
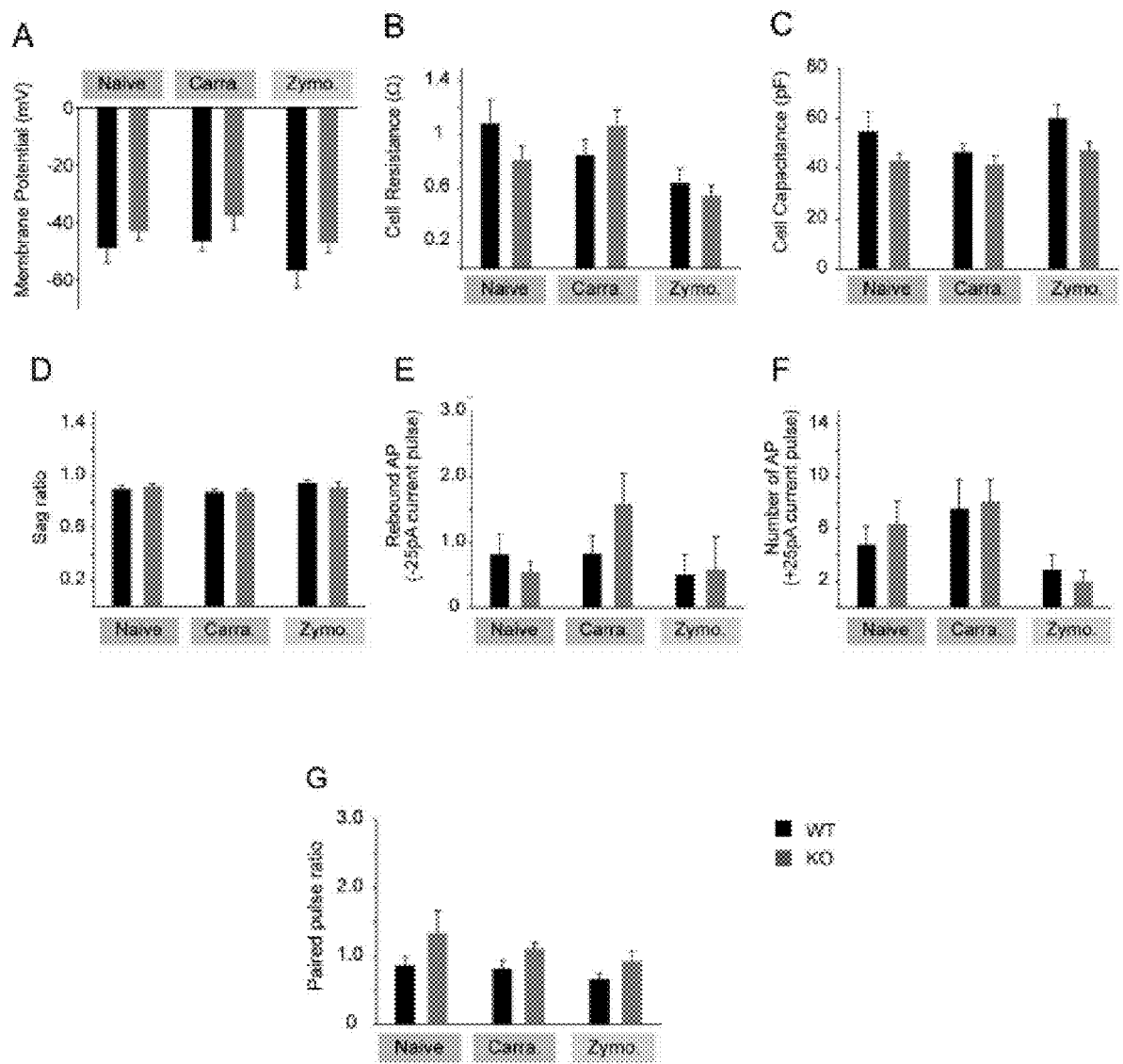

FIG. 8: Electrophysiological characterization of SC lamina II neurons passive, active and synaptic properties in Myo1a KO naive or inflamed mice.

(A-F) The graphs represent the average membrane potential (A), the membrane resistance (B), the capacitance (C), the Sag ratio in response to −25 pA hyperpolarizing pulse (D), the number of rebound AP in response to −25 current pulses (E) and the number of AP in response of +25 pA current pulses (F) of SC lamina II interneurons from WT and KO mice under naive and in carrageenan—(Carra.) and zymosan—(Zymo.) —induced inflammation. The numbers of recorded cells are: Naive: 16 WT and 26 KO, Carra.: 29 WT and 23 KO and Zymo.: 10 WT and 12 KO.

(G) The graph illustrates the paired pulse ratio recorded in SC lamina II interneurons of WT and KO mice under naive and in Carra. and Zymo—induced inflammation. The numbers of recorded cells are: Naive: 19 WT and 33 KO, Carra.: 9 WT and 13 KO and Zymo.: 9 WT and 9 KO.

Data are presented as mean±SEM for each group. No significant differences were observed between genotypes. (Related to FIG. 4).

FIGS. 1A, B, C, D, E, FIGS. 3D, E, G and FIGS. 5C, D, E, F, G are each shown twice (identical figures showing colors with different contrasts).

EXPERIMENTAL PART

Materials & Methods

Mice

Mice were maintained under standard housing conditions (23° C., 40% humidity, 12 h light cycles, and free access to food and water). Special effort was made to minimize the number as well as the stress and suffering of mice used in this study. All protocols are in agreement with European Union recommendations for animal experimentation.

Myo1a KO mice were generated by Tyska et al., 2005 (Tyska et al., 2005). Control wild-type (WT) C57BL/6 mice were bred in-house. WT: Tafa4$^{+/Venus}$ and Myo1a KO: Tafa4$^{+/Venus}$ mice were generated by crossing WT and Myo1a KO mice respectively with Tafa4$^{Venus/Venus}$(Delfini et al., 2013) and Myo1a$^{+/-}$: Tafa4$^{+/Venus}$ mice.

Histology

To obtain adult Dorsal Root Ganglia (DRGs) and Spinal Cord (SC) specimens for in situ hybridization (ISH) and immunostainings, mice were deeply anesthetized with a mix of ketamine/xylazine and then transcardially perfused with an ice-cold solution of paraformaldehyde 4% in 0.1 M phosphate buffer (4% PFA). Tissues were further fixed for 24 h in ice-cold 4% PFA. Newborn P0 mice were sacrificed, rapidly washed in ice-cold PBS, eviscerated and fixed for 24 h in ice-cold 4% PFA. E15 embryos were collected in ice-cold PBS and fixed for 24 h in ice-cold 4% PFA. Adult back hairy skin was excised and fixed for 2 h in ice-cold 4% PFA. For GABRA1 and GABRA2 immunostainings, lumbar SC (L1-L3) was rapidly dissected and fixed for 30 min in ice-cold 4% PFA. Specimens were transferred into a 30% (w/v) sucrose solution for cryoprotection before being frozen in OCT mounting medium. 12 μm cryosections (DRGs) and 18-20 μm cryosections (SC, E15 and P0) were obtained using a standard cryostat (Leica).

In Situ Hybridization

Digoxigenin-labeled Myo1a and Gabra2 antisense probes and Fluorescein-labeled TrkB probe were synthetized using gene-specific PCR primers and cDNA templates from adult mouse DRG and in situ hybridization or double in situ hybridization was carried as described in (Reynders et al., 2015). The primers used for probe synthesis are listed below:

```
Myo1a F1:
                                   (SEQ ID NO: 7)
GAAAATACTTCCGGTCAGGTG,
Myo1a R1:
                                   (SEQ ID NO: 8)
CAAGGGTTCTTCATCTCTGAGT,

Myo1a F2:
                                   (SEQ ID NO: 9)
TACCAGTGGAAGTGCAAGAAGT,
Myo1a R2 + T7:
                                   (SEQ ID NO: 10)
TAATACGACTCACTATAGGGACACTACGAAGTTCTGCTCCAG,

Gabra2 F1/F2:
                                   (SEQ ID NO: 11)
ACTTGGTTACTTTTGGGCTGT,
Gabra2 R1:
                                   (SEQ ID NO: 12)
TGATTGAAGTGAGCTGAAAGGT,
Gabra2 R2 + T7:
                                   (SEQ ID NO: 13)
TAATACGACTCACTATAGGGAACATCCTTTCATGGTGACTCA, TrkB-F1:
                                   (SEQ ID NO: 14)
CTGAGAGGGCCAGTCACTTC,
TrkB-R1:
                                   (SEQ ID NO: 15)
CATGGCAGGTCAACAAGCTA, TrkB-F2:
                                   (SEQ ID NO: 16)
CAGTGGGTCTCAGCACAGAA,
TrkB-R2 + T7:
                                   (SEQ ID NO: 17)
TAATACGACTCACTATAGGGCTAGGACCAGGATGGCTCTG.
```

Immunostaining

Immunostainings were done with rat anti-GINIP (1:500, Moqrich laboratory), goat anti-Ret (1:500, R&D Systems), rabbit anti-TrkA (1:1000, generous gift from Dr. L. Reichardt, University of California), goat anti-TrkC (1:500, R&D Systems), rabbit anti-CGRP (1:1000, ImmunoStar), rabbit anti-PKCγ (1:500, Santa Cruz), rabbit anti-PGP9.5 (1:200, Thermo Scientific), rabbit-anti S100 (1:1000, Darko), rabbit anti-GABRA2 (1:2000, Synaptic Systems) and guinea pig anti-GABRA1 (1:1000, Synaptic Systems). IB4 labelling was performed with Alexa Fluor 488-conjugated IB4 from Invitrogen. Slides were mounted with ImmuMount (Thermo Scientific) prior to observation under Axiolmager Z1 (Zeiss) fluorescence microscope. Contrast was adjusted using Photoshop software. For the comparison of Gabra2 expression between WT and Myo1a KO, images were acquired using the same exposure parameters and contrast was adjusted equivalently.

For SC and skin innervation as well as GABRA staining, image acquisition was performed using an LSM-780 confocal microscope (Zeiss) and same pinhole aperture, lasers intensities as well as gain parameters were respected between WT and Myo1a KO specimens.

Cell Counts and Statistical Analysis

Total and subsets of DRG neurons were counted on lumbar L4 DRG from adult WT and Myo1a KO mice, as described in Gaillard et al., 2014. Briefly, 12 μm serial sections of L4 DRG were distributed on 6 slides which were subjected to different markers, including the pan-neuronal marker PGP9.5. This approach allowed us to refer all countings to the total number of neurons (PGP9.5). For each genotype, three independent experiments were performed. Data are presented as the mean±standard error of the mean (SEM).

GABRA2 Fluorescence Intensity

The intensity of fluorescence (mean florescence of pixels in the region of interest) per $mm^2$ related to GABRA2 expression was determined in the laminae I-III of WT and Myo1a KO SC sections using ImageJ software. For each genotype, three independent experiments were performed and 5-10 SC sections were analyzed and the fold change in the intensity of fluorescence of Myo1a KO versus WT specimens was calculated.

Drugs

SNC80 (Tocris Bioscience) was dissolved in a 100 mM HCl solution, DAMGO (Sigma Aldrich) was dissolved in saline (0.9% NaCl), Baclofen (Sigma Aldrich) was dissolved in $H_2O$ (pH7.6), recombinant human TAFA4 (R&D Systems) was dissolved in saline, Diazepam (DZP, Roche) was dissolved in 10% dimethyl sulfoxide (DMSO)/90% saline, Muscimol (Tocris Bioscience), Taurine (Sigma Aldrich), Bicuculline (Sigma Aldrich) and Pregabalin (Sigma Aldrich) were dissolved in Phosphate Buffer (PB, 50 mM, pH 7.4).

Except for pregabalin, all drugs were administrated via intratechal (i.t) injection. The dosages are indicated in the figure legends. Pregabalin was injected intra-peritoneally (i.p). Response to mechanical stimulations was recorded 30 min up to 6 h after drug administration as indicated in the figure legends.

Behavioral Tests and Statistical Analysis

All behavioral analyses were conducted on 8-12 weeks old Myo1a KO and WT males. All experiments were carried at room temperature (~22° C.). Animals were acclimated for one hour to their testing environment prior to all experiments. Experimenters were blind to the genotype of the mice during testing. The number of tested animals is indicated in the figure legends section. All error bars represent SEM. All statistical analysis was carried using Two Way Repeated Measures ANOVA followed by Bonferroni's post-hoc test. *Openfield, Rotarod, Hot plate* and *Formalin* tests were carried as described in Gaillard et al., 2014 (Gaillard et al., 2014).

Acetone Test

Acetone drop evaporation assay (Hulse et al., 2012) was used to assess naïve mice sensitivity to innocuous skin cooling. A drop of acetone was applied on the left hind paw using a 1 ml syringe. The duration of flinching/pain like behavior (seconds) was recorded immediately following acetone application for a total period of 2 minutes. The test was repeated twice and the mean duration of flinching/pain behavior was calculated.

Heat Hypersensitivity

Hind paw heat hypersensitivity was determined prior and after carrageenan inflammation as well as after paw incision surgery, using Hargreaves test, as described in Gaillard et al., 2014. For the carrageenan inflammatory pain model, the test was performed at several time points (see legend) starting from one day and up to 60 days after inflammation. For the paw incision pain model, the test was performed at several time points (see legend) starting from one day and up to 30 days after inflammation.

Mechanical Thresholds

Mechanical thresholds of the plantar surface were determined using Von Frey's filaments with the up-down method (Chaplan et al., 1994), previously as described (Gaillard et al., 2014) prior to and at several time-points after inflammation, neuropathy and paw-incision surgery.

Injury-Induced Pain Models

Carrageenan and Zymosan-A Induced Inflammation

20 µl of a solution containing 1% carrageenan in $H_2O$ (weight/vol, Sigma) or 20 µl of a solution containing 0.06 mg Zymosan-A in 0.9% NaCl (weight/vol, Sigma), were injected subcutaneously into the plantar side of the left hindpaw, using a 30 G needled syringe.

For carrageenan-induced inflammation, mechanical thresholds were determined prior to inflammation and at several time-points (see legend) starting from 1 hour and up to 60 days after inflammation. For zymosan inflammation, mechanical thresholds were measured prior to injection, at day 1 and at several time-points (see legend) up day 60. In addition, mechanical thresholds in the zymosan model were measured before inflammation, at day 1 and day 2, before and after drug administration.

Chronic Constriction Injury (CCI)

Unilateral peripheral mono-neuropathy was induced in ketamin/xylasin-anesthetized mice by performing three loosely tied ligatures (with about 1 mm spacing) around the common sciatic nerve (Bennett and Xie, 1988) using monocryl resorbable suture filaments (6-0, Ethicon, Piscataway, N.J., USA). The nerve was constricted to a barely discernable degree, so that circulation through the epineurial vasculature was not interrupted. After surgery, the animals were allowed to recover in a warming chamber, and then they were returned to their home cages. Mechanical thresholds were measured before CCI and at several time-points (see legend) starting from 3 day and up to 60 days after surgery.

Paw Incision

The paw incision pain model was performed as described in Brennan (1999). Briefly, mice were anesthetised with ketamin/xylasin and a 5 mm longitudinal incision of the plantar face of the right hindpaw, starting from 2-5 mm from the proximal edge of the heel was performed. The plantar muscle was then carefully elevated with forceps and incised longitudinally with a blade, while leaving muscle's origins intact. The wound was closed with one horizontal mattress suture using 6.0 silk monofilament (Ethicon, Piscataway, N.J., USA) and the wound site was covered with betadine ointment. After surgery, the animals were allowed to recover in a warming chamber, and returned to their home cages. Mechanical thresholds were determined prior to and up to 60 days after surgery (see legend) starting from 6 hours post-injury.

Spared-Nerve Injury (SNI)

Spared nerve injury surgery was performed as described (Shields et al., 2003). Briefly, mice were anesthetized with a mix of ketamine/xylazine and an incision was made through the skin and thigh muscle at the level of the trifurcation of the sciatic nerve. The common sural and peroneal nerves were ligated using a 6.0 silk filament (Ethicon, Piscataway, N.J., USA) and transected, while leaving the tibial nerve intact. After surgery, the animals were allowed to recover in a warming chamber, and then they were returned to their home cages. Mechanical thresholds were determined at days 7, 9 and 14 post-surgery, before and after drug administration.

RNA Extraction

Mice were deeply anesthetized with a mix of ketamine/xylazine and transcardially perfused with 5-10 mL RNA Later (Qiagen). L3 to L5 DRGs and SC were rapidly dissected and RNA was extracted by using RNeasy Micro Kit (Qiagen), according to manufacturer's instructions. For quality control, RNAs were loaded on a RNA NanoChip (Agilent) and processed with 2100 Bioanalyzer system (Agilent technology).

High-Throughput Sequencing and Analyses

WT and Myo1a KO DRG and SC RNAs were extracted in experimental duplicates from 2-3 mice each. RNA-seq libraries were prepared using the TruSeq RNA Sample Preparation Kit (Illumina). All libraries were validated for concentration and fragment size using Agilent DNA1000 chips. Sequencing was performed on a HiSeq 2000 (Illumina), base calling performed using RTA (Illumina) and quality control performed using FastQC (FASTQC, 2010) and RSeQC (Wang et al., 2012). Sequences were uniquely mapped to the mm10 genome using Subread (Liao et al., 2013) (C version 1.4.6-p2) using default values. Reads mapping to gene exons (GRCm38.p4 gene assembly) were counted using featureCounts (Liao et al., 2014) (C version 1.4.6-p2). Differential gene expression was performed using exon counts from biological replicates using the DESeq2 BioConductor R package (Love et al., 2014), using a 5% false discovery rate (FDR) cutoff.

qRT-PCR

RNA obtained from each sample was converted into cDNA using Superscript III Reverse Transcriptase (Invitrogen). Gene expression was assessed by quantitative PCR (qPCR), using qPCR Sybr-Green master mix (ThermoFisher). Samples were run for 40 cycles on a StepOne qPCR apparatus (Applied Biosystems). The relative quantity of transcripts encoding each gene was determined by normalization to β-actin using the standard $\Delta Ct$ or $\Delta \Delta Ct$ method.

All experiments were performed in triplicates and data represent the fold change (mean±SEM) in transcript expression level of Myo1a KO versus WT. The primers sequences used for qPCR are:

```
Myo1a F:
                       (SEQ ID NO: 18)
CTACGAGCAGCTTCCCATCT,
Myo1a R:
                       (SEQ ID NO: 19)
CCACATTTGCCAAAGCATAG,

Gabra2 F:
                       (SEQ ID NO: 20)
ACAAAAAGAGGATGGGCTTG,
Gabra2 R:
                       (SEQ ID NO: 21)
TCATGACGGAGCCTTTCTCT, Wfdy1 F:
                       (SEQ ID NO: 22)
AAAGGCCGGACACTCCTC,
Wdfy1 R:
                       (SEQ ID NO: 23)
TGAGCTGCAGGTAGCACAGT,
```

-continued

Nnt F:
(SEQ ID NO: 24)
CCTGGTGGCACCTTCGTA,

Nnt R:
(SEQ ID NO: 25)
CTGAGCCCAGGTACATGATTT.

DRG Neuron Dissociation and Culture

Adult WT, Myo1a KO, WT:Tafa4$^{+/Venus}$ and Myo1a KO: Tafa4$^{+/Venus}$ mice were deeply anesthetized (ketamine/xylazine) and DRGs were rapidly dissected, collected in ice-cold HBSS-glu (HBSS 1×(Gibco), 0.1M D-glucose (Sigma), 50 mM HEPES (Gibco), ph7,4) and subjected twice to enzymatic digestion using 2 mg/ml type 1 collagenase (Gibco) and 5 mg/ml dispase (both from Gibco) for 20 min at 37° C. DRGs were washed twice with HBSS-glu and resuspended in NBc medium (NBc: Neurobasal (Gibco), 1% (v/v) B27 (Gibco), 1000 U/ml penicillin (Invitrogen), 1000 µg/ml streptomycin (Invitrogen)). Single cell suspensions were obtained by passages through 3 needle tips of decreasing diameter (gauge 18, 21, 26). Cells were plated on polyornithin-laminin coated dishes and kept at 37° C. for 1-2 hours before adding 10 ng/ml Neurotrophin 4 (NT4, Peprotech) and 2 ng/ml glial cell line-derived neurotrophic factor (GDNF, Invitrogen). C-LTMRs were identified through to live Venus fluorescence and Aδ-LTMRs were identified thanks to their "rosette"-like morphology (Dubreuil et al, 2004). Patch-Clamp recordings were performed 18-30 h after plating.

Electrophysiology on Cultured DRGs

Electrophysiological recordings were performed using an Axopatch 200B amplifier. Data were analyzed by pCLAMP 10.5 (Molecular Devices).

Whole Cell Recordings of C-LTMRs and Aδ-LTMRs

Patch-clamp recordings of cultured C-LTMRs were performed with 1 to 2 MΩ pipettes filled with a KCl-based solution containing (in mM): 134 KCl, 1 MgCl$_2$, 4.8 CaCl$_2$, 10 HEPES, 4 Mg-ATP, 0.4 Na-GTP and 10 EGTA (pH 7.3). Patch clamp recordings of cultured Aδ-LTMRs were performed with 1 to 3 MΩ pipettes filled with a KCl-based solution containing (in mM): 105 K Aspartate, 10 NaCl, 27 KCl, 4 Mg-ATP, 0.4 Na-GTP, 5 Creatine-Phosphate (sodium salt), 1 CaCl$_2$, 10 EGTA, 1 MgCl$_2$, 10 HEPES (pH 7.2 with KOH, ≈329 mOsm).

Neurons were perfused at a flow rate of 2-3 ml/min with standard external solution containing (in mM): 140 NaCl, 4 KCl, 2 MgCl$_2$, 2 CaCl$_2$, 10 HEPES and 10 glucose (pH 7.4).

Stock solution of the GABA$_A$ receptor agonist, Muscimol (Tocris Bioscience) was prepared in water and dissolved in the external solution at the desired concentration. Muscimol was applied in the bath for 10 s.

Mechanical-Activated Currents

Mechanical stimulation has been realized with a sealed, fire-polished glass micropipette attached to a piezo-electric actuator (Step Driver PZ-150 M; Burleigh) that was positioned at an angle of 45 degrees from horizontal and used as mechanical probe. Downward movement of the probe toward the cell was driven by pClamp software (Molecular Devices). Voltage-clamped mechano-activated currents were recorded at a holding potential of −60 mV with the same solutions as for whole patch clamp recordings of Aδ-LTMRs. Baseline for mechanical stimulation was defined in µm as the distance of probe displacement inducing a mechano-activated current minus 0.5 µm.

Whole-Cell Patch-Clamp Recording from Spinal Cord Slices with Attached Dorsal Root Transverse spinal cord slices with attached dorsal roots from juvenile (P24 to P45) Myo1a KO and WT mice were prepared for whole-cell recording. Briefly, the animals were anesthetized using Pentobarbital (200 mg/kg), perfused with ice cold oxygenated low calcium artificial cerebrospinal fluid (ACSF; in mM: NaCl 101; KCl 3.8; MgCl$_2$ 18.7, MgSO$_4$ 1.3; KH$_2$PO$_4$ 1.2; HEPES 10; CaCl$_2$ 1; Glucose 1), and then beheaded. The vertebral column and surrounding muscles were quickly removed and immersed in ice cold oxygenated ACSF. Following laminectomy, the spinal cord was gently removed and its lumbar part was placed into a small 3% agarose block. Spinal slices (300 µm thick) were cut using a Leica VTS1000 vibratome, and transferred in warm (31° C.) ACSF (in mM: NaCl 130.5; KCl 2.4; CaCl2 2.4; NaHCO$_3$ 19.5; MgSO$_4$ 1.3; KH$_2$PO$_4$ 1.2; HEPES 1.25; glucose 10; pH 7.4) equilibrated with 95%02-5% CO2 for at least one hour before starting patch clamp recordings. Spinal slices were placed in a recoding chamber bathed with warmed (31° C.) ACSF Electrophysiological measurements were performed under the control of an Olympus BX51 microscope using a multiclamp 2B (Molecular devices). Patch pipettes (7-11Ω) were filled with C-based pipette solution (in mM: CsMethaneSulfonate 120; CsCl 20; CaCl2 0.1; MgCl2 1.3; EGTA 1; HEPES 10; GTP 0.1; cAMP 0.2; Leupeptin 0.1; Na2ATP 3; D-Manitol 77; pH 7.3). A glass suction electrode connected to a Master 8 (A.M.P. Instrument Ltd) stimulator was used to stimulate dorsal roots. Typically, a pair of high duration (500 µs) high intensity stimulations (350 µA) was used to recruit most primary afferent fibers in the recorded slice. All drugs were purchased from Sigma. Statistical comparison of EPSC frequencies was assessed for each cell using Kolmogorov-Smirnov test.

Results

Injury-Induced Acute Mechanical Pain is Converted into Chronic Pain in Myo1a KO Mice.

In a recent study, inventors identified Myo1a to be highly enriched in adult C-LTMRs (Reynders et al., 2015). Co-expression analysis showed that Myo1a was indeed expressed in GINIP$^+$/IB4$^−$ C-LTMRs (FIG. 1A), but its expression also occurred in Aδ LTMRs marked by TrkB and in a subset of Aβ Ret$^+$ LTMRs (FIGS. 1B and 1C), and totally excluded from peptidergic TrkA$^+$ and proprioceptive TrkC$^+$ neurons (data not shown). At the developmental level, Myo1a is expressed in a subset of large DRG neurons at E15 (FIG. 1D) and its expression extends to the majority of DRG neurons at birth (FIG. 1E). Myo1a level of expression in SC during development and in adult is almost undetectable as confirmed by in situ hybridization and q-RT-PCR (FIGS. 1D-G).

To gain insights into the role of MYO1A in sensory physiology, inventors sought to analyze Myo1a KO mice (Tyska et al., 2005). These mice are viable, fertile and most of the perturbations described were related to the intestine biology where this atypical myosin protein is highly expressed (Kravtsov et al., 2012; Mazzolini et al., 2012). However nothing was known about the role of MYO1A in the somatosensory system.

To test whether loss of MYO1A altered DRG neurons development, inventors performed a series of quantitative and qualitative analyses. They found no difference in the total number of lumbar DRG neurons or in the number of TrkA$^+$, TrkB$^+$, TrkC$^+$, Ret$^+$ and TH$^+$ neurons between WT and Myo1a KO mice (FIGS. 5A and 5B). At the anatomical level, double and triple staining experiments on SC sections showed that peptidergic CGRP and the subset of nonpeptidergic GINIP+ afferents displayed normal central projections to their respective laminae in the dorsal horn of the SC (FIGS. 5C-E). Peripherally, PGP9.5 and S100 staining revealed normal peripheral target innervation of all DRG neurons and hair follicles-innervating LTMRs (FIGS. 5F and 1G). Finally, to test whether loss of MYO1A affected neuronal excitability of DRG neurons, inventors performed patch-clam recordings on cultured C-LTMRs and D-hair Aδ mechanoreceptors. The C-LTMRs were visualized by crossing Myo1a KO mice with Tafa4$^{Venus}$ mice and the D-hair neurons were identified by their rosette-like shape. In both types of neurons, there were no differences between the two genotypes in passive and intrinsic electrical properties (FIGS. 6A-G). Furthermore, they found no difference in the sensitivity of cultured D-hair neurons from WT and Myo1a KO mice to a piezo-driven mechanical stimulation (FIGS. 6H and 6I). Together these data demonstrate that MYO1A is dispensable for the survival, the molecular maturation, the anatomical organization and the electrophysiological properties of DRG neurons.

To gain insights into the role of MYO1A in somatosensation, inventors subjected Myo1a KO mice to a large battery of somatosensory tests under acute and injury conditions. Myo1a KO mice had normal behavior in the open filed and rotarod tests (FIGS. 7A-C), they exhibited no difference in their ability to sense noxious heat stimuli in the hot plate test and displayed normal response to the acetone test (FIGS. 7D and 7E). They then tested the mechanical sensitivity of their mice under acute and 3 different pathological conditions: Carrageenan-induced inflammation, the chronic constriction injury model (CCI) (Bennett and Xie, 1988), and the Brennan test (Brennan, 1999). Mechanical sensitivity was tested using the up-down method at basal conditions and at several time points after injury (FIGS. 1F-H). In all three paradigms mechanical thresholds at baseline levels were similar between the two genotypes (FIGS. 1F-H). Intraplantar injection of carrageenan induced a massive drop in mechanical thresholds in both genotypes starting at one hour post-inflammation (FIG. 1F). Impressively, three days post-inflammation, WT mice returned to baseline levels, whereas mechanical hypersensitivity was prolonged as long as 60 days post-inflammation in Myo1a KO mice, demonstrating that an acute and reversible inflammation-induced mechanical pain is converted into a long lasting and irreversible chronic pain. The same behavioral responses were observed in the nerve injury and in the postoperative models. Significant reversal of CCI-induced mechanical hypersensitivity started at day 30 and returned to baseline levels around day 40 in the WT mice, whereas, as in the Carrageenan-induced inflammation, mechanical hypersensitivity in the Myo1a KO mice persisted for as long as 60 days post-CCI (FIG. 1G). Finally, in the Brenan test, incision-induced mechanical hypersensitivity was irreversible in the Myo1a KO mice, whereas it lasted for less than 10 days in the WT mice (FIG. 1H). Thermal hypersensitivity was assessed in the Carrageenan and in the Brenan paradigms using the Hargreaves test. In the Carrageenan model, thermal hypersensitivity was prolonged in Myo1a KO mice but returned to baseline levels at day 60 post-inflammation (FIG. 7G). However, in the Brenan model there was no difference between WT and Myo1a KO mice in the post-surgical-induced thermal hypersensitivity (FIG. 7H). Finally, Myo1a KO mice exhibited a significant enhancement of formalin-evoked nocifensive behavior during both phases (FIG. 7F). Together, these data demonstrate that Myo1a KO mice are predisposed to develop injury-induced chronic mechanical pain and suggest that these mice can be used as an excellent model system to decipher the mechanisms that trigger the transition from acute to chronic pain.

Loss of MYO1A Specifically Alters the Ionotropic GABAergic Signaling

It is well established that injury-induced chronic pain is caused by an imbalance between the excitatory and inhibitory neurotransmission in the SC, and that the concurrent exaggerated pain can be transiently reversed by a variety of compounds such as opioid, GABA and glycine receptors agonists, calcium channels antagonists and inventors' recently identified TAFA4. To unravel which of these signaling pathways are dysfunctional in Myo1a KO mice, inventors tested the analgesic effect of these compounds using the spared nerved injury (SNI) neuropathic pain model (Decosterd and Woolf, 2000). The SNI model was chosen because it's highly reproducible and also induces a long lasting and irreversible mechanical pain. Using this paradigm, they showed that intrathecal (IT) administration of delta and mu opioid receptors agonists SNC80 and DAMGO (FIG. 2A), $GABA_B$ receptor agonist baclofen and TAFA4 (FIG. 2B), α2δ voltage gated calcium channel inhibitor pregabalin and the glycine receptor agonist taurine (FIG. 3C) significantly reversed SNI-induced mechanical hypersensitivity in both genotypes. However, in contrast to WT mice, IT administration of the $GABA_A$ agonist muscimol completely failed to reverse SNI-induced mechanical pain in Myo1a KO mice (FIG. 2D). Myo1a KO mice resistance to the analgesic effect of muscimol was also confirmed in the zymosan A-induced inflammatory pain model (Witschi et al., 2011). Inventors first showed that zymosan-induced inflammation also resulted in a prolonged and irreversible mechanical hypersensitivity in Myo1a KO mice (FIG. 2E). IT administration of muscimol or the $GABA_A$-Rs positive allosteric modulator diazepam (DZP) strongly reversed zymosan-induced mechanical hypersensitivity in WT mice but had no effect on Myo1a KO mice (FIGS. 2F and 2G). Importantly, injection of SNC80 strongly reversed the mechanical pain in both genotypes (FIG. 2H). Together, these data demonstrate that Myo1a KO mice predisposition to develop injury-induced chronic mechanical pain is due to a selective impairment of the ionotropic GABAergic inhibitory neurotransmission.

Loss of MOY1A Resulted in a Selective Upregulation of GABRA2 Both in DRG and SC Neurons It is well established that loss of GABAergic inhibition may be altered by several means both in peripheral and central nervous systems. These include altered subunit composition of $GABA_A$-Rs, altered levels of GABA, GABA release probability and the speed of its removal from the synaptic cleft, and change in chloride gradient that switches GABA-mediated inhibition into excitation (Sandkuhler, 2009). In order to unravel which of these mechanisms are affected in Myo1a KO mice we used an unbiased RNA deep sequencing screen. Biological replicates of polyA mRNA prepared from DRG and SC neurons of WT and Myo1a KO mice were subjected to high-throughput sequencing to very high sequencing depth (an average of $112\times10^6$ exome-mapped reads per replicate), representing an average 250× whole-exome coverage (Table 1).

TABLE 1

Summary of read mappings from RNA-seq of polyA mRNA prepared from DRG and SC of WT and Myo1a KO mice.

| Sample | Number of mm10-mapped reads | Number of GRCm38 exome reads | Exome coverage |
|---|---|---|---|
| DRG WT Rep1 | 122510851 | 106555838 | 245 |
| DRG WT Rep2 | 140298326 | 123170138 | 283 |
| SC WT Rep1 | 135383211 | 101181431 | 269 |
| SC WT Rep2 | 144363915 | 111158063 | 270 |
| DRG KO Rep1 | 135001904 | 117077396 | 232 |
| DRG KO Rep2 | 134291994 | 117408042 | 255 |
| SC KO Rep1 | 114549363 | 85518826 | 196 |
| SC KO Rep2 | 172249718 | 134362629 | 309 |

Highly significant differentially expressed (DE) genes upon loss of Myo1a expression were called (<5% FDR; <p 0.00025), resulting in the identification of 98 DE genes in DRG neurons (FIG. 3A and Table 2), and 32 DE genes (FIG. 3A and Table 3) in SC neurons.

TABLE 2

Differentially expressed genes in DRG of Myo1a KO vs WT mice.

| ENSEMBL ID | Gene Symbol | Base Mean Counts | Fold Change (log2) | P value | FDR |
|---|---|---|---|---|---|
| ENSMUSG00000073643 | Wdfy1 | 5136 | 1.4483 | 1.50E−100 | 2.83E−96 |
| ENSMUSG00000025401 | Myo1a | 5484 | 1.0095 | 1.23E−52 | 1.16E−48 |
| ENSMUSG00000000560 | Gabra2 | 7946 | 0.9382 | 2.66E−39 | 1.67E−35 |
| ENSMUSG00000097971 | | 2742 | 0.8108 | 2.95E−25 | 7.95E−22 |
| ENSMUSG00000106106 | | 148956 | 0.8048 | 1.19E−26 | 4.49E−23 |
| ENSMUSG00000025453 | Nnt | 2624 | 0.7605 | 1.98E−24 | 4.15E−21 |
| ENSMUSG00000030218 | Mgp | 5295 | 0.7179 | 1.54E−21 | 2.91E−18 |
| ENSMUSG00000029994 | Anxa4 | 3385 | 0.6051 | 2.34E−16 | 3.40E−13 |
| ENSMUSG00000096768 | Erdr1 | 1546 | 0.5945 | 5.44E−15 | 6.42E−12 |
| ENSMUSG00000063796 | Slc22a8 | 924 | 0.5634 | 2.67E−15 | 3.36E−12 |
| ENSMUSG00000068735 | Trp53i11 | 2239 | 0.5412 | 2.84E−12 | 2.82E−09 |
| ENSMUSG00000076258 | | 91347 | 0.5395 | 4.55E−26 | 1.43E−22 |
| ENSMUSG00000026051 | 1500015O10Rik | 1291 | 0.5024 | 6.81E−11 | 5.36E−08 |
| ENSMUSG00000039323 | Igfbp2 | 1958 | 0.4813 | 8.38E−10 | 6.33E−07 |
| ENSMUSG00000025479 | Cyp2e1 | 683 | 0.4812 | 1.80E−11 | 1.54E−08 |
| ENSMUSG00000035299 | Mid1 | 1810 | 0.4674 | 2.01E−09 | 1.46E−06 |
| ENSMUSG00000033174 | Mgll | 16530 | 0.4672 | 9.92E−19 | 1.56E−15 |
| ENSMUSG00000067786 | Nnat | 3299 | 0.4433 | 1.55E−08 | 9.73E−06 |
| ENSMUSG00000035202 | Lars2 | 73887 | 0.4406 | 1.58E−24 | 3.72E−21 |
| ENSMUSG00000096887 | Gm20594 | 2825 | 0.4329 | 8.18E−09 | 5.51E−06 |
| ENSMUSG00000052957 | Gas1 | 2350 | 0.4325 | 3.22E−08 | 1.84E−05 |
| ENSMUSG00000086324 | | 10780 | 0.3914 | 8.20E−12 | 7.37E−09 |
| ENSMUSG00000050010 | Shisa3 | 3037 | 0.3892 | 6.50E−07 | 0.000306659 |
| ENSMUSG00000030310 | Slc6a1 | 2324 | 0.3826 | 1.06E−06 | 0.00047432 |
| ENSMUSG00000076281 | | 11261 | 0.3769 | 9.76E−09 | 6.35E−06 |
| ENSMUSG00000024990 | Rbp4 | 925 | 0.3703 | 6.33E−08 | 3.51E−05 |
| ENSMUSG00000024610 | Cd74 | 16282 | 0.3662 | 4.00E−11 | 3.28E−08 |
| ENSMUSG00000095304 | Plac9a | 2818 | 0.3574 | 3.65E−06 | 0.001437537 |
| ENSMUSG00000034353 | Ramp1 | 353 | 0.3540 | 7.15E−08 | 3.86E−05 |
| ENSMUSG00000003949 | H1f | 2753 | 0.3461 | 1.01E−05 | 0.003815587 |
| ENSMUSG00000070867 | Trabd2b | 670 | 0.3439 | 6.03E−07 | 0.000292135 |
| ENSMUSG00000026062 | Slc9a2 | 691 | 0.3367 | 1.47E−06 | 0.00062906 |
| ENSMUSG00000024650 | Slc22a6 | 533 | 0.3353 | 2.51E−08 | 21.53E−05 |
| ENSMUSG00000021136 | Smoc1 | 2669 | 0.3300 | 2.58E−05 | 0.008398485 |
| ENSMUSG00000018459 | Slc13a3 | 1856 | 0.3298 | 1.99E−05 | 0.006818336 |
| ENSMUSG00000046402 | Rbp1 | 1715 | 0.3195 | 2.10E−05 | 0.007083368 |
| ENSMUSG00000026904 | Slc4a10 | 1783 | 0.3177 | 3.36E−05 | 0.010570455 |
| ENSMUSG00000088609 | | 1505 | 0.3136 | 6.23E−05 | 0.016789981 |
| ENSMUSG00000053279 | Aldh1a1 | 1808 | 0.3118 | 6.94E−05 | 0.018120573 |
| ENSMUSG00000045573 | Penk | 1389 | 0.3107 | 7.10E−05 | 0.018120573 |
| ENSMUSG00000037820 | Tgm2 | 2261 | 0.3101 | 5.00E−05 | 0.01392036 |
| ENSMUSG00000009687 | Fxyd5 | 2354 | 0.3098 | 6.50E−05 | 0.017271687 |
| ENSMUSG00000030862 | Cpxm2 | 986 | 0.3098 | 3.83E−05 | 0.11660881 |
| ENSMUSG00000035000 | Dpp4 | 537 | 0.3094 | 7.29E−07 | 0.000335707 |
| ENSMUSG00000040055 | Gjb6 | 917 | 0.3094 | 3.65E−06 | 0.001437537 |
| ENSMUSG00000030351 | Tspan11 | 1267 | 0.3076 | 3.96E−05 | 0.011853792 |
| ENSMUSG00000017897 | Eya2 | 1715 | 0.3068 | 9.01E−05 | 0.021259308 |
| ENSMUSG00000042436 | Mfap4 | 782 | 0.3040 | 3.51E−05 | 0.010876582 |
| ENSMUSG00000030717 | Nupr1 | 958 | 0.2989 | 9.87E−05 | 0.022729069 |
| ENSMUSG00000095079 | | 473 | 0.2989 | 3.15E−08 | 1.84E−05 |
| ENSMUSG00000040569 | Slc26a7 | 992 | 0.2974 | 5.01E−05 | 0.01392036 |
| ENSMUSG00000033152 | Podxl2 | 4785 | 0.2956 | 1.38E−0.5 | 0.004833264 |
| ENSMUSG00000037166 | Ppp1r14a | 1716 | 0.2954 | 0.000149427 | 0.032427353 |
| ENSMUSG00000074634 | Gm7120 | 1731 | 0.2919 | 0.000192622 | 0.038281175 |

TABLE 2-continued

Differentially expressed genes in DRG of Myo1a KO vs WT mice.

| ENSEMBL ID | Gene Symbol | Base Mean Counts | Fold Change (log2) | P value | FDR |
|---|---|---|---|---|---|
| ENSMUSG00000029163 | Emilin1 | 928 | 0.2901 | 0.000139094 | 0.03053603 |
| ENSMUSG00000056174 | Col8a2 | 1923 | 0.2885 | 0.000179303 | 0.036013163 |
| ENSMUSG00000032334 | Loxl1 | 1376 | 0.2869 | 0.000153495 | 0.03256157 |
| ENSMUSG00000040170 | Fmo2 | 1928 | 0.2863 | 0.00024733 | 0.047348949 |
| ENSMUSG00000004885 | Crabp2 | 688 | 0.2843 | 2.88E−05 | 0.00921269 |
| ENSMUSG00000042190 | Cmklr1 | 542 | 0.2839 | 8.89E−05 | 0.021259308 |
| ENSMUSG00000062515 | Fabp4 | 836 | 0.2773 | 2.22E−05 | 0.007350468 |
| ENSMUSG00000040938 | Slc16a11 | 249 | 0.2724 | 3.57E−06 | 0.001437537 |
| ENSMUSG00000025784 | Clec3b | 748 | 0.2704 | 8.47E−05 | 0.020760793 |
| ENSMUSG00000022595 | Lypd2 | 551 | 0.2658 | 0.000246368 | 0.047648949 |
| ENSMUSG00000039004 | Bmp6 | 1187 | 0.2634 | 0.000161683 | 0.033837805 |
| ENSMUSG00000066687 | Zbtb16 | 822 | 0.2630 | 4.37E−05 | 0.12694785 |
| ENSMUSG00000041598 | Cdc42ep4 | 7427 | 0.2581 | 8.96E−05 | 0.021259308 |
| ENSMUSG00000021943 | Gdf10 | 518 | 0.2573 | 0.000115563 | 0.025974121 |
| ENSMUSG00000030278 | Cidec | 367 | 0.2471 | 1.15E−05 | 0.004174341 |
| ENSMUSG00000033152 | Podxl2 | 4785 | 0.2956 | 1.38E−05 | 0.004833264 |
| ENSMUSG00000037166 | Ppp1r14a | 1716 | 0.2954 | 0.000149427 | 0.032427353 |
| ENSMUSG00000074634 | Gm7120 | 1731 | 0.2919 | 0.000192622 | 0.038281175 |
| ENSMUSG00000029163 | Emilin1 | 928 | 0.2901 | 0.000139094 | 0.03053603 |
| ENSMUSG00000056174 | Col8a2 | 1923 | 0.2885 | 0.000179303 | 0.036013163 |
| ENSMUSG00000032334 | Loxl1 | 1376 | 0.2869 | 0.000153495 | 0.03256157 |
| ENSMUSG00000040170 | Fmo2 | 1928 | 0.2863 | 0.00024733 | 0.047348949 |
| ENSMUSG00000004885 | Crabp2 | 688 | 0.2843 | 2.88E−05 | 0.00921269 |
| ENSMUSG00000042190 | Cmklr1 | 542 | 0.2839 | 8.89E−05 | 0.021259308 |
| ENSMUSG00000062515 | Fabp4 | 836 | 0.2773 | 2.22E−05 | 0.007350468 |
| ENSMUSG00000040938 | Slc16a11 | 249 | 0.2724 | 3.57E−06 | 0.001437537 |
| ENSMUSG00000025784 | Clec3b | 748 | 0.2704 | 8.47E−05 | 0.020760793 |
| ENSMUSG00000022595 | Lypd2 | 551 | 0.2658 | 0.000246368 | 0.047648949 |
| ENSMUSG00000039004 | Bmp6 | 1187 | 0.2634 | 0.000161683 | 0.033837805 |
| ENSMUSG00000066687 | Zbtb16 | 822 | 0.2630 | 4.37E−05 | 0.12694785 |
| ENSMUSG00000041598 | Cdc42ep4 | 7427 | 0.2581 | 8.96E−05 | 0.021259308 |
| ENSMUSG00000021943 | Gdf10 | 518 | 0.2573 | 0.000115563 | 0.25974121 |
| ENSMUSG00000030278 | Cidec | 367 | 0.2471 | 1.15E−05 | 0.004174341 |
| ENSMUSG00000048373 | Fgfbp1 | 344 | 0.2441 | 1.37E−05 | 0.004833264 |
| ENSMUSG00000065037 | Rn7sk | 263 | 0.2439 | 2.69E−06 | 0.001128964 |
| ENSMUSG00000036256 | Igfbp7 | 12145 | 0.2434 | 7.10E−05 | 0.018120573 |
| ENSMUSG00000027447 | Cst3 | 35343 | 0.2354 | 5.12E−07 | 0.000261486 |
| ENSMUSG00000079507 | H2-Q1 | 249 | 0.2312 | 4.37E−05 | 0.012694785 |
| ENSMUSG00000026879 | Gsn | 56839 | 0.2300 | 3.81E−06 | 0.001466965 |
| ENSMUSG00000025417 | Pip4k2c | 10331 | 0.2280 | 7.92E−05 | 0.19666363 |
| ENSMUSG00000065911 | | 199 | 0.2206 | 1.09E−05 | 0.004034884 |
| ENSMUSG00000027656 | Wisp2 | 241 | 0.2017 | 5.61E−05 | 0.15352478 |
| ENSMUSG00000037185 | Krt80 | 281 | 0.2002 | 0.000169408 | 0.034765482 |
| ENSMUSG00000065824 | | 148 | 0.1683 | 0.000163095 | 0.033837805 |
| ENSMUSG00000045532 | C1ql1 | 210 | 0.1552 | 0.000106576 | 0.024242748 |
| ENSMUSG00000007877 | Tcap | 148 | −0.1666 | 0.000226999 | 0.044643191 |
| ENSMUSG00000038670 | Mybpc2 | 306 | −0.2179 | 7.50E−05 | 0.018874355 |
| ENSMUSG00000040621 | Gemin8 | 460 | −0.2428 | 0.000172846 | 0.0353089631 |
| ENSMUSG00000026950 | Neb | 633 | −0.2461 | 0.000153087 | 0.03256157 |
| ENSMUSG00000029361 | Nos1 | 8545 | −0.2462 | 0.000131891 | 0.02929533 |
| ENSMUSG00000061816 | Myl1 | 304 | −0.2927 | 5.37E−07 | 0.000267047 |
| ENSMUSG00000074217 | 2210011C24Rik | 1767 | −0.3002 | 9.12E−05 | 0.021259308 |
| ENSMUSG00000079316 | Rab9 | 4067 | −0.3168 | 4.63E−05 | 0.13245887 |
| ENSMUSG00000040586 | Ofd1 | 1418 | −0.3790 | 1.09E−06 | 0.000480185 |
| ENSMUSG00000044377 | | 4354 | −0.3974 | 2.42E−07 | 0.00012671 |
| ENSMUSG00000090015 | Gm15446 | 839 | −0.4313 | 3.89E−09 | 2.72E−06 |
| ENSMUSG00000061723 | Tnnt3 | 964 | −0.4816 | 5.81E−13 | 6.45E−10 |
| ENSMUSG00000079317 | Trappc2 | 7140 | −0.4942 | 6.99E−12 | 6.60E−09 |
| ENSMUSG00000025373 | Rnf41 | 11954 | −0.5169 | 1.00E−15 | 1.35E−12 |
| ENSMUSG00000082286 | | 3866 | −0.5219 | 1.19E−12 | 1.24E−09 |
| ENSMUSG00000040565 | Btaf1 | 4110 | −0.6499 | 4.26E−19 | 7.31E−16 |
| ENSMUSG00000056999 | Ide | 13039 | −0.6774 | 1.37E−32 | 6.46E−29 |

TABLE 3

Differentially expressed genes in SC of Myo1a KO vs WT mice.

| ENSEMBL ID | Gene Symbol | Base Mean Counts | Fold Change (log2) | P value | FDR |
|---|---|---|---|---|---|
| ENSMUSG00000073643 | Wdfy1 | 6789 | 1.8765 | 2.26E−100 | 6.80E−96 |
| ENSMUSG00000039253 | Fn3krp | 992 | 1.3973 | 1.48E−38 | 1.49E−34 |
| ENSMUSG00000000560 | Gabra2 | 14817 | 1.2075 | 4.81E−40 | 7.24E−36 |
| ENSMUSG00000025401 | Myo1a | 197 | 0.8047 | 6.00E−17 | 3.01E−13 |
| ENSMUSG00000025453 | Nnt | 3738 | 0.7752 | 4.79E−16 | 1.86E−12 |
| ENSMUSG00000095562 |  | 1577 | 0.6142 | 1.28E−08 | 3.51E−05 |
| ENSMUSG00000090691 |  | 879 | 0.5521 | 2.12E−07 | 0.00042566 |
| ENSMUSG00000025436 | Xrcc6bp1 | 1357 | 0.5228 | 4.04E−07 | 0.000715195 |
| ENSMUSG00000096768 | Erdr1 | 657 | 0.4864 | 3.27E−06 | 0.004691284 |
| ENSMUSG00000090546 | Cdr1 | 29092 | 0.4828 | 4.22E−08 | 9.78E−05 |
| ENSMUSG00000091754 |  | 781 | 0.4448 | 3.45E−05 | 0.034653432 |
| ENSMUSG00000096904 |  | 1088 | 0.4284 | 4.22E−05 | 0.040987861 |
| ENSMUSG00000041773 | Enc1 | 3722 | 0.4158 | 5.83E−06 | 0.007634036 |
| ENSMUSG00000044676 | Zfp612 | 13786 | 0.3611 | 1.04E−05 | 0.12508737 |
| ENSMUSG00000022995 | Enah | 14357 | 0.3407 | 3.20E−05 | 0.033173553 |
| ENSMUSG00000025373 | Rnf41 | 8435 | −0.4051 | 1.14E−05 | 0.013223275 |
| ENSMUSG00000024011 | Pi16 | 2591 | −0.4148 | 5.20E−05 | 0.048885646 |
| ENSMUSG00000000711 | Rab5b | 9824 | −0.4175 | 1.21E−06 | 0.002024553 |
| ENSMUSG00000063681 | Crb1 | 165 | −0.4385 | 1.51E−06 | 0.002400311 |
| ENSMUSG00000025044 | Msr1 | 283 | −0.4410 | 1.22E−05 | 0.013604768 |
| ENSMUSG00000025400 | Tac2 | 1034 | −0.4635 | 1.85E−05 | 0.019871035 |
| ENSMUSG00000044377 |  | 4306 | −0.4653 | 4.67E−06 | 0.00638975 |
| ENSMUSG00000040586 | Ofd1 | 1271 | −0.4771 | 1.04E−05 | 0.012508737 |
| ENSMUSG00000023764 | Sfi1 | 2276 | −0.4851 | 1.70E−06 | 0.002555659 |
| ENSMUSG00000079316 | Rab9 | 3373 | −0.5152 | 2.99E−07 | 0.000563214 |
| ENSMUSG00000031342 | Gpm6b | 193529 | −0.5227 | 1.91E−07 | 0.00041017 |
| ENSMUSG00000079317 | Trappc2 | 11463 | −0.5444 | 1.61E−08 | 4.05E−05 |
| ENSMUSG00000040565 | Btaf1 | 3689 | −0.6525 | 2.85E−12 | 8.59E−09 |
| ENSMUSG00000056999 | Ide | 9557 | −0.6808 | 4.93E−16 | 1.86E−12 |
| ENSMUSG00000023795 |  | 1367 | −0.7991 | 3.97E−14 | 1.33E−10 |
| ENSMUSG00000090015 | Gm15446 | 1500 | −0.8872 | 3.91E−18 | 2.35E−14 |
| ENSMUSG00000082286 |  | 5152 | −1.2830 | 2.63E−38 | 1.98E−34 |

While not surprising that the majority of DE genes were unique to DRG neurons where Myo1a is normally expressed (FIGS. 1A-G), a small number (14) of DE genes were deregulated in both DRG and SC neurons and 18 DE genes were unique to SC neurons (FIGS. 3A and 3B). To confirm the RNA seq data inventors focused on few genes that were differentially expressed in both tissues using quantitative reverse transcription polymerase chain reaction (qRT-PCR). In both tissues, Nnt, Gabra2 and Wdfy1 displayed a highly significant increase in Myo1a KO mice (FIG. 3C). However, inventors were unable to confirm the differential expression of the downregulated genes (data not shown). Myo1a KO mice selective alteration of the ionotropic GABAergic neurotransmission revealed by inventors' behavioral experiments prompted them to focus on Gabra2 gene. Gabra2 was the only GABA receptor subunit that displayed altered expression in Myo1a KO mice (Table 4).

TABLE 4

| $GABA_A$ Subunit | Mean expression level (FPKM) | | | |
|---|---|---|---|---|
|  | DRG | | Spinal cord | |
|  | WT | KO | WT | KO |
| GABRA1 | 3707 | 3710 | 3761 | 3445 |
| GABRA2 | 2271 | 5867 | 4131 | 12799 |
| GABRA3 | 817 | 835 | 7977 | 8092 |
| GABRA4 | 85 | 72 | 2620 | 2589 |
| GABRA5 | 381 | 391 | 5615 | 6421 |
| GABRA6 | 0 | 0 | 8 | 2 |
| GABRB1 | 359 | 417 | 4383 | 4562 |
| GABRB2 | 692 | 601 | 1574 | 1736 |

TABLE 4-continued

| $GABA_A$ Subunit | Mean expression level (FPKM) | | | |
|---|---|---|---|---|
|  | DRG | | Spinal cord | |
|  | WT | KO | WT | KO |
| GABRB3 | 6225 | 6225 | 14167 | 15023 |
| GABRG1 | 2227 | 2082 | 2613 | 2827 |
| GABRG2 | 4193 | 4227 | 8822 | 9244 |
| GABRG3 | 136 | 187 | 656 | 689 |
| GABRD | 34 | 29 | 35 | 48 |
| GABRE | 44 | 38 | 50 | 36 |
| GABRP | 1 | 1 | 6 | 2 |
| GABRQ | 12 | 22 | 365 | 365 |

To complement the qRT-PCR results, they used in situ hybridization and immunohistochemistry. Using in situ hybridization they found that Gabra2 upregulation is much evident in DRG, with a very strong upregulation in large size neurons, than in SC (FIG. 3D). Using immunohistochemistry, they confirmed that Gabra2 upregulation was accompanied by a significant increase in GABRA2 protein in the dorsal horn of SC where primary afferent endings and local interneurons are intermingled (FIGS. 3E and 3F). Importantly, in line with the selective upregulation of GABRA2 (Table 4), they found no difference in the immunoreactivity of GABRA1 (α1 subunit) between the two genotypes (FIG. 3G). Finally, to test whether GABRA2 upregulation impacted $GABA_A$-Rs function, they performed whole-cell patch clamp recordings on cultured WT and Myo1a KO Venus-expressing C-LTMRs. They found that bath application of increasing concentrations of muscimol triggered similar current amplitudes in both genotypes (FIGS. 4A and 4B), demonstrating that GABRA2 upregulation did not alter GABA$_A$-Rs response to its selective agonist muscimol.

Muscimol-Evoked Increase in Excitatory Glutamatergic Activity of Lamina II Interneurons is Severely Impaired in Inflamed Myo1a KO Mice.

In an attempt to provide a rational explanation to the insensitivity of Myo1a KO mice to the analgesic effect of muscimol, inventors used whole cell patch-clamp recordings on SC slices. First, a thorough characterization of a large panel of electrophysiological properties of inner lamina II neurons under acute conditions and after inflammation (Carrageenan and Zymozan) revealed no difference between WT and Myo1a KO mice (FIG. 8). They then investigated the incidence of bath application of muscimol on spontaneous excitatory post-synaptic currents (sEPSC) in laminae II neurons in WT and Myo1a KO mice, under acute conditions and after zymosan inflammation. Under these conditions the overall average amplitude of sEPSC was similar between the two genotypes (data not shown). In naïve WT mice, bath application of 5 µM muscimol induced a significant increase in sEPSC frequency, as indicated by the shift of the sEPSC interval cumulative distribution curve towards the left (FIG. 4C). This effect was almost doubled in slices from WT mice inflamed with zymosan (FIG. 4E). Interestingly, in naïve slices from Myo1a KO mice, muscimol induced a drastic 544% increase in sEPSC frequency (FIG. 4D). However, this effect was completely lost in slices obtained from zymosan inflamed KO mice as bath application of muscimol had no effect on sEPSC frequency (FIG. 4F), further supporting inventors observed insensitivity of Myo1a KO mice to the analgesic effect of muscimol after injury (FIGS. 2D and 2F).

CONCLUSIONS

In these experiments, inventors showed that loss of MYO1A converted an injury-induced acute and reversible pain into a long lasting and irreversible pain. This pain chronicity was selective to mechanical sensitivity in two inflammatory, one neuropathic and one post-operative pain models, suggesting that loss of MYO1A predisposes an individual to develop injury-induced chronic pain and revealing these mice as an ideal animal model to uncover the cellular and molecular mechanisms that trigger the transition from acute to chronic pain. Indeed, inventors found that loss of MYO1A selectively impaired the ionotropic GABAergic signaling as injury-induced mechanical hypersensitivity in Myo1a KO mice could be transiently reversed by opioids, baclofen, pregabalin, TAFA4 and taurine but not by muscimol and diazepam. They also found that loss of MYO1A resulted in a constitutive upregulation of the α2 subunit of GABA$_A$-Rs, suggesting a possible participation of the altered expression of this subunit in the process of injury-induced pain chronicity.

Chronic pain is a serious and highly heterogeneous medical problem with a prevalence varying from 20 to 30% of the world population (Bouhassira et al., 2008; Breivik et al., 2006). Given that only a fraction of individuals develop chronic pain, the contribution of genetic factors has been postulated (Belfer et al., 2015; Devor, 2004; Macrae, 2008; Tegeder et al., 2006; Voscopoulos and Lema, 2010). Here, using four different pain paradigms, inventors showed that Myo1a KO mice developed irreversible chronic pain after injury, demonstrating a causal link between loss of MYO1A and the development of chronic pain. Very importantly, inventors found that loss of one copy of Myo1a gene in Myo1a$^{+/-}$ mice induced a long lasting and irreversible mechanical pain in the setting of inflammation, further supporting a contribution of Myo1a as a predisposition gene to develop injury-induced chronic pain (FIG. 7I).

Using behavioral pharmacology, inventors showed that injury-induced mechanical hypersensitivity could not be reversed in Myo1a KO mice by muscimol. This impaired ionotropic GABAergic signaling was further demonstrated by their electrophysiological recordings in which they showed that under acute conditions, muscimol evoked a drastic increase in the excitatory glutamatergic activity of lamina II interneurons, whereas after inflammation, this effect was completely abolished. They also showed that the selective antagonist of GABA$_A$-Rs biccuculine evoked similar mechanical hypersensitivity in naïve WT and Myo1a KO mice (FIG. 7J), demonstrating that GABA$_A$-Rs are functional in Myo1a KO mice under acute conditions. Together, these data indicate that injury causes a shift of spinal GABA$_A$-Rs from active to inactive state, further silencing the ionotropic GABAergic inhibitory neurotransmission in Myo1a KO mice, thus leading to the development of chronic pain. One plausible explanation to this phenomenon is that injury induces a massive internalization of GABA$_A$-Rs in Myo1a KO mice. Indeed, decreases in synaptic GABA$_A$-Rs, resulting from enhanced endocytosis, have been observed in animals in which the life-threatening refractory convulsive status epilepticus (SE) has been experimentally induced (Naylor et al., 2005; Terunuma et al., 2008). Interestingly, this decrease in surface receptors mainly targets GABA$_A$-Rs containing benzodiazepine-sensitive subunits, which explains both the pharmaco-resistance of SE patients to benzodiazepines and the non-terminating nature of the seizures. Remarkably, inventors demonstrated that under injury conditions, Myo1a KO mice were totally insensitive to muscimol and DZP, and under these same conditions, once the injury-induced mechanical hypersensitivity is established; it becomes irreversible in these mice.

Another possible explanation to the observed phenotype came from inventors' RNA deep sequencing data. They found that loss of MYO1A was accompanied by a massive and selective upregulation of Gabra2 both in DRG and SC neurons at steady state, indicating that this altered expression likely participate to the observed injury-induced pain chronicity. Although they confirmed that gabra2 upregulation resulted in a significant increase in GABRA2 protein, this increase has no effect on the amplitude of muscimol-evoked currents in Myo1a KO CLTMRs. Given that GABRA2 was the only GABA$_A$-Rs subunit to be differentially expressed in DRG and SC neurons, inventors' data suggest that GABRA2 upregulation likely contribute to shifting the balance towards more GABA$_A$-Rs containing α2 subunit. In this case, the α2/α1 ratio will be mainly impacted in large size primary afferent neurons (See FIG. 3D) as α2 and α1 are the main subunits expressed in DRG.

In line with this hypothesis, a recent study demonstrated that patients with refractory convulsive status epilepticus and refractory epilepsy had significantly more α2-containing GABA$_A$-Rs at the expense of α1-containing receptors (Loddenkemper et al., 2014). Future studies exploring whether α2-containing GABA$_A$-Rs are prone to excessive internalization than GABA$_A$-Rs containing other alpha subunits are warranted.

In conclusion, although it did not decipher the precise mechanisms that impair GABA$_A$-Rs function under injury conditions in Myo1a KO mice, inventors describe the first mouse model in which a loss-of-function mutation leads to an irreversible pain state after injury. They also provide strong arguments that Myo1a gene should be seriously considered as a predictive genetic factor for the development of injury-induced chronic pain and points out the ionotropic GABAergic system as the main mechanism that contributes to the transition from acute to chronic pain. Inventors' study also provides a powerful preclinical animal model that can be used (i) to deepen our understanding of the molecular and cellular mechanisms that trigger the transition from acute to chronic pain and (ii) to the design "á la carte" pharmacological therapies to prevent the establishment of chronic pain.

REFERENCES

Ahmadi, S., Lippross, S., Neuhuber, W. L., and Zeilhofer, H. U. (2002). PGE(2) selectively blocks inhibitory glycinergic neurotransmission onto rat superficial dorsal horn neurons. Nat Neurosci 5, 34-40.

Belfer, I., Dai, F., Kehlet, H., Finelli, P., Qin, L., Bittner, R., and Aasvang, E. K. (2015). Association of functional variations in COMT and GCH1 genes with postherniotomy pain and related impairment. Pain 156, 273-279.

Bennett, G. J., and Xie, Y. K. (1988). A peripheral mononeuropathy in rat that produces disorders of pain sensation like those seen in man. Pain 33, 87-107.

Bouhassira, D., Lanteri-Minet, M., Attal, N., Laurent, B., and Touboul, C. (2008). Prevalence of chronic pain with neuropathic characteristics in the general population. Pain 136, 380-387.

Bourane, S., Duan, B., Koch, S. C., Dalet, A., Britz, O., Garcia-Campmany, L., Kim, E., Cheng, L., Ghosh, A., Ma, Q., and Goulding, M. (2015a). Gate control of mechanical itch by a subpopulation of spinal cord interneurons. Science 350, 550-554.

Bourane, S., Grossmann, K. S., Britz, O., Dalet, A., Del Barrio, M. G., Stam, F. J., Garcia-Campmany, L., Koch, S., and Goulding, M. (2015b). Identification of a spinal circuit for light touch and fine motor control. Cell 160, 503-515.

Braathen, G. J., Hoyer, H., Busk, O. L., Tveten, K., Skjelbred, C. F., and Russell, M. B. (2015). Variants in the genes DCTN2, DNAH10, LRIG3, and MYO1A are associated with intermediate Charcot-Marie-Tooth disease in a Norwegian family. Acta neurologica Scandinavica.

Breivik, H., Collett, B., Ventafridda, V., Cohen, R., and Gallacher, D. (2006). Survey of chronic pain in Europe: prevalence, impact on daily life, and treatment. Eur J Pain 10, 287-333.

Brennan, T. J. (1999). Postoperative Models of Nociception. ILAR journal/National Research Council, Institute of Laboratory Animal Resources 40, 129-136.

Chaplan, S. R., Bach, F. W., Pogrel, J. W., Chung, J. M., and Yaksh, T. L. (1994). Quantitative assessment of tactile allodynia in the rat paw. J Neurosci Methods 53, 55-63.

Coull, J. A., Beggs, S., Boudreau, D., Boivin, D., Tsuda, M., Inoue, K., Gravel, C., Salter, M. W., and De Koninck, Y. (2005). BDNF from microglia causes the shift in neuronal anion gradient underlying neuropathic pain. Nature 438, 1017-1021.

Coull, J. A., Boudreau, D., Bachand, K., Prescott, S. A., Nault, F., Sik, A., De Koninck, P., and De Koninck, Y. (2003). Trans-synaptic shift in anion gradient in spinal lamina I neurons as a mechanism of neuropathic pain. Nature 424, 938-942.

Decosterd, I., and Woolf, C. J. (2000). Spared nerve injury: an animal model of persistent peripheral neuropathic pain. Pain 87, 149-158.

Delfini, M. C., Mantilleri, A., Gaillard, S., Hao, J., Reynders, A., Malapert, P., Alonso, S., Francois, A., Barrere, C., Seal, R., et al. (2013). TAFA4, a chemokine-like protein, modulates injury-induced mechanical and chemical pain hypersensitivity in mice. Cell Rep 5, 378-388.

Devor, M. (2004). Evidence for heritability of pain in patients with traumatic neuropathy. Pain 108, 200-201; author reply 202.

Donaudy, F., Ferrara, A., Esposito, L., Hertzano, R., Ben-David, O., Bell, R. E., Melchionda, S., Zelante, L., Avraham, K. B., and Gasparini, P. (2003). Multiple mutations of MYO1A, a cochlear-expressed gene, in sensorineural hearing loss. Am J Hum Genet 72, 1571-1577.

Duan, B., Cheng, L., Bourane, S., Britz, O., Padilla, C., Garcia-Campmany, L., Krashes, M., Knowlton, W., Velasquez, T., Ren, X., et al. (2014). Identification of spinal circuits transmitting and gating mechanical pain. Cell 159, 1417-1432.

Eisenberger, T., Di Donato, N., Baig, S. M., Neuhaus, C., Beyer, A., Decker, E., Murbe, D., Decker, C., Bergmann, C., and Bolz, H. J. (2014). Targeted and genomewide NGS data disqualify mutations in MYO1A, the "DFNA48 gene", as a cause of deafness. Hum Mutat 35, 565-570.

FASTQC (2010). FastQC: A quality control tool for high throughput sequence data v. 0.11.3 Worldwide Website: bioinformatics.bbsrc.ac.uk/projects/fastqc/, 2010).

Foster, E., Wildner, H., Tudeau, L., Haueter, S., Ralvenius, W. T., Jegen, M., Johannssen, H., Hosli, L., Haenraets, K., Ghanem, A., et al. (2015). Targeted ablation, silencing, and activation establish glycinergic dorsal horn neurons as key components of a spinal gate for pain and itch. Neuron 85, 1289-1304.

Gaillard, S., Lo Re, L., Mantilleri, A., Hepp, R., Urien, L., Malapert, P., Alonso, S., Deage, M., Kambrun, C., Landry, M., et al. (2014). GINIP, a Galphai-interacting protein, functions as a key modulator of peripheral GABAB receptor-mediated analgesia. Neuron 84, 123-136.

Gilron, I., Jensen, T. S., and Dickenson, A. H. (2013). Combination pharmacotherapy for management of chronic pain: from bench to bedside. The Lancet Neurology 12, 1084-1095.

Harvey, R. J., Depner, U. B., Wassle, H., Ahmadi, S., Heindl, C., Reinold, H., Smart, T. G., Harvey, K., Schutz, B., Abo-Salem, O. M., et al. (2004). GlyR alpha3: an essential target for spinal PGE2-mediated inflammatory pain sensitization. Science 304, 884-887.

Hulse, R. P., Donaldson, L. F., and Wynick, D. (2012). Differential roles of galanin on mechanical and cooling responses at the primary afferent nociceptor. Mol Pain 8, 41.

Kehlet, H., Jensen, T. S., and Woolf, C. J. (2006). Persistent postsurgical pain: risk factors and prevention. Lancet 367, 1618-1625.

Kravtsov, D. V., Caputo, C., Collaco, A., Hoekstra, N., Egan, M. E., Mooseker, M. S., and Ameen, N. A. (2012). Myosin Ia is required for CFTR brush border membrane trafficking and ion transport in the mouse small intestine. Traffic 13, 1072-1082.

Liao, Y., Smyth, G. K., and Shi, W. (2013). The Subread aligner: fast, accurate and scalable read mapping by seed-and-vote. Nucleic Acids Res 41, e108.

Liao, Y., Smyth, G. K., and Shi, W. (2014). featureCounts: an efficient general purpose program for assigning sequence reads to genomic features. Bioinformatics 30, 923-930.

Loddenkemper, T., Talos, D. M., Cleary, R. T., Joseph, A., Sanchez Fernandez, I., Alexopoulos, A., Kotagal, P., Najm, I., and Jensen, F. E. (2014). Subunit composition of glutamate and gamma-aminobutyric acid receptors in status epilepticus. Epilepsy research 108, 605-615.

Love, M. I., Huber, W., and Anders, S. (2014). Moderated estimation of fold change and dispersion for RNA-seq data with DESeq2. Genome Biol 15, 550.

Macrae, W. A. (2008). Chronic post-surgical pain: 10 years on. Br J Anaesth 101, 77-86.

Mazzolini, R., Dopeso, H., Mateo-Lozano, S., Chang, W., Rodrigues, P., Bazzocco, S., Alazzouzi, H., Landolfi, S., Hernandez-Losa, J., Andretta, E., et al. (2012). Brush border myosin Ia has tumor suppressor activity in the intestine. Proc Natl Acad Sci USA 109, 1530-1535.

Muller, F., Heinke, B., and Sandkuhler, J. (2003). Reduction of glycine receptor-mediated miniature inhibitory postsynaptic currents in rat spinal lamina I neurons after peripheral inflammation. Neuroscience 122, 799-805.

Munro, G., Ahring, P. K., and Mirza, N. R. (2009). Developing analgesics by enhancing spinal inhibition after injury: GABAA receptor subtypes as novel targets. Trends Pharmacol Sci 30, 453-459.

Naylor, D. E., Liu, H., and Wasterlain, C. G. (2005). Trafficking of GABA(A) receptors, loss of inhibition, and a mechanism for pharmacoresistance in status epilepticus. J Neurosci 25, 7724-7733.

Peirs, C., Williams, S. P., Zhao, X., Walsh, C. E., Gedeon, J. Y., Cagle, N. E., Goldring, A. C., Hioki, H., Liu, Z., Marell, P. S., and Seal, R. P. (2015). Dorsal Horn Circuits for Persistent Mechanical Pain. Neuron 87, 797-812.

Petitjean, H., Pawlowski, S. A., Fraine, S. L., Sharif, B., Hamad, D., Fatima, T., Berg, J., Brown, C. M., Jan, L. Y., Ribeiro-da-Silva, A., et al. (2015). Dorsal Horn Parvalbumin Neurons Are Gate-Keepers of Touch-Evoked Pain after Nerve Injury. Cell reports 13, 1246-1257.

Reynders, A., Mantilleri, A., Malapert, P., Rialle, S., Nidelet, S., Laffray, S., Beurrier, C., Bourinet, E., and Moqrich, A. (2015). Transcriptional Profiling of Cutaneous MRGPRD Free Nerve Endings and C-LTMRs. Cell reports.

Reynders, A., Mantilleri, A., Malapert, P., Rialle, S., Nidelet, S., Laffray, S., Beurrier, C., Bourinet, E., and Moqrich, A. (2015). Transcriptional Profiling of Cutaneous MRGPRD Free Nerve Endings and C-LTMRs. Cell reports.

Sandkuhler, J. (2009). Models and mechanisms of hyperalgesia and allodynia. Physiol Rev 89, 707-758.

Shields, S. D., Eckert, W. A., 3rd, and Basbaum, A. I. (2003). Spared nerve injury model of neuropathic pain in the mouse: a behavioral and anatomic analysis. J Pain 4, 465-470.

Tegeder, I., Costigan, M., Griffin, R. S., Abele, A., Belfer, I., Schmidt, H., Ehnert, C., Nejim, J., Marian, C., Scholz, J., et al. (2006). GTP cyclohydrolase and tetrahydrobiopterin regulate pain sensitivity and persistence. Nat Med 12, 1269-1277.

Terunuma, M., Xu, J., Vithlani, M., Sieghart, W., Kittler, J., Pangalos, M., Haydon, P. G., Coulter, D. A., and Moss, S. J. (2008). Deficits in phosphorylation of GABA(A) receptors by intimately associated protein kinase C activity underlie compromised synaptic inhibition during status epilepticus. J Neurosci 28, 376-384.

Tyska, M. J., Mackey, A. T., Huang, J. D., Copeland, N. G., Jenkins, N. A., and Mooseker, M. S. (2005). Myosin-1a is critical for normal brush border structure and composition. Mol Biol Cell 16, 2443-2457. Voscopoulos, C., and Lema, M. (2010). When does acute pain become chronic? Br J Anaesth 105 Suppl 1, i69-85.

Wang, L., Wang, S., and Li, W. (2012). RSeQC: quality control of RNA-seq experiments. Bioinformatics 28, 2184-2185.

Witschi, R., Punnakkal, P., Paul, J., Walczak, J. S., Cervero, F., Fritschy, J. M., Kuner, R., Keist, R., Rudolph, U., and Zeilhofer, H. U. (2011). Presynaptic alpha2-GABAA receptors in primary afferent depolarization and spinal pain control. J Neurosci 31, 8134-8142.

Zeilhofer, H. U., Wildner, H., and Yevenes, G. E. (2012). Fast synaptic inhibition in spinal sensory processing and pain control. Physiol Rev 92, 193-235.

The invention claimed is:

1. An in vitro method of assessing the predisposition of a subject to develop an injury-induced chronic mechanical pain and/or an inflammatory-induced chronic thermal pain and treating said subject comprising:
   a) analyzing a biological sample comprising DNA, RNA, or protein for the presence or absence of Myosin 1A (Myo1a) DNA or an alteration in the Myo1a DNA sequence that causes reduced expression of Myo1a or Myo1a loss of function, Myo1a RNA or Myosin 1A (Myo1a) protein; and
   b) selecting and treating a subject that lacks Myo1a DNA or has an alteration in the Myo1a DNA sequence that causes reduced expression of Myo1a or Myo1a loss of function, does not express Myo1a RNA, does not express Myo1a protein or that expresses reduced amounts of Myo1a RNA or Myo1a protein, as compared to a Myo1a homozygote (Myo1a$^{+/+}$) reference subject expressing a functional Myo1a gene or Myo1a protein, with an amount of an opioid, baclofen, pregabalin, TAFA4 or taurine that improves pain tolerance of the subject.

2. The method according to claim 1, wherein the biological sample is a blood, plasma or serum sample that is analyzed for the presence of Myo1a protein.

3. The method according to claim 2, wherein the biological sample comprises DNA and said method comprises sequencing the DNA in said biological sample and analyzing the DNA sequence for the presence or absence of Myo1a DNA or an alteration in the Myo1a DNA sequence that causes reduced expression of Myo1a or Myo1a loss of function.

4. The method according to claim 2, wherein the biological sample is a blood, plasma or serum sample from the subject and said method comprises performing an immunoassay on the biological sample for the presence or amount of Myo1a protein present in said biological sample.

5. The method according to claim 4, wherein the method comprises analyzing a blood sample from the subject.

6. The method according to claim 4, wherein the method comprises analyzing a plasma sample from the subject.

7. The method according to claim 4, wherein the method comprises analyzing a serum sample from the subject.

8. The method according to claim 2, wherein the biological sample comprises RNA and said method comprises performing a polymerase chain reaction (PCR) assay on the biological sample comprising RNA from the subject for the absence or reduced levels of Myo1A RNA.

9. The method according to claim 1, wherein the injury-induced chronic mechanical pain is an inflammatory, a neuropathic or a post-operative chronic mechanical pain.

10. The method according to claim 1, wherein the subject is a mammal or a human being.

* * * * *

UNITED STATES PATENT AND TRADEMARK OFFICE
CERTIFICATE OF CORRECTION

PATENT NO. : 11,180,791 B2
APPLICATION NO. : 16/080315
DATED : November 23, 2021
INVENTOR(S) : Abdelaziz Moqrich It is certified that error appears in the above-identified patent and that said Letters Patent is hereby corrected as shown below:

In the Specification

Column 17,
Line 14, "anti-PKCy" should read --anti-PKC$\gamma$--.

Column 25,
Line 1, "CGRP" should read --CGRP$^+$--.

Signed and Sealed this
Twenty-eighth Day of June, 2022

*Katherine Kelly Vidal*
Katherine Kelly Vidal
*Director of the United States Patent and Trademark Office*